US011726100B2

(12) United States Patent
Gaude et al.

(10) Patent No.: US 11,726,100 B2
(45) Date of Patent: Aug. 15, 2023

(54) METHOD OF TREATING LARGE VESSEL OCCLUSION STROKE

(71) Applicant: Pockit Diagnostics Limited, Cambridge (GB)

(72) Inventors: Edoardo Gaude, Cambridge (GB); Gonzalo Ladreda Mochales, Cambridge (GB); Marcos Ladreda Mochales, Cambridge (GB)

(73) Assignee: POCKIT DIAGNOSTICS LIMITED, Cambridge (GB)

( * ) Notice: Subject to any disclaimer, the term of this patent is extended or adjusted under 35 U.S.C. 154(b) by 0 days.

(21) Appl. No.: 17/934,454

(22) Filed: Sep. 22, 2022

(65) Prior Publication Data

US 2023/0048418 A1 Feb. 16, 2023

Related U.S. Application Data

(63) Continuation of application No. PCT/GB2020/053340, filed on Dec. 22, 2020.

(51) Int. Cl.
*G01N 33/68* (2006.01)
*G01N 33/86* (2006.01)

(52) U.S. Cl.
CPC ......... *G01N 33/6896* (2013.01); *G01N 33/86* (2013.01); *G01N 2800/2871* (2013.01)

(58) Field of Classification Search
CPC ............... G01N 33/6896; G01N 33/86; G01N 2800/2871
See application file for complete search history.

(56) References Cited

U.S. PATENT DOCUMENTS 10,520,513 B2 * 12/2019 Montaner Viallonga .................... G01N 33/48
2012/0040858 A1 2/2012 Ford et al.
2016/0139147 A1 * 5/2016 McConnell ........ G01N 33/6893 435/7.92
2020/0011880 A1 1/2020 Olson et al.

FOREIGN PATENT DOCUMENTS

WO 2020229691 A2 11/2020

OTHER PUBLICATIONS

Lopez-Cancio et al., Eur. Stroke J. 2017, 2(1), Suppl. 1, 245.*
Sato et al. J. Neurol. Sci., 2020, 413, 116814.*
Skoloudik, D. et al., "D-dimers Increase in Acute Ischemic Stroke Patients with the Large Artery Occlusion, but do not Depend on the Time of Artery"; J. Thromb. Thrombolysis (2010); vol. 29, pp. 477-482.
Brouns, R. et al., "Clinical and Biochemical Diagnosis of Small-Vessel Disease in Acute Ischemic Stroke", J. of the Neurological Sciences (2009); vol. 285, pp. 185-190.
Glushakova, O. et al., "Biomarkers for Acute Diagnosis and Management of Stroke in Neurointensive Care Units"; Brain Circulation (2016); pp. 28-47.
Foerch, C. et al., "Diagnostic Accuracy of Plasma Glial Fibrllary Acidic Protein for Differentiating Intracerebral Hemorrhage and Cerebral Ischemica in Patients with Symptoms of Acute Stroke"; Clinical Chemistry (2012); vol. 58:1, pp. 237-245.

* cited by examiner

*Primary Examiner* — Olga N Chernyshev
(74) *Attorney, Agent, or Firm* — Fox Rothschild LLP

(57) ABSTRACT

The invention relates to the diagnosis of stroke resulting from occlusion of one or more large vessels in the brain, and in particular to the diagnosis of stroke resulting from occlusion of one or more large vessels in the brain using one or more biomarkers.

13 Claims, 11 Drawing Sheets

Specification includes a Sequence Listing.

| Clinical parameter | Group Numbers (LVO/Non-LVO) | Mean/Median All Patients | SD/IQR All Patients | Mean/Median LVO | SD/IQR LVO | Mean/Median Non-LVO | SD/IQR Non-LVO | Corrected P-value |
|---|---|---|---|---|---|---|---|---|
| NIHSS score (Median, IQR) *** | 23/98 | 4 | 7 | 18 | 9 | 3 | 5 | <0.001 |
| Atrial Fibrillation (%Yes) *** | 23/105 | 18% | na | 52% | na | 10% | na | <0.001 |
| SBP (Mean, SD) * | 23/104 | 154 | 29 | 140 | 22 | 157 | 29 | 0.03 |
| Albumin (Median, IQR) | 23/105 | 43 | 5 | 41 | 5 | 43 | 5 | 0.29 |
| HDL-Cholesterol (Median, IQR) | 20/82 | 1.4 | 0.5 | 1.2 | 0.4 | 1.4 | 0.6 | 0.29 |
| Pulse (Median, IQR) | 23/104 | 78 | 21 | 85 | 36 | 78 | 19.5 | 0.52 |
| Urea (Median, IQR) | 23/105 | 5.7 | 3.0 | 6.8 | 2.7 | 5.5 | 2.9 | 0.52 |
| Sodium (Median, IQR) | 23/104 | 140 | 3 | 139 | 3 | 140 | 3 | 0.54 |
| APTT (Median, IQR) | 21/93 | 30 | 5 | 29 | 5 | 30 | 6 | 0.66 |
| Total HDL-Cholesterol (Median, IQR) | 20/82 | 2.9 | 1.3 | 3.3 | 1.2 | 2.8 | 1.2 | 0.66 |
| Haematocrit (Median, IQR) | 23/105 | 0.40 | 0.06 | 0.38 | 0.07 | 0.41 | 0.06 | 0.78 |
| Basophil.Count (Median, IQR) | 23/104 | 0.05 | 0.03 | 0.04 | 0.03 | 0.05 | 0.03 | 0.78 |
| Monocyte.Count (Median, IQR) | 23/104 | 0.7 | 0.3 | 0.7 | 0.3 | 0.6 | 0.3 | 0.81 |
| PT (Median, IQR) | 21/93 | 12 | 1 | 12 | 0 | 12 | 1 | 0.81 |
| DBP (Median, IQR) | 23/104 | 83 | 21 | 80 | 24 | 83 | 18 | 0.85 |
| Platelet Count (Median, IQR) | 23/104 | 243 | 82 | 227 | 76 | 247 | 85 | 0.85 |
| RBC (Mean, SD) | 23/105 | 4.4 | 0.5 | 4.3 | 0.6 | 4.5 | 0.5 | 0.85 |
| CRP (Median, IQR) | 21/103 | 5 | 2 | 5 | 4 | 5 | 2 | 0.85 |
| Cholesterol (Median, IQR) | 20/82 | 4.2 | 1.5 | 4.1 | 0.7 | 4.3 | 1.7 | 0.85 |
| Fibrinogen (Median, IQR) | 21/93 | 4.7 | 1.2 | 4.9 | 1.3 | 4.7 | 1.1 | 0.87 |
| Hypertension (%Yes) | 23/105 | 60% | na | 70% | na | 58% | na | 0.87 |
| Haemoglobin (Mean, SD) | 23/105 | 133 | 17 | 130 | 20 | 133 | 16 | 0.87 |
| Phosphate (Median, IQR) | 19/99 | 1.0 | 0.2 | 1.0 | 0.2 | 1.0 | 0.2 | 0.87 |
| Alanine Transaminase (Median, IQR) | 23/99 | 16 | 10 | 15 | 8 | 17 | 12 | 0.87 |
| NLR (Median, IQR) | 23/104 | 3.1 | 3.3 | 3.1 | 2.2 | 3.2 | 3.4 | 0.87 |
| Gender (F/M) | 23/105 | 71/57 | na | 11/12 | na | 60/45 | na | 0.90 |
| Creatinine (Median, IQR) | 23/105 | 78 | 31 | 80 | 29 | 74 | 32 | 0.95 |
| Age (Median, IQR) | 23/105 | 76 | 18 | 75 | 13 | 77 | 21 | 1.00 |
| OBT (Median, IQR) | 23/105 | 158 | 162 | 155 | 179 | 161 | 154 | 1.00 |
| Blood Processing Time (Median, IQR) | 23/105 | 22 | 11 | 24 | 11 | 22 | 10 | 1.00 |
| MCV (Median, IQR) | 23/105 | 91 | 7 | 92 | 6 | 91 | 8 | 1.00 |
| MCH (Median, IQR) | 23/105 | 30 | 3 | 30 | 3 | 30 | 3 | 1.00 |
| WBC (Median, IQR) | 23/105 | 8.3 | 3.6 | 8.3 | 2.5 | 8.4 | 3.6 | 1.00 |
| Neutrophil Count (Median, IQR) | 23/104 | 5.4 | 3.1 | 5.3 | 1.8 | 5.4 | 3.4 | 1.00 |
| Lymphocyte Count (Median, IQR) | 23/104 | 1.7 | 1.0 | 1.7 | 0.6 | 1.7 | 1.1 | 1.00 |
| Eosinophil Count (Median, IQR) | 23/104 | 0.13 | 0.15 | 0.13 | 0.13 | 0.12 | 0.15 | 1.00 |
| Potassium (Mean, SD) | 23/100 | 4.3 | 0.5 | 4.3 | 0.4 | 4.3 | 0.5 | 1.00 |
| Total Protein (Mean, SD) | 23/102 | 69 | 5 | 70 | 5 | 69 | 5 | 1.00 |
| Calcium (Median, IQR) | 19/100 | 2.4 | 0.1 | 2.4 | 0.1 | 2.4 | 0.1 | 1.00 |
| Bilirubin (Median, IQR) | 23/103 | 7 | 4 | 6 | 6 | 7 | 4 | 1.00 |
| Alkalike Phosphatase (Median, IQR) | 23/105 | 79 | 28.25 | 80 | 38 | 79 | 26 | 1.00 |
| Triglycerides (Median, IQR) | 20/82 | 1.3 | 0.8 | 1.3 | 0.6 | 1.3 | 0.9 | 1.00 |

FIG. 1

| | DDimer | OPN | OPG |
|---|---|---|---|
| Cut-off (pg/mL) | 1253215 | 1656 | 125 |
| LVO | 12 | 12 | 12 |
| NonLVO | 11 | 29 | 27 |
| Accuracy | 83 (78-87) | 69 (63-74) | 70 (65-76) |
| Sensitivity | 52 (38-67) | 52 (38-67) | 52 (38-67) |
| Specificity | 89 (86-93) | 72 (66-78) | 74 (68-81) |
| LR+ | 5.22 (3.18-8.67) | 1.91 (1.30-2.65) | 2.06 (1.40-2.96) |
| LR- | 0.53 (0.37-0.68) | 0.66 (0.46-0.87) | 0.65 (0.44-0.84) |
| OR | 10.34 (4.65-20) | 3.05 (1.48-5.63) | 3.36 (1.68-6.32) |
| P-value | 2.70E-05 | 0.028003892 | 0.022415927 |

FIG. 4

| | AIC | Deviance | AUC | LR (df) p-value |
|---|---|---|---|---|
| DDimer+OPN+OPG | 105 | 97 | 0.82 (0.73-0.91) | NA |
| DDimer+OPN+OPG+GFAP | 102 | 92 | 0.82 (0.72-0.93) | 5.01 (1), 0.03 |

FIG. 5

| | Beta | CI | OR (95% CI) | P-value |
|---|---|---|---|---|
| DDimer | 2.9 | 0.68 to 1.82 | 1.13 (1.07 to 1.2) | <0.001 |
| OPN | 1.0 | -0.06 to 1.22 | 1.06 (0.99 to 1.13) | 0.08 |
| OPG | 1.3 | 0.07 to 1.98 | 1.10 (1.01 to 1.22) | 0.04 |
| GFAP | -4.2 | -0.01 to 0.0002 | 1 (0.99 to 1) | 0.49 |
| vWF | 0.8 | -0.0002 to 0 | 1 (1 to 1) | 0.19 |
| ADAMTS13 | 0.4 | -1.15 to 2.52 | 1.07 (0.89 to 1.29) | 0.5 |

| Model | Parameters | Beta | CI | OR (95% CI) | Pvalue |
|---|---|---|---|---|---|
| Biomarkers | D-dimer | 3.30 | 0.81 to 2.05 | 15.98 (5.05 to 60.25) | <0.001 |
| | GFAP | -1.65 | -1.45 to -0.04 | 0.28 (0.06 to 0.92) | 0.03 |
| C-STAT | C-STAT | 2.32 | 0.47 to 1.28 | 2.35 (1.60 to 3.61) | <0.001 |
| C-STAT + biomarkers | C-STAT | 3.02 | 0.6 to 1.73 | 3.03 (1.82 to 5.67) | <0.001 |
| | D-dimer | 3.26 | 0.75 to 2.16 | 16.56 (4.46 to 75.93) | <0.001 |
| | GFAP | -2.48 | -1.79 to -0.36 | 0.15 (0.03 to 0.48) | <0.01 |
| EMSA | EMSA | 4.47 | 0.56 to 1.4 | 2.54 (1.74 to 4.07) | <0.001 |
| EMSA + biomarkers | EMSA | 5.7 | 0.68 to 1.86 | 3.29 (1.98 to 6.4) | <0.001 |
| | D-dimer | 3.38 | 0.74 to 2.32 | 18.4 (4.44 to 103.73) | <0.001 |
| | GFAP | -3.15 | -2.32 to -0.41 | 0.09 (0.01 to 0.44) | 0.01 |
| FAST | FAST | 3.79 | 0.91 to 2.27 | 4.61 (2.48 to 9.71) | <0.001 |
| FAST + biomarkers | FAST | 4.85 | 1.14 to 3 | 7.07 (3.12 to 20.06) | <0.001 |
| | D-dimer | 3.47 | 0.79 to 2.36 | 19.79 (4.83 to 111.98) | <0.001 |
| | GFAP | -2.77 | -2.08 to -0.35 | 0.12 (0.02 to 0.5) | 0.01 |
| FAST-ED | FAST-ED | 4.14 | 0.48 to 1.03 | 2.07 (1.62 to 2.8) | <0.001 |
| FAST-ED + biomarkers | FAST-ED | 6.3 | 0.7 to 1.67 | 3.03 (2.02 to 5.3) | <0.001 |
| | D-dimer | 3.66 | 0.7 to 2.67 | 23.43 (4.06 to 209.78) | 0.001 |
| | GFAP | -3.95 | -2.79 to -0.73 | 0.05 (0 to 0.23) | <0.01 |
| RACE | RACE | 3.9 | 0.36 to 0.74 | 1.7 (1.43 to 2.1) | <0.001 |
| RACE + biomarkers | RACE | 5.01 | 0.43 to 1.05 | 1.98 (1.53 to 2.86) | <0.001 |
| | D-dimer | 3.5 | 0.71 to 2.47 | 20.38 (4.14 to 138.41) | <0.001 |
| | GFAP | -3.57 | -2.91 to -0.43 | 0.06 (0 to 0.43) | 0.03 |

FIG. 8

| | AIC | Deviance | AUC | LR (df), p-value |
|---|---|---|---|---|
| D-dimer+GFAP | 100.33 | 94.33 | 81 (74-88) | - |
| **FAST** | **93.35** | **89.35** | **83 (78-88)** | - |
| FAST+D-dimer+GFAP | 71.82 | 63.82 | 93 (90-97) | 25.53 (4), <0.001 |
| **FAST-ED** | **78.25** | **74.25** | **91 (86-95)** | - |
| FAST-ED+D-dimer+GFAP | 51.12 | 43.12 | 95 (91-100) | 31.12 (4), <0.001 |
| **RACE** | **78.87** | **74.87** | **87 (82-93)** | - |
| RACE+D-dimer+GFAP | 59.21 | 51.21 | 93 (89-98) | 23.65 (4), <0.001 |
| **C-STAT** | **102.6** | **98.6** | **79 (72-86)** | - |
| C-STAT+D-dimer+GFAP | 79.29 | 71.29 | 88 (81-94) | 27.31 (4), <0.001 |
| **EMSA** | **89.75** | **85.75** | **84 (79-89)** | - |
| EMSA+D-dimer+GFAP | 70.34 | 62.34 | 93 (89-97) | 23.40 (4), <0.001 |

FIG. 9

| | All | LVO | NonLVO | Pvalue |
|---|---|---|---|---|
| N | 128 | 23 | 105 | |
| DDimer | 504287 (654576) | 1312888 (2003360) | 424713 (445926) | <0.001 |
| OPN | 1250 (1190) | 1706 (1052) | 1155 (1092) | 0.02 |
| OPG | 100 (63) | 125 (60) | 96 (54) | 0.01 |
| vWF | 12398962 (6897117) | 12891161 (7427834) | 12030404 (7251824) | 0.16 |
| ADAMTS13 | 1000898 (303052) | 1074084 (296962) | 985125 (305503) | 0.47 |
| GFAP | 39 (20) | 39 (11) | 39 (21) | 0.41 |

FIG. 11

| | All | LVO | Non-LVO | P-value |
|---|---|---|---|---|
| N | 122 | 23 | 99 | |
| FAST_ED | 1 (3) | 5 (3) | 1 (2) | 4.23E-10 |
| RACE | 1 (3) | 7 (6) | 0 (2) | 5.05E-09 |
| C_STAT | 0 (1) | 1 (2) | 0 (0) | 2.35E-08 |
| EMSA | 3 (4) | 5 (1) | 2 (3) | 1.95E-07 |
| FAST | 1 (1) | 2 (1) | 1 (2) | 2.99E-07 |

FIG. 12

| Model | (Intercept) | DDimer | GFAP | OPN | OPG | C_STAT | EMSA | FAST | FAST_ED | RACE |
|---|---|---|---|---|---|---|---|---|---|---|
| Model ~ DDimer + C_STAT | -17.81 | 1.16 | - | - | - | 0.76 | - | - | - | - |
| Model ~ DDimer + EMSA | -20.36 | 1.14 | - | - | - | - | 0.94 | - | - | - |
| Model ~ DDimer + FAST | -20.72 | 1.21 | - | - | - | - | - | 1.60 | - | - |
| Model ~ DDimer + FAST_ED | -19.13 | 1.35 | - | - | - | - | - | - | 0.68 | - |
| Model ~ DDimer + RACE | -19.76 | 1.23 | - | - | - | - | - | - | - | 0.51 |
| Model ~ DDimer + GFAP + C_STAT | -17.59 | 1.40 | -0.96 | - | - | 1.33 | - | - | - | - |
| Model ~ DDimer + GFAP + EMSA | -20.85 | 1.46 | -1.22 | - | - | - | 1.19 | - | - | - |
| Model ~ DDimer + GFAP + FAST | -20.89 | 1.49 | -1.07 | - | - | - | - | 1.96 | - | - |
| Model ~ DDimer + GFAP + FAST_ED | -20.01 | 1.58 | -1.53 | - | - | - | - | - | 1.11 | - |
| Model ~ DDimer + GFAP + RACE | -18.56 | 1.51 | -1.38 | - | - | - | - | - | - | 0.68 |
| Model ~ DDimer + OPN + OPG + C_STAT | -26.31 | 1.16 | - | 0.86 | 0.48 | 0.67 | - | - | - | - |
| Model ~ DDimer + OPN + OPG + EMSA | -38.65 | 1.18 | - | 1.38 | 1.44 | - | 1.32 | - | - | - |
| Model ~ DDimer + OPN + OPG + FAST | -31.55 | 1.30 | - | 0.64 | 1.34 | - | - | 1.60 | - | - |
| Model ~ DDimer + OPN + OPG + FAST_ED | -26.36 | 1.19 | - | 0.77 | 0.25 | - | - | - | 0.65 | - |
| Model ~ DDimer + OPN + OPG + RACE | -31.83 | 1.22 | - | 0.93 | 1.13 | - | - | - | - | 0.51 |
| Model ~ DDimer + OPN + OPG + GFAP + C_STAT | -25.70 | 1.32 | -0.93 | 0.85 | 0.66 | 1.01 | - | - | - | - |
| Model ~ DDimer + OPN + OPG + GFAP + EMSA | -45.34 | 1.49 | -1.50 | 1.73 | 2.33 | - | 1.53 | - | - | - |
| Model ~ DDimer + OPN + OPG + GFAP + FAST | -33.44 | 1.42 | -1.18 | 0.70 | 1.81 | - | - | 2.08 | - | - |
| Model ~ DDimer + OPN + OPG + GFAP + FAST_ED | -25.57 | 1.56 | -1.47 | 0.66 | 0.21 | - | - | - | 1.05 | - |
| Model ~ DDimer + OPN + OPG + GFAP + RACE | -35.04 | 1.53 | -1.53 | 0.99 | 1.97 | - | - | - | - | 0.73 |

FIG. 13

| Model | Cutoff | Sensitivity | Specificity | PLR | NLR |
|---|---|---|---|---|---|
| Model ~ DDimer + C_STAT | 0.44 | 61 (39-80) | 91 (83-96) | 7 (3-14) | 0.43 (0.26-0.72) |
| Model ~ DDimer + EMSA | 0.34 | 74 (52-90) | 91 (83-96) | 8 (4-16) | 0.29 (0.14-0.57) |
| Model ~ DDimer + FAST | 0.44 | 61 (39-80) | 91 (83-96) | 7 (3-14) | 0.43 (0.26-0.72) |
| Model ~ DDimer + FAST_ED | 0.33 | 87 (66-97) | 94 (87-98) | 14 (7-32) | 0.14 (0.05-0.4) |
| Model ~ DDimer + RACE | 0.33 | 78 (56-93) | 92 (85-96) | 10 (5-19) | 0.24 (0.11-0.51) |
| Model ~ DDimer + GFAP + C_STAT | 0.39 | 74 (52-90) | 93 (86-97) | 10 (5-22) | 0.28 (0.14-0.56) |
| Model ~ DDimer + GFAP + EMSA | 0.34 | 87 (66-97) | 95 (89-98) | 17 (7-41) | 0.14 (0.05-0.39) |
| Model ~ DDimer + GFAP + FAST | 0.33 | 78 (56-93) | 93 (86-97) | 11 (5-23) | 0.23 (0.11-0.51) |
| Model ~ DDimer + GFAP + FAST_ED | 0.39 | 91 (72-99) | 96 (90-99) | 23 (9-60) | 0.09 (0.02-0.34) |
| Model ~ DDimer + GFAP + RACE | 0.24 | 83 (61-95) | 93 (86-97) | 12 (6-24) | 0.19 (0.08-0.46) |
| Model ~ DDimer + OPN + OPG + C_STAT | 0.37 | 70 (47-87) | 91 (83-96) | 8 (4-15) | 0.33 (0.18-0.62) |
| Model ~ DDimer + OPN + OPG + EMSA | 0.37 | 78 (56-93) | 93 (86-97) | 11 (5-23) | 0.23 (0.11-0.51) |
| Model ~ DDimer + OPN + OPG + FAST | 0.45 | 65 (43-84) | 93 (86-97) | 9 (4-20) | 0.37 (0.21-0.66) |
| Model ~ DDimer + OPN + OPG + FAST_ED | 0.37 | 78 (56-93) | 93 (86-97) | 11 (5-23) | 0.23 (0.11-0.51) |
| Model ~ DDimer + OPN + OPG + RACE | 0.33 | 74 (52-90) | 92 (85-96) | 9 (5-19) | 0.28 (0.14-0.57) |
| Model ~ DDimer + OPN + OPG + GFAP + C_STAT | 0.26 | 83 (61-95) | 92 (85-96) | 10 (5-20) | 0.19 (0.08-0.46) |
| Model ~ DDimer + OPN + OPG + GFAP + EMSA | 0.31 | 87 (66-97) | 91 (83-96) | 10 (5-18) | 0.14 (0.05-0.41) |
| Model ~ DDimer + OPN + OPG + GFAP + FAST | 0.38 | 78 (56-93) | 92 (85-96) | 10 (5-19) | 0.24 (0.11-0.51) |
| Model ~ DDimer + OPN + OPG + GFAP + FAST_ED | 0.39 | 91 (72-99) | 96 (90-99) | 23 (9-60) | 0.09 (0.02-0.34) |
| Model ~ DDimer + OPN + OPG + GFAP + RACE | 0.29 | 91 (72-99) | 92 (85-96) | 11 (6-22) | 0.09 (0.03-0.36) |

FIG. 14

METHOD OF TREATING LARGE VESSEL OCCLUSION STROKE

CROSS-REFERENCE TO RELATED APPLICATIONS

This application is a continuation of PCT/GB2020/053340, filed Dec. 22, 2020, which claims the benefit of priority to GB Application No.: 2005632.1, filed Apr. 17, 2020, each of which is incorporated herein by reference in its entirety.

REFERENCE TO A SEQUENCE LISTING

This application includes a Sequence Listing submitted electronically as an xml file named 34421-46001-Seq-Listing.xml, created on Sep. 9, 2022, with a size of 28.2 kilobytes. The Sequence Listing is incorporated herein by reference.

FIELD

The invention relates to the diagnosis of stroke resulting from occlusion of one or more large vessels in the brain, and in particular to the diagnosis of stroke resulting from occlusion of one or more large vessels in the brain using one or more biomarkers.

BACKGROUND

Stroke affects 16 million people in the world every year. More than 30% of these patients die and 90% of survivors develop permanent disabilities. Stroke is defined by the World Health Organisation as a clinical syndrome consisting of rapidly developing clinical signs of focal (or global in case of coma) disturbance of cerebral function with symptoms lasting 24 hours or longer or leading to death with no apparent cause other than a vascular origin. The definition of stroke thus excludes transient ischemic attack (TIA), which presents with the same or similar symptoms to stroke, but is a temporary disruption in the blood supply to part of the brain and is defined as lasting less than 24 hours; and stroke mimics, which are non-vascular conditions which present with neurological deficits simulating stroke, which include seizures and postictal paralysis; toxic-metabolic disturbances; brain tumours; infections, and migraine.

There are two main types of stroke: ischemic stroke and haemorrhagic stroke. The treatment regime for each is very different due to their different aetiologies.

Haemorrhagic stroke is due to the rupture of a blood vessel in the brain with consequent bleeding. There are two main types of haemorrhagic stroke: intracerebral haemorrhage (bleeding within the brain itself, due to either intraparenchymal haemorrhage (bleeding within the brain tissue) or intraventricular haemorrhage (bleeding within the brain's ventricular system)); and subarachnoid haemorrhage, (bleeding within the skull but outside of the brain tissue; more precisely, bleeding between the arachnoid mater and pia mater). Haemorrhagic stroke represents around 15% of stroke seen in patients.

Ischemic stroke is defined as the physical blockage of blood flow to an area of the brain, and represents around 85% of stroke seen in patients.

One type of ischemic stroke is stroke resulting from small vessel occlusion (SVO, also referred to as lacunar stroke). SVO stroke or lacunar stroke is caused by occlusion of one or more small vessels, typically that supply deep brain structures.

However, the deadliest type of ischemic stroke is stroke resulting from large vessel occlusion (LVO) or simply LVO stroke. LVO stroke results from occlusion of one or more large vessels in the brain[1] including the common carotid artery, basilar artery, vertebral artery, middle cerebral artery, anterior cerebral artery, posterior cerebral artery, external carotid artery, internal carotid artery and/or anterior cerebral arteries. Stroke resulting from LVO contributes disproportionately to stroke-related dependence and death[1].

The typical treatment for patients identified as suffering or having suffered from LVO stroke is mechanical thrombectomy (MT). MT is a surgical procedure that mechanically removes the clot via a probe inserted at the level of the groin. MT is typically only useful to treat LVO stroke, as the vessels affected in other types of ischemic strokes (such as SVO stroke) cannot be reached by the mechanical probe due to their depth within the brain and/or are too small to accommodate the mechanical probe. Treatment of LVO patients with MT significantly increases the chances of survival, as well as decreases the extent of disability[2-4]. Mechanical thrombectomy has been proven a safe and effective treatment for LVO stroke until 24 hours from stroke onset[3], indicating that detection of LVO strokes several hours after onset can significantly aid the stroke care pathway. Improved speed and/or accuracy of identification of those individuals who present with stroke symptoms who are or who have suffered a LVO stroke is very important to ensure that they are treated by MT, and achieve revascularisation.

However, ischemic and haemorrhagic stroke typically present with similar symptoms. In addition, different types of ischemic stroke can present with similar symptoms. Further to this, patients presenting with stroke-like symptoms may be suffering from a TIA or stroke mimic, and/or may be suffering from more than one pathology. These factors mean that accurate diagnosis of stroke type can be challenging.

Typically, diagnosis of stroke is achieved or informed using computerised tomography (CT) scan to the head. CT is highly accurate for detection of brain haemorrhages, but can be very inaccurate for detection of ischemic stroke, and LVO stroke specifically. An MRI scan may also be carried out, to aid with diagnosis of ischemic stroke and ischemic stroke type. If LVO stroke is suspected, the patient typically undergoes a further procedure, called CT angiography. Examination of CTA and/or MRI images by a neuroradiologist are then required in order to diagnose LVO stroke.

Diagnosis of LVO stroke in an individual presenting with stroke symptoms can therefore be a lengthy procedure, and requires expert (neuroradiological) input. A delay in diagnosis and treatment negatively impacts on patient outcome. A diagnostic which is able to identify or aid identification of individuals who have suffered an LVO stroke could speed up treatment of these patients, thereby reducing death and disability rates.

Several studies have investigated the ability of clinical scores based on patient symptoms to aid in the diagnosis of LVO strokes[5-10]. Such clinical scores are generally based on a simplified form of the widely applied national institute of health stroke scale (NIHSS) system, but none of them has shown improved diagnostic performance compared to the NIHSS system for the identification of LVO strokes[11]. Although the NIHSS system has shown promising results in the identification of LVO strokes[12], cut-off values applied to a real clinical scenario have shown poor diagnostic performance[13]. This indicates that clinical scores alone are not sufficient to diagnose LVO stroke.

Several documents report the use of biomarker measurements for differential diagnosis of stroke subtype. WO2012009567 describes the measurement of an expression profile to determine whether a patient is suffering an ischemic stroke. WO2016087611 describes a method for the differentiation of ischemic and haemorrhagic stroke subtypes by measurement of a panel of blood biomarkers. Other studies have assessed the ability of blood biomarkers to differentiate between stroke subtypes and aid in the acute stroke diagnosis. Sharma et al measured 262 proteins and found that a panel of 5 proteins could distinguish between any stroke type and mimics[14], but no biomarker was suggested for differentiation between stroke subtypes. Bustamante et al tested a panel of 21 biomarkers for the differentiation between stroke and mimics, as well as between ischemic stroke and haemorrhagic stroke[15]. Their study concluded that the tested biomarkers were not sufficient for an accurate diagnosis of stroke, or stroke subtype, in the acute clinical setting. Other studies have attempted to identify biomarkers for the diagnosis of LVO strokes. Wang et al found a significant association between plasma soluble CD40L/P-selectin and LVO stroke patients[16]. Arenillas and colleagues observed increased amounts of blood c-reactive protein (CRP) in patients with intracranial large-artery occlusive strokes[17]. Chang et al reported association between cardiac biomarkers and LVO strokes[18]. However, there is currently no means for diagnosing, specifically, stroke resulting from LVO.

SUMMARY OF THE INVENTION

In accordance with a first aspect, there is provided a method of diagnosing stroke as a result of a large vessel occlusion (LVO), comprising determining the amount of at least two biomarkers in a sample taken from an individual identified as or suspected of having or having had a stroke wherein the biomarker(s) are selected from: succinate, succinic-glutathione, N-acetyl-aspartate, propionyl-carnitine, glutamate, heart fatty acid binding protein (H-FABP), brain fatty acid binding protein (B-FABP), Abeta 1-40, osteoprotegerin (OPG), soluble tumor necrosis factor-like weak inducer of apoptosis (sTWEAK), pro-vWF, retinol binding protein 4 (RBP4), ADAMTS13, NMDA receptor 2 peptide (NR2 peptide), 20-HETE, bilirubin, brain natriuretic peptide (BNP), glial fibrillary acidic protein (GFAP), D-dimer, C-reactive Protein (CRP), matrix metalloproteinase 9 (MMP9), interleukin 6 (IL-6), osteopontin (OPN), Troponin I, s100b, von Willebrand Factor (vWF), or P-selectin.

In accordance with a second aspect, there is a method of identifying, from a group of individuals identified as or suspected of having or having had a stroke, individuals who have suffered a stroke as a result of LVO, comprising determining the amount of at least two biomarkers in a sample taken from each individual, wherein the biomarkers are selected from: succinate, succinic-glutathione, N-acetyl-aspartate, propionyl-carnitine, glutamate, heart fatty acid binding protein (H-FABP), brain fatty acid binding protein (B-FABP), Abeta 1-40, osteoprotegerin (OPG), soluble tumor necrosis factor-like weak inducer of apoptosis (sTWEAK), pro-vWF, retinol binding protein 4 (RBP4), ADAMTS13, NMDA receptor 2 peptide (NR2 peptide), 20-HETE, bilirubin, brain natriuretic peptide (BNP), glial fibrillary acidic protein (GFAP), D-dimer, C-reactive Protein (CRP), matrix metallo-proteinase 9 (MMP9), interleukin 6 (IL-6), osteopontin (OPN), Troponin I, s100b, von Willebrand Factor (vWF) or P-selectin.

In some embodiments methods comprise determining the amount of at least three, at least four, at least five, at least six, at least seven, at least eight, at least nine, at least 10, at least eleven, or 12 or more biomarkers.

In some embodiments the methods comprise comparing the amount of each biomarker in the sample taken from the or each individual identified as or suspected of having or having had a stroke to the amount of the same biomarker in one or more of a control, a positive standard, one or more positive references or a negative reference.

In some embodiments the individual is diagnosed as having or having had a stroke as a result of LVO when the amount of one or more of the measured biomarkers differs from the amount of the same biomarker in a control; or is comparable to the amount of the same biomarker in a positive standard.

In some embodiments the methods comprise transforming the amount of one or more biomarkers measured in the sample taken from an or each individual identified as or suspected of having or having had a stroke into an LVO stroke score.

In some embodiments, the methods comprise comparing the LVO stroke score created using the measured biomarker amounts in a sample taken from an individual identified as or suspected of having or having had a stroke to an LVO stroke score created using biomarker amounts from a control, or from a positive standard.

In some embodiments the individual is diagnosed as having or having had a stroke as a result of LVO when the LVO stroke score created using the measured biomarker amounts in a sample taken from an individual identified as or suspected of having or having had a stroke is comparable to an LVO stroke score created using biomarker amounts from a positive standard; or when the LVO stroke score created using the measured biomarker amounts in a sample taken from an individual identified as or suspected of having or having had a stroke differs from the LVO stroke score created using biomarker amounts from a control.

In some embodiments, the sample from the individual is one or more of blood, plasma, cerebrospinal fluid or saliva.

In some embodiments, the amount of biomarker is determined using an agent that binds to the biomarker. In some such embodiments the detection and/or quantification of the amount of biomarker or biomarkers comprises the use of ELISA. In some such embodiments the detection and/or quantification of the amount of biomarker or biomarkers comprises the use of a lateral flow assay.

In some embodiments the method further comprises consideration of data and/or information from one or more clinical assessments which the individual has undergone. In some such embodiments the clinical assessment is one or more of a CT or CTA scan, MRA or MRI scan, or the individual's NIHSS, FAST, ABCD, ABCD2 Rosier, TOAST, EMSA, PASS, VAN, RACE, FAST_ED or CPSS score.

In some embodiments, the amount of biomarker in the sample taken from the individual identified as or suspected of having or having had a stroke is determined using an agent that binds to the biomarker, preferably wherein the amount of biomarker is determined using ELISA or lateral flow.

In some embodiments, the method is carried out within about 24 hours of onset of stroke symptoms in the individual. In some embodiments, the method is carried out within about 17 hours of onset of stroke symptoms in the individual. In some embodiments, the method is carried out within about 6 hours of onset of stroke symptoms in the individual.

In accordance with a third aspect, there is provided the use of two or more biomarkers to detect stroke resulting from large vessel occlusion, wherein the biomarkers are selected from: succinate, succinic-glutathione, N-acetyl-aspartate, propionyl-carnitine, glutamate, heart fatty acid binding protein (H-FABP), brain fatty acid binding protein (B-FABP), Abeta 1-40, OPG, soluble tumor necrosis factor-like weak inducer of apoptosis (sTWEAK), pro-vWF, retinol binding protein 4 (RBP4), ADAMTS13, NMDA receptor 2 peptide (NR2 peptide), 20-HETE, bilirubin, brain natriuretic peptide (BNP), glial fibrillary acidic protein (GFAP), D-dimer, C-reactive Protein (CRP), matrix metallo-proteinase 9 (MMP9), interleukin 6 (IL-6), osteopontin (OPN), Troponin I, s100b, von Willebrand Factor (vWF), osteoprotegerin (OPG) or P-selectin.

In some embodiments, at least three, at least four, at least five, at least six, at least seven, at least eight, at least nine, at least ten, at least eleven or twelve or more biomarkers are used to identify stroke resulting from large vessel occlusion.

In a sixth aspect there is provided a kit for carrying out a method according to the first or second aspect of the invention comprising one or more of: a container for holding a sample from the individual identified as or suspected of having or having had a stroke; a means for determining the amount of the target biomarker(s); and instructions on how to carry out the reaction between the sample and the means provided so as to determine the amount of the target biomarker(s).

DETAILED DESCRIPTION

It has been found that detection of certain amounts of specific biomarkers in a sample from an individual can determine or inform the decision as to whether the individual has suffered a stroke resulting from LVO.

Accordingly, in a first aspect there is provided a method of diagnosing stroke as a result of a large vessel occlusion (LVO) comprising determining the amount of at least two biomarkers in a sample taken from an individual identified as or suspected of having or having had a stroke, wherein the biomarker are selected from: succinate, succinic-glutathione, N-acetyl-aspartate, propionyl-carnitine, glutamate, heart fatty acid binding protein (H-FABP), brain fatty acid binding protein (B-FABP), Abeta 1-40, OPG, soluble tumor necrosis factor-like weak inducer of apoptosis (sTWEAK), pro-vWF, retinol binding protein 4 (RBP4), ADAMTS13, NMDA receptor 2 peptide (NR2 peptide), 20-HETE, bilirubin, brain natriuretic peptide (BNP), glial fibrillary acidic protein (GFAP), D-dimer, C-reactive Protein (CRP), matrix metallo-proteinase 9 (MMP9), interleukin 6 (IL-6), osteopontin (OPN), Troponin I, s100b, von Willebrand Factor (vWF), osteoprotegerin (OPG) or P-selectin.

The phrase 'stroke as a result of large vessel occlusion (LVO)', also referred to herein as 'LVO stroke' means stroke resulting from occlusion of one or more of the common carotid artery, basilar artery, vertebral artery, middle cerebral artery, anterior cerebral artery, posterior cerebral artery, external carotid artery, internal carotid artery and/or anterior cerebral arteries.

As used herein, the phrase "an individual suspected of having or having had a stroke" refers to an individual presenting with one or more signs or symptoms associated with stroke. This can include an individual suffering from a TIA or stroke mimic. The phrase "an individual identified as having or having had a stroke" as used herein indicates an individual presenting with one or more signs or symptoms associated with stroke who has, in addition, been diagnosed as having or having had a stroke.

Signs or symptoms associated with stroke include arm drift, sudden-onset face weakness, hemiplegia and muscle weakness of the face, abnormal speech as well as combination thereof such as the FAST test, reduction in sensory or vibratory sensation, numbness, initial flaccidity (hypotonicity), replaced by spasticity (hypertonicity), obligatory synergies and, in particular, when they appear in one side of the body (unilateral), altered smell, taste, hearing, or vision (total or partial), hyperreflexia, decreased reflexes (e.g. gag, swallow, pupil reactivity to light), decreased sensation and muscle weakness of the face, drooping of eyelid (ptosis) and weakness of ocular muscles, balance problems and nystagmus, aphasia, dysarthria, apraxia, altered breathing and heart rate, atrial fibrillation, weakness in sternocleidomastoid muscle with inability to turn head to one side, weakness in tongue (inability to protrude and/or move from side to side), visual field defect, hemineglect, disorganized thinking, memory deficits, confusion, lack of insight of his or her, usually stroke-related, disability, altered movement coordination, altered walking gait, vertigo, hypersexual gestures, headache and or disequilibrium.

The method may be performed in vivo, in vitro or ex vivo. Preferably, the method is performed in vitro or ex vivo. Most preferably, the method is performed in vitro.

In some embodiments the method comprises determining the amount of at least three, at least four, at least five, at least six, at least seven, at least eight, at least nine, at least 10, at least eleven, or 12 or more biomarkers.

As described in the Examples and shown in FIGS. 2A and 3, the inventors have shown for the first time that the biomarkers OPN, OPG, and D-dimer are surprisingly effective in determining whether a subject has suffered from stroke as a result of a large vessel occlusion (LVO).

Thus, preferably, the method comprises determining the amount of at least one of the biomarkers selected from: D-dimer, OPN and OPG. More preferably, the method comprises determining the amount of at least two of the biomarkers selected from: D-dimer, OPN and OPG. Most preferably, the method comprises determining the amount of D-dimer, OPN and OPG.

Preferably, the method comprises determining the amount of D-dimer. Preferably, the method comprises determining the amount of OPN. Preferably, the method comprises determining the amount of OPG.

The inventor's further work has shown that inclusion of the additional biomarker, GFAP, results in even greater accuracy in diagnosing stroke as a result of a large vessel occlusion (LVO), as summarised in FIG. 5 and FIG. 14 The findings suggest that inclusion of GFAP in the biomarker panel could help to rule out haemorrhagic stroke from the population of suspected stroke patients.

Accordingly, preferably, the method comprises determining the amount of at least one of the biomarkers selected from: D-dimer, OPN, OPG and GFAP. More preferably, the method comprises determining the amount of at least two of the biomarkers selected from: D-dimer, OPN, OPG and GFAP. Even more preferably, the method comprises determining the amount of at least three of the biomarkers selected from: D-dimer, OPN, OPG and GFAP. Most preferably, the method comprises determining the amount of biomarkers: D-dimer, OPN, OPG and GFAP.

As shown in FIG. 14, surprisingly the specific combination of D-dimer with GFAP results in a specificity of diagnosis of over 90%.

Accordingly, preferably the method comprises determining the amount of D-dimer and GFAP.

In one embodiment, the D-dimer protein sequence may be represented by the Entrez GeneID: 2243 which is provided herein as SEQ ID No: 1, as follows:

```
                                     [SEQ ID No: 1]
MFSMRIVCLV LSVVGTAWTA DSGEGDFLAE GGGVRGPRVV
ERHQSACKDSDWPFCSDEDW NYKCPSGCRM KGLIDEVNQD
FTNRINKLKN SLFEYQKNNK DSHSLTTNIM EILRGDFSSA
NNRDNTYNRV SEDLRSRIEV LKRKVIEKVQ HIQLLQKNVR
AQLVDMKRLE VDIDIKIRSC RGSCSRALAR EVDLKDYEDQ
QKQLEQVIAK DLLPSRDRQH LPLIKMKPVP DLVPGNFKSQ
LQKVPPEWKA LTDMPQMRME LERPGGNEIT RGGSTSYGTG
SETESPRNPS SAGSWNSGSS GPGSTGNRNP GSSGTGGTAT
WKPGSSGPGS TGSWNSGSSG TGSTGNQNPG SPRPGSTGTW
NPGSSERGSA GHWTSESSVS GSTGQWHSES GSFRPDSPGS
GNARPNNPDW GTFEEVSGNV SPGTRREYHT EKLVTSKGDK
ELRTGKEKVT SGSTTTTRRS CSKTVTKTVI GPDGHKEVTK
EVVTSEDGSD CPEAMDLGTL SGIGTLDGFR HRHPDEAAFF
DTASTGKTFP GFFSPMLGEF VSETESRGSE SGIFTNTKES
SSHHPGIAEF PSRGKSSSYS KQFTSSTSYN RGDSTFESKS
YKMADEAGSE ADHEGTHSTK RGHAKSRPVR DCDDVLQTHP
SGTQSGIFNI KLPGSSKIFS VYCDQETSLG GWLLIQQRMD
GSLNFNRTWQ DYKRGFGSLN DEGEGEFWLG NDYLHLLTQR
GSVLRVELED WAGNEAYAEY HFRVGSEAEG YALQVSSYEG
TAGDALIEGS VEEGAEYTSH NNMQFSTFDR DADQWEENGA
EVYGGGWWYN NCQAANLNGI YYPGGSYDPR NNSPYEIENG
VVWVSFRGAD YSLRAVRMKI RPLVTQ
```

Accordingly, preferably D-dimer comprises or consists of an amino acid sequence substantially as set out in SEQ ID NO: 1, or a fragment or variant thereof.

In one embodiment, D-dimer may be encoded by a nucleotide sequence which is provided herein as SEQ ID No: 2, as follows:

```
                                       [SEQ ID No: 2]
AATCCTTTCTTTCAGCTGGAGTGCTCCTCAGGAGCCAGCCCCACCCTTAG
AAAAGATGTTTTCCATGAGGATCGTCTGCCTGGTCCTAAGTGTGGTGGGC
ACAGCATGGACTGCAGATAGTGGTGAAGGTGACTTTCTAGCTGAAGGAGG
AGGCGTGCGTGGCCCAAGGGTTGTGGAAAGACATCAATCTGCCTGCAAAG
ATTCAGACTGGCCCTTCTGCTCTGATGAAGACTGGAACTACAAATGCCCT
TCTGGCTGCAGGATGAAAGGGTTGATTGATGAAGTCAATCAAGATTTTAC
AAACAGAATAAATAAGCTCAAAAATTCACTATTTGAATATCAGAAGAACA
```

-continued

```
ATAAGGATTCTCATTCGTTGACCACTAATATAATGGAAATTTTGAGAGGC
GATTTTTCCTCAGCCAATAACCGTGATAATACCTACAACCGAGTGTCAGA
GGATCTGAGAAGCAGAATTGAAGTCCTGAAGCGCAAAGTCATAGAAAAAG
TACAGCATATCCAGCTTCTGCAGAAAAATGTTAGAGCTCAGTTGGTTGAT
ATGAAACGACTGGAGGTGGACATTGATATTAAGATCCGATCTTGTCGAGG
GTCATGCAGTAGGGCTTTAGCTCGTGAAGTAGATCTGAAGGACTATGAAG
ATCAGCAGAAGCAACTTGAACAGGTCATTGCCAAAGACTTACTTCCCTCT
AGAGATAGGCAACACTTACCACTGATAAAAATGAAACCAGTTCCAGACTT
GGTTCCCGGAAATTTTAAGAGCCAGCTTCAGAAGGTACCCCCAGAGTGGA
AGGCATTAACAGACATGCCGCAGATGAGAATGGAGTTAGAGAGACCTGGT
GGAAATGAGATTACTCGAGGAGGCTCCACCTCTTATGGAACCGGATCAGA
GACGGAAAGCCCCAGGAACCCTAGCAGTGCTGGAAGCTGGAACTCTGGGA
GCTCTGGACCTGGAAGTACTGGAAACCGAAACCCTGGGAGCTCTGGGACT
GGAGGGACTGCAACCTGGAAACCTGGGAGCTCTGGACCTGGAAGTACTGG
AAGCTGGAACTCTGGGAGCTCTGGAACTGGAAGTACTGGAAACCAAAACC
CTGGGAGCCCTAGACCTGGTAGTACCGGAACCTGGAATCCTGGCAGCTCT
GAACGCGGAAGTGCTGGGCACTGGACCTCTGAGAGCTCTGTATCTGGTAG
TACTGGACAATGGCACTCTGAATCTGGAAGTTTTAGGCCAGATAGCCCAG
GCTCTGGGAACGCGAGGCCTAACAACCCAGACTGGGGCACATTTGAAGAG
GTGTCAGGAAATGTAAGTCCAGGGACAAGGAGAGAGTACCACACAGAAAA
ACTGGTCACTTCTAAAGGAGATAAAGAGCTCAGGACTGGTAAAGAGAAGG
TCACCTCTGGTAGCACAACCACCACGCGTCGTTCATGCTCTAAAACCGTT
ACTAAGACTGTTATTGGTCCTGATGGTCACAAAGAAGTTACCAAAGAAGT
GGTGACCTCCGAAGATGGTTCTGACTGTCCCGAGGCAATGGATTTAGGCA
CATTGTCTGGCATAGGTACTCTGGATGGGTTCCGCCATAGGCACCCTGAT
GAAGCTGCCTTCTTCGACACTGCCTCAACTGGAAAAACATTCCCAGGTTT
CTTCTCACCTATGTTAGGAGAGTTTGTCAGTGAGACTGAGTCTAGGGGCT
CAGAATCTGGCATCTTCACAAATACAAAGGAATCCAGTTCTCATCACCCT
GGGATAGCTGAATTCCCTTCCCGTGGTAAATCTTCAAGTTACAGCAAACA
ATTTACTAGTAGCACGAGTTACAACAGAGGAGACTCCACATTTGAAAGCA
AGAGCTATAAAATGGCAGATGAGGCCGGAAGTGAAGCCGATCATGAAGGA
ACACATAGCACCAAGAGAGGCCATGCTAAATCTCGCCCTGTCAGAGACTG
TGATGATGTCCTCCAAACACATCCTTCAGGTACCCAAAGTGGCATTTTCA
ATATCAAGCTACCGGGATCCAGTAAGATTTTTTCTGTTTATTGCGATCAA
GAGACCAGTTTGGGAGGATGGCTTTTGATCCAGCAAAGAATGGATGGATC
ACTGAATTTTAACCGGACCTGGCAAGACTACAAGAGAGGTTTCGGCAGCC
TGAATGACGAGGGGGAAGGAGAATTCTGGCTAGGCAATGACTACCTCCAC
TTACTAACCCAAAGGGGCTCTGTTCTTAGGGTTGAATTAGAGGACTGGGC
TGGGAATGAAGCTTATGCAGAATATCACTTCCGGGTAGGCTCTGAGGCTG
AAGGCTATGCCCTCCAAGTCTCCTCCTATGAAGGCACTGCGGGTGATGCT
CTGATTGAGGGTTCCGTAGAGGAAGGGGCAGAGTACACCTCTCACAACAA
```

CATGCAGTTCAGCACCTTTGACAGGGATGCAGACCAGTGGGAAGAGAACT

GTGCAGAAGTCTATGGGGGAGGCTGGTGGTATAATAACTGCCAAGCAGCC

AATCTCAATGGAATCTACTACCCTGGGGGCTCCTATGACCCAAGGAATAA

CAGTCCTTATGAGATTGAGAATGGAGTGGTCTGGGTTTCCTTTAGAGGGG

CAGATTATTCCCTCAGGGCTGTTCGCATGAAAATTAGGCCCCTTGTGACC

CAATAGGCTGAAGAAGTGGGAATGGGAGCACTCTGTCTTCTTTGCTAGAG

AAGTGGAGAGAAAATACAAAAGGTAAAGCAGTTGAGATTCTCTACAACCT

AAAAAATTCCTAGGTGCTATTTTCTTATCCTTTGTACTGTAGCTAAATGT

ACCTGAGACATATTAGTCTTTGAAAAATAAAGTTATGTAAGGTTTTTTTT

ATCTTTAAATAGCTCTGTGGGTTTTAACATTTTTATAAAGATATACCAAG

GGCCATTCAGTACATCAGGAAAGTGGCAGACAGAAGCTTCTCTCTGCAAC

CTTGAAGACTATTGGTTTGAGAACTTCTCTTCCCATACCACCCAAAATCA

TAATGCCATTGGAAAGCAAAAAGTTGTTTTATCCATTTGATTTGAATTGT

TTTAAGCCAATATTTTAAGGTAAAACTCACTGAATCTAACCATAGCTGAC

CTTTGTAGTAGAATTTACAACTTATAATTACAATGCACAATTTATAATTA

CAATATGTATTTATGTCTTTTGCTATGGAGCAAATCCAGGAAGGCAAGAG

AAACATTCTTTCCTAAATATAAATGAAAATCTATCCTTTAAACTCTTCCA

CTAGACGTTGTAATGCACACTTATTTTTTTCCCAAGGAGTAACCAATTTC

TTTCTAAAACACATTTAAAATTTTAAAACTATTTATGAATATTAAAAAAA

GACATAATTCACACATTAATAAACAATCTCCCAAGTATTGATTTAACTTC

ATTTTTCTAATAATCATAAACTATATTCTGTGACATGCTAATTATTATTA

AATGTAAGTCGTTAGTTCGAAAGCCTCTCACTAAGTATGATCTATGCTAT

ATTCAAAATTCAACCCATTTACTTTGGTCAATATTTGATCTAAGTTGCAT

CTTTAATCCTGGTGGTCTTGCCTTCTGATTTTTAATTTGTATCCTTTTCT

ATTAAGATATATTTGTCATTTTCTCTTGAATATGTATTAAAATATCCCAA

GCAA

Accordingly, preferably D-dimer comprises or consists of a nucleotide sequence substantially as set out in SEQ ID NO: 2, or a fragment or variant thereof.

In one embodiment, the OPN protein sequence may be represented by the Entrez GeneID: 6696 which is provided herein as SEQ ID No: 3, as follows:

```
                                                [SEQ ID No: 3]
    MRIAVICFCL  LGITCAIPVK  QADSGSSEEK  QLYNKYPDAV

    ATWLNPDPSQ  KQNLLAPQNA  VSSEETNDFK  QETLPSKSNE

    SHDHMDDMDD  EDDDDHVDSQ  DSIDSNDSDD  VDDTDDSHQS

    DESHHSDESD  ELVTDFPTDL  PATEVFTPVV  PTVDTYDGRG

    DSVVYGLRSK  SKKFRRPDIQ  YPDATDEDIT  SHMESEELNG

    AYKAIPVAQD  LNAPSDWDSR  GKDSYETSQL  DDQSAETHSH

    KQSRLYKRKA  NDESNEHSDV  IDSQELSKVS  REFHSHEFHS

    HEDMLVVDPK  SKEEDKHLKF  RISHELDSAS  SEVN
```

Accordingly, preferably OPN comprises or consists of an amino acid sequence substantially as set out in SEQ ID NO: 3, or a fragment or variant thereof.

In one embodiment, OPN may be encoded by a nucleotide sequence which is provided herein as SEQ ID No: 4, as follows:

[SEQ ID No: 4]
AGCAGCAGGAGGAGGCAGAGCACAGCATCGTCGGGACCAGACTCGTCTCAGGCCAGTTGCAGCCTTCTCA

GCCAAACGCCGACCAAGGTACAGCTTCAGTTTGCTACTGGGTTGTGCATTCAGCTGAATTTCATGGGGAA

GTCCAAATTCTAAGGAAAAATATTTTTAATTGTAATGCTGTTAAACAGACTTAAATTTTCTAGCCTTTTT

AATAAGCAGATTAGATACATTGCAGGTCTCCTGGAACAAAGGTGTCTAGATATTTTGAATGCCAATCAAA

TTTAAAACTTAAAAATACTTCCACTGGGTCCTCAAAAGAACGGAAACCACCGATGCTAATCAGAAAATAG

TAAAATTAAATTCCCCTTTGGAATAATTATACCTATATAATTTTCAGTGGGTGACTGTGCAGGAATTTAA

AAGAAAAGGGATCTTTTATGCTAATTAAACCAATTACAATGCTATTTTTTAAATGATGTATCTCACTTTT

AAGGGGAAGAAAACCCTTTCTGAATATGCCACTGCTAAATTTAGCTGTTAAAATATTCACCAAGATACCT

GTATGACACTGTGTAGGCTTATTATTACAAATAGAAAAGCTGTTGGCTATTTTCAATGTTTTCCTTTGAA

TTTCAAATTTTTAGAACATCTTACTTAAATAACAAATTTCAGAGATAGTTTGATTTCACCTAAGTAGCAC

CTACTTGATAATTAAGCTAAAAGTCACATTTAAAGTACATGTTGGAAAAATGGATAAAGCAAATTTTTTT

CATTTTTTTCTGTGAGTTTTTTCTTCTCTAAAAAATATTCCCATACTAGCTTATTAATATAATTAAGTTA

CTGTTGATCTGTTTGTAGGTTTAGAGAGCTAGATATATAAGGTAGTAATGGTATAATTTCTGGAACTCTA

AATTTTAAAGTTGAATAAATACAGACTTGCAAAATTTCCCTTTCCCTTGCCTAATAGTGAAAGATGGATA

ATAGGTGGCAATATAAATATTAACTTGAAAGACTATAATACTAAAAAGAAAAGGCATCTCTAAGAAGTAG

AAAAGATTCTATAGAAAATATATTTTATTTGTGATCATTTTGTAATGTGGTAGTATAAAAAGGTATCACT

GTTGTAACCTATGAAGATGTCAGCTATTCCTTATGAAATATTTTGCAGGAAAACTCACTACCATGAGAAT

-continued

TGCAGTGATTTGCTTTTGCCTCCTAGGCATCACCTGTGCCATACCAGTGAGTACAGTTGCATCTTAAAGA

AAATTCCTGAAAATAACTGAATTGTGTGCTTCCATGTGCTAGGAGGACATTCTTGTAATCTTTCTTCATC

TTTTCTGTTTCTAAGGTTAAACAGGCTGATTCTGGAAGTTCTGAGGAAAAGCAGGTAAGCATCTTTTATG

TTTTTATATAGTTAAATCATTTACTCAATTATGGCGAGAGGTGCAAGAAACGTATTTGCTGCGATATTAC

TTATCTTCTCAGTCAAATCCATTGGTTTACAAGTATTGATTGACTGCCTGCTATGAATCTAGGCCAGTAC

CAAGCACAGTATAGTTTTTAATAAATATAAGTTTATAAAACCAACCCAGATATTTTAAATATAATAATAT

CTAGGCATGTATGATGAGTTATCGCATGTAAGATAAGTTATATGAAGTTGTGTGACTTTTTTTCCATTAG

TCCACATACTGATCTAAAAGCAGAAAATTCCAGCTTTTGCTTTGTTTAGTGGATTGCTAAGTTTAAAATT

CACATTGGATATTAGTCAGAACTGTTTGTATGACCATAATATTCACAATATTGTCTGAGATATTAGCTGA

GAAGCCCATTGTGAAAAGAAAGTCTATGTGTGCTGTTTGTATCTATTGTGATTGTCAGCTGATGTTAGAT

CACATTTTCTAACCAAACATAAGACCAACCAAACTCTTTATTATAATTATTTGACCAGCACTAAAGATGT

ACCTACCCCTCCACAACAGATGAAACTGTGCCAGCCAAACAACAAATGGGCATTGTCCCCAGAAGCTTGG

ACAAAAAGGCACACAGAGTTCAATTCCAGTTGAACAGAATAAAGGCCAAAATAGAGCTGCCTTGGGGGTC

ACTGCAATTAGACTGCTTAATGAAGACATTAAAAGAAGTATTCTGTGTTCGTTTGTGTGTGGAGGGGTGT

GTGTGTCTGTTTTTCAACTGATTTGAAAATACAGGTGTTGAATCCTAATAATAAACCAGAAAAATTAACA

TCTCCAGAGAAGATAGAGGTCATACTATTTGAGGCAAGAATTAGCGTCTTTTTAATAAACGAAAATATGG

CAAAGATGCATTTTAGAAGGCACGTGGAGCTATAACAATTTAAGAAATACGTGAAGAGCTCAAGGCTCAG

CCTTCTAGAATCCCAGAAACTTAAAGCTAGTAAAAAATTGGGGAAGTCTCTAAGGATATATGCCTGAAAA

TACACACTGGTTATCTGTGAGTGTTAGGATTACTGGGTGGTTTTTAGTCTATTCATTTTGCTTACCTTTA

TTTTCTTCATATTAGTTTTTAAAAATTATAAATGTAACTTATACATCCATTCTCTCTGAGCCTGTATTAC

ATGTGTCATGAGAATAGATAGATAGATATGAAAAAGTGAAGAGAAAAACTCTGAACTCATCTGGTCTCAC

TGTTTTTCCGCCTTCTTTTTTTTTTTTTTTTTTTTTTTTTGAGACGGAGTCTCGCTCCGTCGCCCAGGCT

GGAGTGCAGTGGTGTGATCTCGGCTCACTGCAAGCTCCGCCTCCCAGGTTCACCCCATTCTCCTGAGTAG

CTGGGACTACAGGCGCCCGCCACCACGCCCGGATAATTTTTTGTATTTTTAGTAGAGACGGGGTTTCACC

GTGTTAGCCAGGATGGTCTCCATCTCCTGACCTCGTGATCCACCCTCCTTGGCCTCCCAAAGTGCTGGGA

TTACAGGCGTGAGCCACTGCGCCCGGCTGTTTTTTCATCTTCTTAAAGCAAGGAACCCCTTCTTTCAGCA

AAACCTTTCGGAGAAGCCCAATACTAAGCTCCTCTGGTTAGAGCCAGCCATGAGAGAAACTCCAAGTACT

TCTGACTGGTTCTCTCTCTACTCATCCACCCCTTAGGTGGCTGCAGAAGGAACTCTGTGCAACCCCCAGA

GTTCTCATTCTCAGTGACAGGGAAATGTAATGATTGGCCCTGGATGATTCAGCAGATCAGATGATACTTA

CTCAGAGCAATTTCCACTCCTTTGCAGTAGCATATTATCAGTATTTTCCAGATAAATAACTTGGCTAAAG

AAAAATCCATTTCATTTACATCTTTGGCACCTTACAGCAATAGAACTTTTGTGCAATGATTTTAATATTA

TATTTCTACATTGGCTGATAAGATACATATGGCTATTGAGCACTCAAAATGTGGGCTAGTGCAACTGAGG

AACTGAATTTTTATCTTCTTTTTTTTTTTTTTTTTTTTTGAGATGGAGTCTTGCTCTGTCACCCAGGCTG

GAGTGCAGTGGCGCAATCTTGGCTCACTGCAAGCTCTGCCTCCTGGGTTCACGCCATTCTCTTGCCTCAG

CCTCCCCAGTAGCTGGGGGTACAGGTGCCTGCCACCACGCCCGGCTATTTTTTTTTATTTTTATTTTTTT

TAGTAGAAACGGGGTTTCACTGTGTTAGCCAGGATGTTCTCGATCTCCTGACCTCGTGATCCGCCTGCCT

CGGCCTCCCAAAGTGCTGGGATTACAGGGGTGAGCCACCGTGCCTAGCCATTTCATTTTAATTAACTTAA

ATTTAAATAGCTCCATGTGGTTAGAGGATACTGAATTAGCACAGTCTTAGAGAGTTCCTTCTTGTTCCAT

GGACTGGACACAATGAAGATTAACAGTAATTAAGGTCACTTCTGGTTTAGATGTGCTTTATCTGAGAGGA

AAATTCAGCCAGCAAACATACAAAAAGAAAGCACAGTGTGAAGTTCGGTGTTAAGAGCTAGTTTGCCTGC

-continued

GTTTGAACCCTGCCTGGCTCTGCCATTTCCTACCACTTAACTGCACTGTGGCTGAGTTTTCTGATCTGTA

AGGTGGGAATAATAATGATACCTATCTCATAGGGGAATGAAAGGATCAAATGAGTTCATATTTGTAAAGC

AATTTGAAAGAGTGCCTAGCCCACAGTAAGTGCTACATAAGAGTTTGTTAAATGAATCTGCAAAAAAAAA

AAAATTACAAAAAGGTACCTAAGGGTCCGGGTGACTATATGCTTCCATCAAGACTAGTGAAGAATGGTTG

TTTTTTCCATTCATCCCTACATTTCTTTTTTTAATAATGATAAACATGCAACTTTTTTGTAGCTTTACAA

CAAATACCCAGATGCTGTGGCCACATGGCTAAACCCTGACCCATCTCAGAAGCAGAATCTCCTAGCCCCA

CAGGTATTTTTAAACTTCTCATAATTAAACTACAGTGATGAAAGATAGCCACACTCAGGCCATTTGGGCT

GCTCAGATGAATCCTGCCTGCCTGCTGGCAAACATGTGCTTAGGACATTGACTGATCTGCCATGTTGGCT

TCTCTCTGTGTTAAGCCATCCACAGATGAGGCTGAAAAATAAAAACTGCTTTGGATTAAAAAGGTTAACT

TTTGAATAAAAAAGCTAGGCATGTGTGATGCGCACTAACACGTGCCATTCCTTCTTCAGAATGCTGTGTC

CTCTGAAGAAACCAATGACTTTAAACAAGAGGTAAGTTCTCATTTTCAATCAGAGGCCCATCATGCCTTG

AAGAGATGAAAGAAGGCATTGCCTGGATTCTCTTCTGATGAAATTTCATTAGCAAGTTTTCCAGCTAATT

GGCAGTCTAAAACTTGCTCATAAATAAAACATGTATTTACTAAATATCAGAAATACTAGGTTTCCTCGGA

TAAGTTTAGCATTACAGAAGATGTTTATTAATGCCTGTTATTTGAAACATTAATCTGCTTGCAATTTATT

TAAGGTATTTTGTAGATATCTAATATCTAATAAGCATCTAATTAATGCATATCAAAGCTAAGATTTTGCC

TTTAGGAAAGTTTTCTTTCCTAATAAAATAGTTTATTTGACAACTATTCTTTTTATTAGGATCATTCATA

TATTTGCTAAGCAAAGAGTAAATTTATTTTCCTTAAGATTCAATTTGAATATACTAAGAATATTAAAGCA

AGTTAGATAAATTACCCAATATATTTGTCAATTTGAAATTTGATAGACATTAGTTGTTTAATTCAATGGG

CAGTTTTGAGCTGCAGTTTATACACACATGCATAACAGAGTCACCTTTCAATTATCCATGTTAATAGGAA

AGTGGTTATAGATTTTAGTACACACATTAAAATATGGATACTCTTCTCTTTTGATAAATCTCATTTCAAA

TAAAAAAACCAGTCTCATAATTATGTATCTGTATCTATTACATCATTGAATTTAGTAAATAATGTTTAAT

ATGTATAAGGAAAAACAATGTTATTGACATGAAGATTATACTCACATATTTGGCTTGAAAATATCTATAA

AAATAATTTCTGTTGCAAAGTAAGAAATGTTCTTCAGAATGTTATTAATCCCTGTGTTAAAAGAGAAATT

GGAAGATGCTCACTTTAGCTCCTAAAAGCCATGGTATGTACTGTGAATGCAAAGATTCTGAAACTAAATA

AAAAGAAAGATAGTAAAAGACTAATGTGCTATAAAGGCTAAGGGAAAATAAAAACCCATATATTAATTTT

CCCGGCCATCTTAATTTTCAGACCCTTCCAAGTAAGTCCAACGAAAGCCATGACCACATGGATGATATGG

ATGATGAAGATGATGATGACCATGTGGACAGCCAGGACTCCATTGACTCGAACGACTCTGATGATGTAGA

TGACACTGATGATTCTCACCAGTCTGATGAGTCTCACCATTCTGATGAATCTGATGAACTGGTCACTGAT

TTTCCCACGGACCTGCCAGCAACCGAAGTTTTCACTCCAGTTGTCCCCACAGTAGACACATATGATGGCC

GAGGTGATAGTGTGGTTTATGGACTGAGGTCAAAATCTAAGAAGTTTCGCAGACCTGACATCCAGGTAAA

TCCTTTAACAGACACACCTGATGGTTCTGACTAGCGCTCAAGTCTAGGAAACCACAGTTTGCATATTCAT

TCATTCATTCATCCATTCATTCATCCATTCAGCAAGAATTCATTCATATTCTACTTTATGACCATTGAAT

ACAAATCTTTTTCTGCTTGGCGGTTTTTGTAAGTCTACATAATTTCTCTCTAGATTTGATTCTCAAACAC

AATTCTACTTTTTGAAATCCTGGATCACTTATTTTCAGATTAAAATAAATGGAAAACACCAATTATTTAA

AAAAAATAATGGTCATGTTTTGAAGTTAAATACCTAAGAGGAATTGTAGTTGCAAATTACACTGAATCCT

TAGTCACAGAATCTGGATTTGACATAGCCTTGCCGTTTACTATTCTCTTTACTTTTTAACTAACAATTCA

CTTCCTCTTTATGTAGGTTTCAATATAATGAAACCTACCTCATAGGTTTCATTACATATGTAAGTGATGT

AGTTATTAAACTAAATGAGATGACATATGTGAAAGGCCTTGGTAAAGTACTATACAAAGTAACATGCTAG

TATTATTTCAGCCAGATTTAGACAATTTTTAGTATAAGATGACCTAAAAGCTAGAGAGTGGAAAAGGATT

ACCATATTCCCATCCCTAGCCGTTCATATAATTATTCTTCATTTGTGCCGTGATTCAGTACCCTGATGCT

ACAGACGAGGACATCACCTCACACATGGAAAGCGAGGAGTTGAATGGTGCATACAAGGCCATCCCCGTTG

```
CCCAGGACCTGAACGCGCCTTCTGATTGGGACAGCCGTGGGAAGGACAGTTATGAAACGAGTCAGCTGGA

TGACCAGAGTGCTGAAACCCACAGCCACAAGCAGTCCAGATTATATAAGCGGAAAGCCAATGATGAGAGC

AATGAGCATTCCGATGTGATTGATAGTCAGGAACTTTCCAAAGTCAGCCGTGAATTCCACAGCCATGAAT

TTCACAGCCATGAAGATATGCTGGTTGTAGACCCCAAAAGTAAGGAAGAAGATAAACACCTGAAATTTCG

TATTTCTCATGAATTAGATAGTGCATCTTCTGAGGTCAATTAAAAGGAGAAAAAATACAATTTCTCACTT

TGCATTTAGTCAAAAGAAAAAATGCTTTATAGCAAAATGAAAGAGAACATGAAATGCTTCTTTCTCAGTT

TATTGGTTGAATGTGTATCTATTTGAGTCTGGAAATAACTAATGTGTTTGATAATTAGTTTAGTTTGTGG

CTTCATGGAAACTCCCTGTAAACTAAAAGCTTCAGGGTTATGTCTATGTTCATTCTATAGAAGAAATGCA

AACTATCACTGTATTTTAATATTTGTTATTCTCTCATGAATAGAAATTTATGTAGAAGCAAACAAAATAC

TTTTACCCACTTAAAAAGAGAATATAACATTTTATGTCACTATAATCTTTTGTTTTTTAAGTTAGTGTAT

ATTTTGTTGTGATTATCTTTTTGTGGTGTGAATAAATCTTTTATCTTGAATGTAATAAGAATTTGGTGGT

GTCAATTGCTTATTTGTTTTCCCACGGTTGTCCAGCAATTAATAAAACATAACCTTTTTTACTGCCTA
```

Accordingly, preferably OPN comprises or consists of a nucleotide sequence substantially as set out in SEQ ID NO: 4, or a fragment or variant thereof.

In one embodiment, the OPG protein sequence may be represented by the Entrez Gene ID: 4982 which is provided herein as SEQ ID No: 5, as follows:

```
                                              [SEQ ID No: 5]
MNNLLCCALV FLDISIKWTT QETFPPKYLH YDEETSHQLL

CDKCPPGTYLKQHCTAKWKT VCAPCPDHYY TDSWHTSDEC

LYCSPVCKEL QYVKQECNRT HNRVCECKEG RYLEIEFCLK

HRSCPPGFGV VQAGTPERNT VCKRCPDGFF SNETSSKAPC

RKHTNCSVFG LLLTQKGNAT HDNICSGNSE STQKCGIDVT

LCEEAFFRFA VPTKFTPNWL SVLVDNLPGT KVNAESVERI

KRQHSSQEQT FQLLKLWKHQ NKDQDIVKKI IQDIDLCENS

VQRHIGHANL TFEQLRSLME SLPGKKVGAE DIEKTIKACK

PSDQILKLLS LWRIKNGDQD TLKGLMHALK HSKTYHFPKT

VTQSLKKTIR FLHSFTMYKL YQKLFLEMIG NQVQSVKISC L
```

Accordingly, preferably OPG comprises or consists of an amino acid sequence substantially as set out in SEQ ID NO: 5, or a fragment or variant thereof.

In one embodiment, OPG may be encoded by a nucleotide sequence which is provided herein as SEQ ID No: 6, as follows:

```
                                              [SEQ ID No: 6]
GGAGACGCACCGGAGCGCTCGCCCAGCCGCCGCCTCCAAGCCCCTGAGGT

TTCCGGGGACCACAATGAACAACTTGCTGTGCTGCGCGCTCGTGTTTCTG

GACATCTCCATTAAGTGGACCACCCAGGAAACGTTTCCTCCAAAGTACCT

TCATTATGACGAAGAAACCTCTCATCAGCTGTTGTGTGACAAATGTCCTC

CTGGTACCTACCTAAAACAACACTGTACAGCAAAGTGGAAGACCGTGTGC

GCCCCTTGCCCTGACCACTACTACACAGACAGCTGGCACACCAGTGACGA

GTGTCTATACTGCAGCCCCGTGTGCAAGGAGCTGCAGTACGTCAAGCAGG

AGTGCAATCGCACCCACAACCGCGTGTGCGAATGCAAGGAAGGGCGCTAC

CTTGAGATAGAGTTCTGCTTGAAACATAGGAGCTGCCCTCCTGGATTTGG

AGTGGTGCAAGCTGGAACCCCAGAGCGAAATACAGTTTGCAAAAGATGTC

CAGATGGGTTCTTCTCAAATGAGACGTCATCTAAAGCACCCTGTAGAAAA

CACACAAATTGCAGTGTCTTTGGTCTCCTGCTAACTCAGAAAGGAAATGC

AACACACGACAACATATGTTCCGGAAACAGTGAATCAACTCAAAAATGTG

GAATAGATGTTACCCTGTGTGAGGAGGCATTCTTCAGGTTTGCTGTTCCT

ACAAAGTTTACGCCTAACTGGCTTAGTGTCTTGGTAGACAATTTGCCTGG

CACCAAAGTAAACGCAGAGAGTGTAGAGAGGATAAAACGGCAACACAGCT

CACAAGAACAGACTTTCCAGCTGCTGAAGTTATGGAAACATCAAAACAAA

GACCAAGATATAGTCAAGAAGATCATCCAAGATATTGACCTCTGTGAAAA

CAGCGTGCAGCGGCACATTGGACATGCTAACCTCACCTTCGAGCAGCTTC

GTAGCTTGATGGAAAGCTTACCGGGAAAGAAAGTGGGAGCAGAAGACATT

GAAAAAACAATAAAGGCATGCAAACCCAGTGACCAGATCCTGAAGCTGCT

CAGTTTGTGGCGAATAAAAAATGGCGACCAAGACACCTTGAAGGGCCTAA

TGCACGCACTAAAGCACTCAAAGACGTACCACTTTCCCAAAACTGTCACT

CAGAGTCTAAAGAAGACCATCAGGTTCCTTCACAGCTTCACAATGTACAA

ATTGTATCAGAAGTTATTTTTAGAAATGATAGGTAACCAGGTCCAATCAG

TAAAAATAAGCTGCTTATAACTGGAAATGGCCATTGAGCTGTTTCCTCAC

AATTGGCGAGATCCCATGGATGAGTAAACTGTTTCTCAGGCACTTGAGGC

TTTCAGTGATATCTTTCTCATTACCAGTGACTAATTTTGCCACAGGGTAC

TAAAAGAAACTATGATGTGGAGAAAGGACTAACATCTCCTCCAATAAACC

CCAAATGGTTAATCCAACTGTCAGATCTGGATCGTTATCTACTGACTATA

TTTTCCCTTATTACTGCTTGCAGTAATTCAACTGGAAATTAAAAAAAAAA

AACTAGACTCCATTGTGCCTTACTAAATATGGGAATGTCTAACTTAAATA

GCTTTGAGATTTCAGCTATGCTAGAGGCTTTTATTAGAAAGCCATATTTT
```

-continued

TTTCTGTAAAAGTTACTAATATATCTGTAACACTATTACAGTATTGCTAT

TTATATTCATTCAGATATAAGATTTGTACATATTATCATCCTATAAAGAA

ACGGTATGACTTAATTTTAGAAAGAAAATTATATTCTGTTTATTATGACA

AATGAAAGAGAAAATATATATTTTTAATGGAAAGTTTGTAGCATTTTTCT

AATAGGTACTGCCATATTTTTCTGTGTGGAGTATTTTTATAATTTTATCT

GTATAAGCTGTAATATCATTTTATAGAAAATGCATTATTTAGTCAATTGT

TTAATGTTGGAAAACATATGAAATATAAATTATCTGAATATTAGATGCTC

TGAGAAATTGAATGTACCTTATTTAAAAGATTTTATGGTTTTATAACTAT

ATAAATGACATTATTAAAGTTTTCAAATTATTTTTA

Accordingly, preferably OPG comprises or consists of a nucleotide sequence substantially as set out in SEQ ID NO: 6, or a fragment or variant thereof.

In one embodiment, the GFAP protein sequence may be represented by the Entrez Gene ID: 2670 which is provided herein as SEQ ID No: 7, as follows:

[SEQ ID No: 7]

MERRRITSAA RRSYVSSGEM MVGGLAPGRR LGPGTRLSLA

RMPPPLPTRV DFSLAGALNA GFKETRASER AEMMELNDRF

ASYIEKVRFL EQQNAKLAAE LNQLRAKEPT KLADVYQAEL

RELRLRDLQL TANSARLEVE RDNLAQDLAT VRQKLQDETN

LRLEAENNLA AYRQEADEAT LARLDLERKI ESLEEEIRFL

RKIHEEEVRE LQEQLARQQV HVELDVAKPD LTAALKEIRT

QYEAMASSNM HEAEEWYRSK FADLTDAAAR NAELLRQAKH

EANDYRRQLQ SLTCDLESLR GTNESLERQM REQEERHVRE

AASYQEALAR LEEEGQSLKD EMARHLQYEQ DLLNVKLALD

IEIATYRKLL EGEENRITIP VQTFSNLQIR ETSLDTKSVS

EGHLKRNIVV KTVEMRDGEV IKESKQEHKD VM

Accordingly, preferably GFAP comprises or consists of an amino acid sequence substantially as set out in SEQ ID No: 7, or a fragment or variant thereof.

In one embodiment, GFAP may be encoded by a nucleotide sequence which is provided herein as SEQ ID No: 8, as follows:

[SEQ ID No: 8]

AGAGCCAGAGCAGGATGGAGAGGAGACGCATCACCTCCGCTGCTCGCCGCTCCTACGTCTCCTCAGGGGA

GATGATGGTGGGGGGCCTGGCTCCTGGCCGCCGTCTGGGTCCTGGCACCCGCCTCTCCCTGGCTCGAATG

CCCCCTCCACTCCCGACCCGGGTGGATTTCTCCCTGGCTGGGGCACTCAATGCTGGCTTCAAGGAGACCC

GGGCCAGTGAGCGGGCAGAGATGATGGAGCTCAATGACCGCTTTGCCAGCTACATCGAGAAGGTTCGCTT

CCTGGAACAGCAAAACAAGGCGCTGGCTGCTGAGCTGAACCAGCTGCGGGCCAAGGAGCCCACCAAGCTG

GCAGACGTCTACCAGGCTGAGCTGCGAGAGCTGCGGCTGCGGCTCGATCAACTCACCGCCAACAGCGCCC

GGCTGGAGGTTGAGAGGGACAATCTGGCACAGGACCTGGCCACTGTGAGGCAGAAGCTCCAGGATGAAAC

CAACCTGAGGCTGGAAGCCGAGAACAACCTGGCTGCCTATAGACAGGAAGCAGATGAAGCCACCCTGGCC

CGTCTGGATCTGGAGAGGAAGATTGAGTCGCTGGAGGAGGAGATCCGGTTCTTGAGGAAGATCCACGAGG

AGGAGGTTCGGGAACTCCAGGAGCAGCTGGCCCGACAGCAGGTCCATGTGGAGCTTGACGTGGCCAAGCC

AGACCTCACCGCAGCCCTGAAAGAGATCCGCACGCAGTATGAGGCAATGGCGTCCAGCAACATGCATGAA

GCCGAAGAGTGGTACCGCTCCAAGTTTGCAGACCTGACAGACGCTGCTGCCCGCAACGCGGAGCTGCTCC

GCCAGGCCAAGCACGAAGCCAACGACTACCGGCGCCAGTTGCAGTCCTTGACCTGCGACCTGGAGTCTCT

GCGCGGCACGAACGAGTCCCTGGAGAGGCAGATGCGCGAGCAGGAGGAGCGGCACGTGCGGGAGGCGGCC

AGTTATCAGGAGGCGCTGGCGCGGCTGGAGGAAGAGGGGCAGAGCCTCAAGGACGAGATGGCCCGCCACT

TGCAGGAGTACCAGGACCTGCTCAATGTCAAGCTGGCCCTGGACATCGAGATCGCCACCTACAGGAAGCT

GCTAGAGGGCGAGGAGAACCGGATCACCATTCCCGTGCAGACCTTCTCCAACCTGCAGATTCGAGAAACC

AGCCTGGACACCAAGTCTGTGTCAGAAGGCCACCTCAAGAGGAACATCGTGGTGAAGACCGTGGAGATGC

GGGATGGAGAGGTCATTAAGGAGTCCAAGCAGGAGCACAAGGATGTGATGTGAGGCAGGACCCACCTGGT

GGCCTCTGCCCCGTCTCATGAGGGGCCCGAGCAGAAGCAGGATAGTTGCTCCGCCTCTGCTGGCACATTT

CCCCAGACCTGAGCTCCCCACCACCCCAGCTGCTCCCCTCCCTCCTCTGTCCCTAGGTCAGCTTGCTGCC

CTAGGCTCCGTCAGTATCAGGCCTGCCAGACGGCACCCACCCAGCACCCAGCAACTCCAACTAACAAGAA

ACTCACCCCCAAGGGGCAGTCTGGAGGGGCATGGCCAGCAGCTTGCGTTAGAATGAGGAGGAAGGAGAGA

AGGGGAGGAGGGCGGGGGGCACCTACTACATCGCCCTCCACATCCCTGATTCCTGTTGTTATGGAAACTG

-continued

TTGCCAGAGATGGAGGTTCTCTCGGAGTATCTGGGAACTGTGCCTTTGAGTTTCCTCAGGCTGCTGGAGG

AAAACTGAGACTCAGACAGGAAAGGGAAGGCCCCACAGACAAGGTAGCCCTGGCCAGAGGCTTGTTTTGT

CTTTTGGTTTTTATGAGGTGGGATATCCCTATGCTGCCTAGGCTGACCTTGAACTCCTGGGCTCAAGCAG

TCTACCCACCTCAGCCTCCTGTGTAGCTGGGATTATAGATTGGAGCCACCATGCCCAGCTCAGAGGGTTG

TTCTCCTAGACTGACCCTGATCAGTCTAAGATGGGTGGGGACGTCCTGCCACCTGGGGCAGTCACCTGCC

CAGATCCCAGAAGGACCTCCTGAGCGATGACTCAAGTGTCTCAGTCCACCTGAGCTGCCATCCAGGGATG

CCATCTGTGGGCACGCTGTGGGCAGGTGGGAGCTTGATTCTCAGCACTTGGGGGATCTGTTGTGTACGTG

GAGAGGGATGAGGTGCTGGGAGGGATAGAGGGGGGCTGCCTGGCCCCCAGCTGTGGGTACAGAGAGGTCA

AGCCCAGGAGGACTGCCCCGTGCAGACTGGAGGGGACGCTGGTAGAGATGGAGGAGGAGGCAATTGGGAT

GGCGCTAGGCATACAAGTAGGGGTTGTGGGTGACCAGTTGCACTTGGCCTCTGGATTGTGGGAATTAAGG

AAGTGACTCATCCTCTTGAAGATGCTGAAACAGGAGAGAAAGGGGATGTATCCATGGGGGCAGGGCATGA

CTTTGTCCCATTTCTAAAGGCCTCTTCCTTGCTGTGTCATACCAGGCCGCCCCAGCCTCTGAGCCCCTGG

GACTGCTGCTTCTTAACCCCAGTAAGCCACTGCCACACGTCTGACCCTCTCCACCCCATAGTGACCGGCT

GCTTTTCCCTAAGCCAAGGGCCTCTTGCGGTCCCTTCTTACTCACACACAAAATGTACCCAGTATTCTAG

GTAGTGCCCTATTTTACAATTGTAAAACTGAGGCACGAGCAAAGTGAAGACACTGGCTCATATTCCTGCA

GCCTGGAGGCCGGGTGCTCAGGGCTGACACGTCCACCCCAGTGCACCCACTCTGCTTTGACTGAGCAGAC

TGGTGAGCAGACTGGTGGGATCTGTGCCCAGAGATGGGACTGGGAGGGCCCACTTCAGGGTTCTCCTCTC

CCCTCTAAGGCCGAAGAAGGGTCCTTCCCTCTCCCCAAGACTTGGTGTCCTTTCCCTCCACTCCTTCCTG

CCACCTGCTGCTGCTGCTGCTGCTAATCTTCAGGGCACTGCTGCTGCCTTTAGTCGCTGAGGAAAAATAA

AGACAAATGCTGCGCCCTTCCCCAGAGTGGACTCTGATCTGTTCATGAGAGGGCGGGACTGGGGCCAAGA

TGTAGCCTTTGACAAGACCAACTCATTTCTTATTACTGATCATCTCTGGGGCCCATGCCCTCACCAAATT

CCACCCGCAGCCAAAGAGGACATACACCAGCTCCCTCCACTCTTTTCTTCCTTCCTCTCCCTGCTACCTG

CAACTCAACCAGCACAATCTTCATAGGCAAGAAAGCAAAGCAGCTCAAACATGATTCAACACTGATCAGT

GTTTACCACTGGATAAATCTGAGTTCACACTTTCCTTCTCTGACCTAAATGTGAAGTCAGGAAACACATG

TGCCCTACTTCCATCCTGAGCTCAGTCCCCAATCTCCCACCAGCCTCAGGCCCCTCCACTTCTCAGATCA

GGTCCCAGACCTGCCCATGAAAATGGGGAGCAGGCTGTAACAGATTTGTCCACATGTTCCTACCACCTGT

CCCAACCCAGGGTACCCACCCAGAGACATCTGGTATCATTTAACAAACACATTGAAGGACAACTGGTCTT

CAGAGCTGAAGAGAGCTCCTAGGGGGAGAAGCTGGGACAACAGTGAAATAAGTAGCAGCAGCAACGACAG

AAGTGAATGGTGACAAAGACTGCTGTGATGAGCAGGTAGCCTATCAGGGTGAGCTCCACAGCCGAGCGAG

TCTCAGGATCTGAGAACGAGGCTGGGTAGTGCCCATGAGATGTCACACCCAGCCGGAAGCCAGCAACTAG

CACACCCTGCCTCCAGCAATAGTAGATGCCCCGGTCATCCAGCTGGGTGAAGCGGATGTGGAGCTGGTTG

CCGTGGTCAATGAACACCCTCATGGACCTGTTGACACCCTTCAGGTACTGTGTGCGGTAGAGGTGCTGGC

GGTCTTTGTCCCAGGCCACTGCATGCTCTGGCCGGGCCCCAGGACAGGAGATGATGAGTCCATGGCCCAG

TCTCTGCTGGTGGAACTGAATGGGCACCTGGGGCACCCAGGGCCGGCTGCCCACTTTGGACACATAGTTA

ATGATGGCCAGCACGCCCTCCCGGATGGTCTTTGTCTTCTCACAGGGTACTAAGCAGCTCCGAACCAGCA

CCTCAGGCGTGTGGTCCCTGGCCTTGGTCCGCAGCTTCCTTGGCACAGCCCTTGAGCCACAAGACACCAC

ATCGGGCACGGCCTTGAGGTAGCGTGGGGAGAGGTCTGGGCTCTGCAGGTAGCAGAGGCCGATGCGCCAC

TGCTCCCCACGCACTCCGCAGCGGTCACAGGGGGTCCATTCCCAGAAGGTGGTGAAGACATGGAGGTGCC

CATAGTATTCATCTGCAAAGGGCTCCTGGCCCTTGTCCTGGAAAGTGGCCACCATTCCCTCACTGTTCTG

GATGTCCACATCGTAGGCGTAAAAGTAGTCCCCCTTGCGGGTGCCGCAGAAGTACAGGCCTGAGTCCTCA

GACTGAGCCCTGAAAACCAACAAGCTGAACATGCGGATGCTGAAGCGGGTCAGCATGTCGCTGCCCACAC

-continued

```
GTACCTGGGCTGCCTCCGTCAGCACCCGCCCATCAAAGTCCGTCAGCACTTTGGTGTGGCTGCTACCTAG

GTGCTTTTGGTAGAACCAGACTACAGCTGGCACCTCTTCGGGTTTGCAGTGACAGGGAAGCTCAAAGCTC

ATGTCGGCCAGGTAGGCTGCATTTTCAAACATCAGGAAAGCAGGGCAGGGGGTCCTCTGAAAAATGTTTT

CCTTCTCCACAATTTCAAAGGCCTGGAGCCCCCATGCCCACAGGAGCACAGTGGTGAGGGCCAGGTGCAT

ACCTGAAGGAGGCAGGGGTCAGAGGGGCAGGGCAAAACCAGGGCATTAAAGGCTCATAGGGCTCCTAGAA

AGCTCTGCTAAGCGGAAGCCTCTAGATGAGGAAAGGATTATGCAGCCAGGAAAAGCAGCAACAATCTGCA

GAGGAAGCCGCCAAGTGCAAGGCAATTTATTCCCAGTGGATGTACAAGATGCCCTTCTAACATTCCAGAC

CTGATCTCAGGGTGGGGGGGGAAAGCCATTCTAGAACCTGGCCTTTACTCCCCTTTCTAGAACACTGGCG

CTCACCCAAGAATGGGTCAAAGGAAACCGGAATGAGAAGGGCGGGCCGAGGTGCTCGGGCAGGGAGATCT

CTGCCTCAGTGCTCCAGGCCCTGCCCTGCCAGCCTGGTGGAAAAGTCTTTCATCAACCTGGGGGATGAAG

GAAACCCACCCTCCTGCATATCTGGCCATCCGGGAGGCTGGCTGGACCTGAGCTGATGGCTTGGGACTTT

CCCAGGCCCAACCTGCACAAGAACTGAGTCTCTAGGGGAAAATTCAACACCTCAAATGATGTAGTATTTG

ATCATTTGTTGATTACATGTCCATTCATTGGTTTGGGGCTATAAACATTCTTGTTAAGAGCTGTGGAGAT

CAGTGTTTGTTTACCATAAAGATTTTGCTTTTTCCCTTTTA
```

Accordingly, preferably GFAP comprises or consists of a nucleotide sequence substantially as set out in SEQ ID No: 8, or a fragment or variant thereof.

The skilled person would understand that there are a number of natural variants of the referenced biomarkers and that the method may extend to the detection of any one of these naturally occurring variants of D-dimer, OPN, OPG and GFAP.

The sample may be any fluid and/or tissue taken or derived from the individual identified as or suspected of having or having had a stroke. In some embodiments the sample is one or more of cells, tissues, cerebral spinal fluid (CSF), whole blood, serum, plasma, cytosolic fluid, urine, faeces, stomach fluids, tears, digestive fluids, saliva, nasal or other airway fluid, vaginal fluids or semen. In some embodiments more than one sample may be taken from the individual. In some embodiments, two or more samples are taken from the individual. In some such embodiments the samples may be different, for example the samples may be whole blood and CSF; saliva and whole blood; whole blood, CSF and tears. In some embodiments, the sample from the individual is one or more of blood, plasma, cerebrospinal fluid or saliva. Preferably, the sample is a whole blood or plasma sample. More preferably, the sample is a plasma sample. Most preferably, the sample is a whole blood sample.

In some embodiments, the sample or samples taken from the individual are processed prior to analysis to detect and/or quantify any biomarker in the sample. The need for processing and/or the type of processing of the sample required depends upon the biomarker to be detected and/or the assay to be used to detect the biomarker. In some embodiments, the sample may need to be diluted with, for example, saline solution to obtain a concentration appropriate for the biomarker detection assay.

A whole blood sample may be processed to provide blood plasma and/or blood serum using standard procedures in the art. For example, whole blood sample may be centrifuged at 2000 g for 15 minutes at 4° C. to provide blood plasma, which can then be used directly or diluted with saline solution as required for the biomarker detection assay.

The sample is then analysed, to detect the presence of the target biomarker(s) and/or to determine the amount of the target biomarker(s) in the sample. Where more than one sample has been taken from the individual, analysis of the samples may be carried out simultaneously or sequentially. Samples from more than one individual may be analysed simultaneously and/or in the same assay.

Analysis may be carried out by any suitable means. For example, analysis may be carried out by one or more of ELISA, lateral flow immunochromatographic assay (lateral flow), radioimmunoassay, radioassay, enzyme activity assay, cellular assay, western blot, Southern blot, northern blot, immunoprecipitation, immunofluorescence, liquid chromatography, high performance liquid chromatography, positron emission tomography, mass spectrometry, RT-PCR, PCR, mass spectroscopy, gel electrophoresis, mass-sensing BioCD protein array, electrochemical immunoassay, surface enhanced Raman spectroscopy, fluorescence based detection, flow cytometry, nanoparticle based detection, quantum dot technology and protein microarray.

In some embodiments the analysis technique involves use of one or more agents that recognise and bind to a biomarker in the sample. The agent may have the ability to bind to more than one biomarker.

In some embodiments, the agent is a monoclonal or polyclonal antibody. The agent may be an intact antibody, a fragment (e.g., Fab or F(ab')2), or an engineered variant thereof (e.g., sFv). Such antibodies can be of any immunoglobulin class, and any subclass thereof, including IgG, IgM, IgE, IgA, IgD. Suitable antibodies are commercially available, for example from Abcam (Cambridge, UK).

The agent may be labelled to allow detection. Suitable detectable labels are known in the art. As an example, conjugation of an agent with horseradish peroxidase (HRP) allows detection of the agent by addition of an appropriate substrate that can be transformed by enzymatic action of HRP to produce a colour change. Other examples of detectable labels include alkaline phosphatase, peroxidase, colloidal gold, fluorescent compounds, biotin, radioisotopes, luminescent compounds, magnetic particles, and other enzymes. Detectable labels and labelling kits are commercially available from, for example, Expedeon Ltd, Cambridge, UK.

A primary/secondary antibody system may also be used to detect and/or determine the amount of biomarker in a sample. In such a system, a sample is contacted with a primary antibody that specifically recognizes and binds to one or more biomarkers. Subsequently, a secondary antibody with an appropriate label that recognizes the species or isotype of the primary antibody is contacted with the sample. Detection of the one or more biomarkers in the sample is achieved by measuring the signal generated by a labelling molecule conjugated to the secondary antibody.

An antibody produced in a different species may be used for detection of a biomarker bound by a first antibody. For example, a first antibody generated in rabbit; and a secondary anti-species antibody able to recognise and bind the primary antibody generated in a rabbit.

The agent may have the ability to bind to more than one biomarker, one or more of which are bound to a substrate. In such embodiments, the agents may be bound with spatial overlap. In some such embodiments the agents may be differentially labelled to allow detection, for example the use of colour intensity-based labels allows detection and quantification of each spatially overlapping bound biomarker.

In some embodiments, the sample may be immobilised on a suitable substrate, such as a physical substrate such as a nitrocellulose or PVDF membrane, a rigid substrate made of polystyrene, or other plastic polymer such as a microtiter plate. The substrate may then be contacted with an antibody that specifically recognises and binds to a first biomarker. Washing of the substrate helps to ensure specific binding of the antibody to the target biomarker. The antibody may be labelled, for example through conjugation with a detectable label such as an enzyme, fluorophore, or radioisotope. Detection of the label and quantification of the amount of binding may be achieved by suitable means. Alternatively, a secondary antibody conjugated with a detectable label that binds to the biomarker-first antibody complex may be added, followed by washing to remove additional antibody and ensure that the presence of the detectable label on the substrate is indicative of the sample containing the biomarker being measured.

Alternatively, a biomarker-specific antibody may be immobilised on the substrate, which is then contacted with a biomarker, itself being conjugated with a detectable label. Contact of the labelled biomarker with the antibody causes the antibody to bind the labelled biomarker. The sample is then contacted with the substrate in conditions that allow binding of the biomarker to the antibody. Since the biomarker in the sample is not labelled, displacement of the labelled biomarker from the antibody results in a reduction in the amount of detectable label on the substrate after washing and indicates that the sample contains the biomarker.

Alternative agents include peptides, aptamers, enzymes, or small molecules that specifically bind to a target biomarker. For example, an aptamer that specifically binds H-FABP might be used. Aptamers are nucleic acid-based molecules that bind specific ligands. Methods for making aptamers with a particular binding specificity are known as detailed in U.S. Pat. Nos. 5,475,096; 5,670,637; 5,696,249; 5,270,163; 5,707,796; 5,595,877; 5,660,985; 5,567,588; 5,683,867; 5,637,459; and 6,011,020.

Quantification of the amount of biomarker in a sample may be carried out using any suitable assay. For example, an antibody-based assay, or immunosorbent assay such as ELISA, lateral flow, radioimmunoassays or immunoprecipitation. In some embodiments, the analysis is carried out using ELISA. In some embodiments, the analysis is carried out using a lateral flow assay.

Alternative and/or complementary methods may be used to detect non-immunogenic molecules or compounds, such as metabolites, catabolites, peptides, hormones, signalling molecules, small molecules, drugs or any other compound or molecule that, in its naturally occurring form, may not be recognised or bound by an antibody. Such methods include colorimetric methods, enzymatic methods, gas chromatography (GC) and gas chromatography-mass spectrometry (GC-MS), high-performance liquid chromatography (HPLC) and high-performance liquid chromatography-mass spectrometry (HPLC-MS), nuclear magnetic resonance (NMR) spectroscopy, Raman spectroscopy. For example, a suitable colorimetric method may be based upon a chemical reaction similar to that originally described by König [Journal fur Praktische Chemie, 1904, 70, 19-56 & Journal fur Praktische Chemie, 1904, 69, 105-137].

Moreover, techniques for measuring a biomarker in vivo include introducing a binding agent that specifically recognises and binds the biomarker into a patient.

In some embodiments the amount of a biomarker in the sample taken from the individual identified as or suspected of having or having had a stroke is compared to a negative reference, and/or one or more positive references.

A negative reference is a laboratory solution such as a saline solution or buffer, where the target biomarker is absent, or the amount of the target biomarker is known to be undetectable. A positive reference is a laboratory solution such as a saline solution or buffer, comprising the target biomarker in a known amount. The biomarker used to create the positive and/or negative references may be the isolated target biomarker, or a version thereof, such as a recombinant or synthetic version of the biomarker.

In some embodiments, the amount of biomarker in the sample taken from the individual identified as or suspected of having or having had a stroke may be compared to a negative reference and/or a range of positive references comprising different, known amounts of the target biomarker.

In some embodiments a difference between the amount of biomarker in the sample taken from the individual identified or suspected as having or having had a stroke and the negative reference is indicative that the individual has suffered a stroke as a result of LVO. In some embodiments, a statistically significant difference between the amount of biomarker in the sample taken from the individual identified or suspected as having or having had a stroke and the negative reference is indicative that the individual has suffered a stroke as a result of LVO. In some embodiments a correlation between the amount of biomarker in the sample taken from the individual identified or suspected as having or having had a stroke and a positive reference determines or provides an indication of the amount of that biomarker in the sample from the individual.

Alternatively, or in addition, the amount of a biomarker in the sample taken from the individual identified or suspected as having or having had a stroke may be compared to the amount of the same biomarker in a control.

A control is a sample or data generated from a sample taken from one or more healthy individuals. The term ‘healthy individual’ as used herein means an individual who has no signs or symptoms of stroke and who has no history of stroke. Alternatively or in addition, the control may be a sample or data generated from a sample taken from one or more individuals who are having or who have had a TIA, stroke mimic, haemorrhagic stroke or stroke resulting from small vessel occlusion. The term "individuals who are having or who have had a TIA, stroke mimic, haemorrhagic stroke or stroke resulting from small vessel occlusion" as used herein means individuals who are or have been determined, by clinical assessment, to be suffering a TIA, stroke mimic, haemorrhagic stroke or stroke resulting from small vessel occlusion. Such patients may be included in the control group (i.e. contribute a sample for inclusion in the control) until neurological symptoms associated with the TIA, stroke mimic haemorrhagic stroke or stroke resulting from small vessel occlusion have ceased. Preferably, a control is a sample or data taken from one or more patients that have not suffered from LVO stroke. Preferably, a control is a sample or data taken from patients that have suffered from non-LVO stroke. Preferably, the control is a sample or data taken from: ischemic non-LVO, haemorrhagic, and/or non-stroke patients.

In some embodiments a difference between the amount of biomarker in the sample taken from the individual identified or suspected as having or having had a stroke and the control is indicative that the individual has suffered a stroke as a result of LVO. In some embodiments, a statistically significant difference between the amount of biomarker in the sample taken from the individual identified or suspected as having or having had a stroke and the control is indicative that the individual has suffered a stroke as a result of LVO.

Alternatively or in addition, the amount of a biomarker in the sample from the individual may be compared to the amount of the same biomarker in a positive standard. A positive standard is a sample or data generated from a sample taken from an individual who presents with one or more signs or symptoms associated with stroke who has, in addition, been diagnosed as having or having had a stroke as a result of LVO.

In some embodiments, a comparable amount of biomarker in the sample taken from the individual identified as or suspected of having or having had a stroke and the positive standard is indicative that the individual has suffered a stroke as a result of LVO. In some embodiments, a statistically significant difference between the amount of biomarker in the sample taken from the individual identified as or suspected of having or having had a stroke and the positive standard is indicative that the individual has suffered a stroke as a result of LVO.

In some embodiments, a ratio between two or more biomarkers may be calculated, wherein the ratio is the amount of one biomarker (the 'target biomarker') relative to the amount of the other biomarker (the 'reference biomarker'). In some embodiments, the reference biomarker is in a control, a positive reference or a positive standard; for example, the amount of biomarker in a sample taken from an individual suspected of having a LVO stroke may be compared to a sample or data generated from a sample taken from one or more healthy individuals. In some embodiments the target and reference biomarkers are from the same sample, for example the amount of succinate may be compared to the amount of GFAP in a sample taken from an individual suspected of having a LVO stroke. Alternatively or in addition, the level of a biomarker(s) may be analysed in samples taken from the same individual at different times, for example, the amount of GFAP may be compared in two samples taken from an individual before and after the individual has suffered a stroke. In some embodiments a positive ratio is indicative that the individual has suffered a stroke as a result of LVO, whilst a negative ratio is indicative that the individual has not suffered a stroke as a result of LVO, wherein the phrase "a positive ratio" denotes an increased amount of a test biomarker relative to a reference biomarker; and "a negative ratio" refers to a decreased amount of a test biomarker relative to the amount of a reference biomarker. A neutral ratio describes no difference or effectively no difference in the amounts of the test and reference biomarker.

Preferably, an increase in the amount of one or more of the biomarkers selected from: D-dimer, OPN and OPG when compared to a healthy or non-LVO control or negative reference, is indicative that the individual has suffered a stroke as a result of LVO.

Preferably, an increase in the amount of two or more of the biomarkers selected from: D-dimer, OPN and OPG when compared to a healthy or non-LVO control or negative reference, is indicative that the individual has suffered a stroke as a result of LVO. Preferably, an increase in the amount of the biomarkers selected from: D-dimer, OPN and OPG when compared to a healthy or non-LVO control or negative reference, is indicative that the individual has suffered a stroke as a result of LVO. Preferably, an increase in the amount of D-dimer, OPN, and/or OPG when compared to a healthy or non-LVO control or negative reference, is indicative that the individual has suffered a stroke as a result of LVO. Preferably, an increase in the amount of D-dimer, OPN and OPG when compared to a healthy or non-LVO control or negative reference, is indicative that the individual has suffered a stroke as a result of LVO.

Preferably, a decrease in the amount of GFAP when compared to a healthy or non-LVO control or negative reference, is indicative that the individual has suffered a stroke as a result of LVO. Preferably, a decrease in the amount of GFAP when compared to a healthy or haemorrhagic stroke control or negative reference, is indicative that the individual has suffered a non-haemorrhagic stroke, preferably as a result of LVO. Preferably, an increase in the amount of GFAP when compared to a healthy or non-haemorrhagic control or negative reference, is indicative that the individual has suffered a haemorrhagic stroke.

Preferably, an increase in the amount of D-dimer, OPN and/or OPG and a decrease in the amount of GFAP when compared to a healthy or non-LVO control or negative reference, is indicative that the individual has suffered a stroke as a result of LVO. Preferably, an increase in the amount of D-dimer, OPN and OPG and a decrease in the amount of GFAP when compared to a healthy or non-LVO control or negative reference, is indicative that the individual has suffered a stroke as a result of LVO.

The amount of biomarker may relate to the concentration of the biomarker polypeptide sequence. Preferably, the concentration of the biomarker polypeptide sequence relates to the concentration of the biomarker in whole blood. Preferably, the concentration of the biomarker polypeptide sequence relates to the concentration of the biomarker in plasma.

Preferably, a concentration of at least 0.5 μg/ml of D-dimer protein is indicative that the individual has suffered a stroke as a result of LVO. Preferably, a concentration of at least 1 μg/ml of D-dimer protein is indicative that the individual has suffered a stroke as a result of LVO. Preferably, a concentration of at least 1.2 μg/ml of D-dimer protein is indicative that the individual has suffered a stroke as a result of LVO. Preferably, a concentration of at least 1.3 μg/ml of D-dimer protein is indicative that the individual has suffered a stroke as a result of LVO. Preferably, a concentration of at least 1.4 μg/ml of D-dimer protein is indicative that the individual has suffered a stroke as a result of LVO.

Preferably, a concentration of at least 1.5 μg/ml of D-dimer protein is indicative that the individual has suffered a stroke as a result of LVO.

Preferably, a concentration of at least 100 pg/ml of OPG protein is indicative that the individual has suffered a stroke as a result of LVO. Preferably, a concentration of at least 105 pg/ml of OPG protein is indicative that the individual has suffered a stroke as a result of LVO. Preferably, a concentration of at least 110 pg/ml of OPG protein is indicative that the individual has suffered a stroke as a result of LVO. Preferably, a concentration of at least 120 pg/ml of OPG protein is indicative that the individual has suffered a stroke as a result of LVO. Preferably, a concentration of at least 125 pg/ml of OPG protein is indicative that the individual has suffered a stroke as a result of LVO. Preferably, a concentration of at least 150 pg/ml of OPG protein is indicative that the individual has suffered a stroke as a result of LVO. Preferably, a concentration of at least 200 pg/ml of OPG protein is indicative that the individual has suffered a stroke as a result of LVO.

Preferably, a concentration of at least 1 ng/ml of OPN protein is indicative that the individual has suffered a stroke as a result of LVO. Preferably, a concentration of at least 1.2 ng/ml of OPN protein is indicative that the individual has suffered a stroke as a result of LVO. Preferably, a concentration of at least 1.4 ng/ml of OPN protein is indicative that the individual has suffered a stroke as a result of LVO. Preferably, a concentration of at least 1.6 ng/ml of OPN protein is indicative that the individual has suffered a stroke as a result of LVO. Preferably, a concentration of at least 1.8 ng/ml of OPN protein is indicative that the individual has suffered a stroke as a result of LVO. Preferably, a concentration of at least 2 ng/ml of OPN protein is indicative that the individual has suffered a stroke as a result of LVO. Preferably, a concentration of at least 2.5 ng/ml of OPN protein is indicative that the individual has suffered a stroke as a result of LVO. Preferably, a concentration of at least 5 ng/ml of OPN protein is indicative that the individual has suffered a stroke as a result of LVO.

Preferably, a concentration of at least 100 pg/ml of GFAP protein is indicative that the individual has suffered haemorrhagic stroke. Preferably, a concentration of at least 150 pg/ml of GFAP protein is indicative that the individual has suffered haemorrhagic stroke. Preferably, a concentration of at least 200 pg/ml of GFAP protein is indicative that the individual has suffered haemorrhagic stroke. Preferably, a concentration of at least 250 pg/ml of GFAP protein is indicative that the individual has suffered haemorrhagic stroke. Preferably, a concentration of at least 260 pg/ml of GFAP protein is indicative that the individual has suffered haemorrhagic stroke. Preferably, a concentration of at least 265 pg/ml of GFAP protein is indicative that the individual has suffered haemorrhagic stroke.

Preferably, a concentration of less than 100 pg/ml of GFAP protein is indicative that the individual has suffered non-haemorrhagic stroke. Preferably, a concentration of less than 150 pg/ml of GFAP protein is indicative that the individual has suffered non-haemorrhagic stroke. Preferably, a concentration of less than 200 pg/ml of GFAP protein is indicative that the individual has suffered non-haemorrhagic stroke. Preferably, a concentration of less than 250 pg/ml of GFAP protein is indicative that the individual has suffered non-haemorrhagic stroke. Preferably, a concentration of less than 260 pg/ml of GFAP protein is indicative that the individual has suffered non-haemorrhagic stroke. Preferably, a concentration of less than 265 pg/ml of GFAP protein is indicative that the individual has suffered non-haemorrhagic stroke.

Preferably, a concentration of less than 100 pg/ml of GFAP protein is indicative that the individual has suffered a stroke as a result of LVO. Preferably, a concentration of less than 150 pg/ml of GFAP protein is indicative that the individual has suffered a stroke as a result of LVO. Preferably, a concentration of less than 200 pg/ml of GFAP protein is indicative that the individual has suffered a stroke as a result of LVO. Preferably, a concentration of less than 250 pg/ml of GFAP protein is indicative that the individual has suffered a stroke as a result of LVO. Preferably, a concentration of less than 260 pg/ml of GFAP protein is indicative that the individual has suffered a stroke as a result of LVO. Preferably, a concentration of less than 265 pg/ml of GFAP protein is indicative that the individual has suffered a stroke as a result of LVO.

In some embodiments, one or more of the measured biomarker amount(s) in the sample are transformed into an LVO stroke score. In some embodiments, the LVO stroke score involves correlating the amount of a biomarker in the sample from the individual with one or more of a negative reference, a positive reference, a control or a positive standard. For example, an LVO stroke score from 0 to 100 may be established, where 0 corresponds to the value of the biomarker in a control, and 100 corresponds to the value of the biomarker in a positive standard. A weight factor may be assigned to one or more of the biomarkers. For example, the biomarkers may be weighted such that biomarkers with a higher diagnostic relevance contribute more to the LVO stroke score. For example, a biomarker may be of higher diagnostic relevance if the amount of that biomarker differs significantly between an individual diagnosed as having or having had an LVO and a control. In contrast, a biomarker may be of less diagnostic relevance if the difference in the amount of that biomarker in an individual diagnosed as having or having had an LVO and a control is small. Such weight factors modulate the contribution of the biomarker to the diagnosis of LVO stroke. The weight factor may be introduced in a computational step, for example using an algorithm, or when binding of an agent to the biomarker is detected and measured in a detection tool such as an optical reader.

In some embodiments, the LVO stroke score created using the measured biomarker amounts in a sample taken from an individual identified as or suspected of having or having had a stroke may be compared to an LVO stroke score created using biomarker amounts from a control, or from a positive standard.

In some embodiments, an LVO score created using measured biomarker amounts in a sample taken from the individual identified as or suspected of having or having had a stroke which is comparable to an LVO score created using biomarker amounts from a positive standard is indicative that the individual has suffered a stroke as a result of LVO. In some embodiments, an LVO score created using measured biomarker amounts in a sample taken from the individual identified as or suspected of having or having had a stroke which is statistically comparable to an LVO score created using biomarker amounts from a positive standard is indicative that the individual has suffered a stroke as a result of LVO.

In some embodiments, a difference between an LVO score created using measured biomarker amounts in a sample taken from the individual identified as or suspected of having or having had a stroke and a control is indicative that the individual has suffered an LVO stroke. In some embodiments, a statistically significant difference between an LVO score created using measured biomarker amounts in a sample taken from the individual identified as or suspected of having or having had a stroke and a control is indicative that the individual has suffered an LVO stroke.

In some embodiments, a defined value or range ("cut-off value") is provided for one or more of the biomarkers, and/or for the LVO stroke score. In some such embodiments, an LVO stroke score or an amount of a biomarker above the defined value is indicative that the individual has suffered a stroke resulting from LVO. In other such embodiments, an LVO stroke score, or an amount of a biomarker below the defined value is indicative that the individual has not suffered a stroke resulting from LVO.

In some embodiments, the method may be carried out within about 72, within about 48 or within about 24 hours of the onset of stroke symptoms in the individual. In some embodiments, the method is carried out within about 24 or within 24 hours of the onset of stroke symptoms in the individual. In some embodiments, the method is carried out within about 17 or within 17 hours of the onset of stroke symptoms in the individual. In some embodiments, the method is carried out within about 10 or within 10 hours of the onset of stroke symptoms in the individual. In some embodiments, the method is carried out within about 6 or within 6 hours of the onset of stroke symptoms in the individual.

Preferably, the method is performed on a sample that has been obtained from an individual within about 24 or within 24 hours of the onset of stroke symptoms in the individual. More preferably, the method is performed on a sample that has been obtained from an individual within about 17 or within 17 hours of the onset of stroke symptoms in the individual. Even more preferably, the method is performed on a sample that has been obtained from an individual within about 10 or within 10 hours of the onset of stroke symptoms in the individual. Most preferably, the method is performed on a sample that has been obtained from an individual within about 6 or within 6 hours of the onset of stroke symptoms in the individual.

As shown in FIGS. 9 and 14, combining biomarker expression with a stroke severity score significantly improves the sensitivity and specificity of the method.

Thus, in some embodiments, the method further comprises consideration of data and/or information from one or more clinical assessments the individual has undergone. The clinical assessments may include one or more of CT or CTA, MRA, MRI, diffusion weighted imaging, cerebral angiography, electrocardiogram, atrial fibrillation assessment, FAST (face, arm, speech test), ABCD, ABCD2 and California prediction rules Rosier (Recognition of Stroke in the Emergency Room) stroke scale, stroke scale, and TOAST (trial of ORG. 10172 in Acute Stroke Treatment) classification, OCSP (the Oxford Community Stroke Project classification), National Institutes of Health Stroke Scale (NIHSS), Emergency Medical Stroke Assessment (EMSA), Prehospital Acute Stroke Severity (PASS) scale, Vision, Aphasia, Neglect (VAN) assessment, Rapid Arterial Occlusion Evaluation (RACE), Field Assessment Stroke Triage for Emergency Destination (FAST-ED) scale, Cincinnati pre-hospital Stroke Severity Scale (CPSSS), doppler ultrasound, carotid duplex ultrasound, angiography or arteriography. In some embodiments, the method further comprises consideration of data and/or information from angiographical assessment by CTA and/or MRA. Preferably, the method further comprises determining the stroke severity score of the individual. Preferably the stroke severity score is selected from NIHSS, FAST, FAST-ED, RACE, C-STAT and EMSA. Such scores are well known in the art and the methods by which the scores are calculated would be known to those skilled in the art.

Preferably, a NIHSS score of one or more is indicative that the individual has suffered a stroke as a result of LVO.

Preferably, a FAST score of 1 or more is indicative that the individual has suffered a stroke as a result of LVO.

Preferably, a FAST-ED score of 1, 2, 3, 4 or 5 or more is indicative that the individual has suffered a stroke as a result of LVO. Preferably, a FAST-ED score of 2 or more is indicative that the individual has suffered a stroke as a result of LVO. More preferably, a FAST-ED score of 3 or more is indicative that the individual has suffered a stroke as a result of LVO. More preferably, a FAST-ED score of 4 or more is indicative that the individual has suffered a stroke as a result of LVO. More preferably, a FAST-ED score of 5 or more is indicative that the individual has suffered a stroke as a result of LVO.

Preferably, a RACE score of 1, 2, 3, 4, 5, 6 or 7 or more is indicative that the individual has suffered a stroke as a result of LVO. Preferably, a RACE score of 1 or more is indicative that the individual has suffered a stroke as a result of LVO. Preferably, a RACE score of 2 or more is indicative that the individual has suffered a stroke as a result of LVO. Preferably, a RACE score of 3 or more is indicative that the individual has suffered a stroke as a result of LVO. Preferably, a RACE score of 3 or more is indicative that the individual has suffered a stroke as a result of LVO. Preferably, a RACE score of 4 or more is indicative that the individual has suffered a stroke as a result of LVO. Preferably, a RACE score of 5 or more is indicative that the individual has suffered a stroke as a result of LVO. Preferably, a RACE score of 6 or more is indicative that the individual has suffered a stroke as a result of LVO. Preferably, a RACE score of 7 or more is indicative that the individual has suffered a stroke as a result of LVO.

Preferably, a C-STAT score of 1 or more is indicative that the individual has suffered a stroke as a result of LVO. Preferably, a C-STAT score of 2 or more is indicative that the individual has suffered a stroke as a result of LVO.

Preferably, an EMSA score of 3, 4 or 5 or more is indicative that the individual has suffered a stroke as a result of LVO. Preferably, an EMSA score of 3 or more is indicative that the individual has suffered a stroke as a result of LVO. Preferably, an EMSA score of 4 or more is indicative that the individual has suffered a stroke as a result of LVO. Preferably, an EMSA score of 5 or more is indicative that the individual has suffered a stroke as a result of LVO.

Preferably, the stroke severity score is NIHSS. Preferably, the stroke severity score is FAST. Preferably, the stroke severity score is FAST-ED. Preferably, the stroke severity score is RACE. Preferably, the stroke severity score is C-STAT. Preferably, the stroke severity score is EMSA.

Most preferably, the stroke severity score is FAST, FAST-ED or EMSA.

In a most preferred embodiment, the biomarkers are D-dimer and GFAP and the stroke severity score is FAST, FAST-ED or EMSA.

Preferably, the method comprises combining the amount of one or more biomarkers measured in the sample taken from an individual identified as or suspected of having or having had a stroke and a stroke severity score obtained from the individual.

Preferably, the method further comprises combining the amount of one or more biomarkers measured in the sample taken from an individual identified as or suspected of having or having had a stroke and a stroke severity score obtained from the individual, to produce an LVO stoke score.

Preferably, the method comprises comparing the LVO stroke score created using the measured biomarker amounts in a sample taken from an individual identified as or suspected of having or having had a stroke and the stroke severity score taken from an individual identified as or suspected of having or having had a stroke, to an LVO stroke score created using biomarker amounts and stroke severity scores from a control, or from a positive standard.

Preferably, the individual is diagnosed as having or having had a stroke as a result of LVO when the LVO stroke severity score created using the measured biomarker amounts in a sample taken from an individual identified as or suspected of having or having had a stroke and the LVO stroke score taken from an individual identified as or suspected of having or having had a stroke, is comparable to a positive standard; or when the LVO stroke severity score created using the measured biomarker amounts in a sample taken from an individual identified as or suspected of having or having had a stroke and the LVO stroke severity score taken from an individual identified as or suspected of having or having had a stroke, differs from the LVO stroke score created using biomarker amounts and stroke severity scores from a control.

The LVO stroke score may be calculated by processing the amount of one or more biomarkers and the stroke severity score obtained from the individual using linear regression, random forest, neural networks, support vector machines, Bayesian regression, Bayesian logistic regression or partial least square regression.

Preferably, the LVO stroke score is calculated by processing the amount of one or more biomarkers and the stroke severity score obtained from the individual using a regression model, preferably a multivariate logistic regression model.

Preferably, the LVO stroke score is determined by solving the following equation:

$$Y=a*X_1,b*X_2, \ldots ,n*X_n$$

Where a, b, . . . n indicate the multiplication coefficient of each biomarker or stroke severity score, while $X_1, X_2 \ldots X_n$ indicate the values of biomarkers or stroke severity score measured or obtained from a patient.

Preferably, the multiplication coefficients for each measured biomarker or stroke severity score are as recited in FIG. 13.

The LVO stroke score may be obtained by transforming the value of Y obtained by solving the above equation, for each patient, with a logistic transformation which will be known by anyone skilled in the art.

Thus, preferably, the LVO stroke score is calculated by solving a linear equation based on the coefficients recited in FIG. 17 and the measurements of each corresponding biomarker and stroke severity score collected for any given suspected stroke patient.

In one embodiment, the LVO stroke score may have values between 0 and 1 for any subject. The threshold value of LVO stroke score that may be used to diagnose LVO patients may vary according to which combination of biomarkers and stroke severity scale is chosen. Preferably, the threshold value of LVO stroke score that is used to diagnose LVO patients is chosen among the values recited in FIG. 14.

Preferably, an LVO stroke score greater than 0.20 is indicative of an individual suffering from LVO stroke Preferably, an LVO stroke score greater than 0.24 is indicative of an individual suffering from LVO stroke. Preferably, an LVO stroke score greater than 0.30 is indicative of an individual suffering from LVO stroke. Preferably, an LVO stroke score greater than 0.31, 0.32, 0.33, 0.34, 0.35, 0.36, 0.37, 0.38, 0.39 or 0.40 is indicative of an individual suffering from LVO stroke.

More preferably, an LVO stroke score of greater than 0.33 is indicative of an individual suffering from LVO stroke. More preferably, an LVO stroke score of greater than 0.34 is indicative of an individual suffering from LVO stroke. More preferably, an LVO stroke score of greater than 0.35 is indicative of an individual suffering from LVO stroke. Most preferably, an LVO stroke score of greater than 0.39 is indicative of an individual suffering from LVO stroke.

CTA is a computer-reconstructed tomography technique used to visualise arterial and venous vessel at the level of the head, neck, and/or brain. By applying a contrast agent, CTA allows the visualisation of blockages, aneurysms, dissections and stenosis of blood vessels. Contrast agents are any radiodense compounds that can block the X-ray portion of the electromagnetic spectrum, therefore resulting into opacity areas of the computed images.

MRA refers to any magnetic resonance imaging-based diagnostic technique used to generate images of blood vessels to visualise blockages, aneurysms, dissections and stenosis of blood vessels. Contrast agents, such as the ones based on gadolinium are applied to generate the images and a variety of different techniques are available (Johnson et al "Magnetic resonance angiography: A review." Academic radiology 5, no. 4 (1998): 289-305.)

Identification of an individual who is suffering or has suffered a stroke as a result of LVO allows selection of appropriate further clinical investigations and or a treatment pathway for that individual.

Accordingly in a second aspect there is provided a method of identifying, from a group of individuals identified as or suspected of having or having had a stroke, individuals who have suffered a stroke as a result of LVO, comprising determining the amount of at least two biomarkers in a sample taken from each individual wherein the biomarkers are selected from: succinate, succinic-glutathione, N-acetyl-aspartate, propionyl-carnitine, glutamate, heart fatty acid binding protein (H-FABP), brain fatty acid binding protein (B-FABP), Abeta 1-40, osteoprotegerin (OPG), soluble tumor necrosis factor-like weak inducer of apoptosis (sTWEAK), pro-vWF, retinol binding protein 4 (RBP4), ADAMTS13, NMDA receptor 2 peptide (NR2 peptide), 20-HETE, bilirubin, brain natriuretic peptide (BNP), glial fibrillary acidic protein (GFAP), D-dimer, C-reactive Protein (CRP), matrix metallo-proteinase 9 (MMP9), interleukin 6 (IL-6), osteopontin (OPN), Troponin I, s100b, von Willebrand Factor (vWF), or P-selectin.

However, preferably, the method of the second aspect comprises determining the amount of at least one of the biomarkers selected from: D-dimer, OPN and OPG. More preferably, the method comprises determining the amount of at least two of the biomarkers selected from: D-dimer, OPN and OPG. Most preferably, the method comprises determining the amount of D-dimer, OPN and OPG. Preferably, the method of the second aspect comprises determining the amount of at least one of the biomarkers selected from: D-dimer, OPN, GFAP and OPG. More preferably, the method comprises determining the amount of at least two of the biomarkers selected from: D-dimer, OPN, GFAP and OPG. Most preferably, the method comprises determining the amount of D-dimer, OPN, GFAP and OPG.

Therefore, preferably the biomarkers, determining the amount and concentration of biomarkers may be as defined in the first aspect.

The method may be performed in vivo, in vitro or ex vivo. Preferably, the method is performed in vitro or ex vivo. Most preferably, the method is performed in vitro.

The biomarkers may be detected using any method disclosed herein. In addition, the amount of biomarker may be determined using any method disclosed herein.

In some embodiments the method according to the second aspect comprises determining the amount of at least three, at least four, at least five, at least six, at least seven, at least eight, at least nine, at least 10, at least eleven, or 12 or more biomarkers.

The method according to the second aspect comprises determining the presence and/or amount of one or more biomarkers in accordance with any embodiment of the first aspect.

In some embodiments according to the second aspect the method comprises comparing the amount of each biomarker in the sample taken from each individual identified as or suspected of having or having had a stroke to the amount of the same biomarker in one or more of a control, a positive standard, one or more positive references or a negative reference, as disclosed in accordance with the first aspect, above.

In some embodiments according to the second aspect, individuals with a difference in the amount of one or more of the measured biomarker relative to the amount of the same biomarker in a control are identified as having or having had a stroke as a result of LVO. In some embodiments according to the second aspect, individuals with a comparable amount of one or more of the measured biomarker relative to a positive standard are identified as having or having had a stroke as a result of LVO.

In some embodiments the method comprises transforming the amount of one or more biomarkers measured in the sample taken from an individual identified as or suspected of having or having had a stroke into an LVO stroke score, as disclosed in accordance with the first aspect, above.

In some embodiments according to the second aspect, individuals with an LVO score comparable to an LVO score created using biomarker amounts from a positive standard are identified as having or having had a stroke as a result of LVO. In some embodiments, individuals with an LVO score statistically comparable to an LVO score created using biomarker amounts from a positive standard are identified as having or having had a stroke as a result of LVO. In some embodiments, individuals with an LVO score that differs from an LVO score created using biomarker amounts from a control are identified as having or having had a stroke as a result of LVO. In some embodiments, individuals with an LVO score that is statistically different from an LVO score created using biomarker amounts from a control are identified as having or having had a stroke as a result of LVO.

In some embodiments the method according to the second aspect further comprises determining the stroke severity score of the individual as defined in the first aspect. In some embodiments the method according to the second aspect combining the amount of one or more biomarkers measured in the sample taken from an individual identified as or suspected of having or having had a stroke and a stroke severity score obtained from the individual, as defined in the first aspect.

In some embodiments the method according to the second aspect further comprises consideration of data and/or information from one or more clinical assessments which each individual has undergone, as disclosed in accordance with the first aspect, above. In some such embodiments the clinical assessment is one or more of a CT or CTA, MRA or MRI scan, or the individual's NIHSS, FAST, ABCD, ABCD2 Rosier, TOAST, EMSA, PASS, VAN, RACE, FAST-ED or CPSS score.

Appropriate further clinical investigations for an individual who is identified as suffering from or has suffered a stroke as a result of LVO include computerised tomography angiography and/or magnetic resonance angiography. Appropriate treatment pathways for an individual who is identified as suffering from or has suffered a stroke as a result of LVO may include treatment with antithrombotic agents and/or mechanical thrombectomy.

In accordance with a third aspect, there is provided the use of two or more biomarkers to diagnose stroke resulting from large vessel occlusion, wherein the biomarkers are selected from succinate, succinic-glutathione, N-acetyl-aspartate, propionyl-carnitine, glutamate, heart fatty acid binding protein (H-FABP), brain fatty acid binding protein (B-FABP), Abeta 1-40, osteoprotegerin (OPG), soluble tumor necrosis factor-like weak inducer of apoptosis (sTWEAK), pro-vWF, retinol binding protein 4 (RBP4), ADAMTS13, NMDA receptor 2 peptide (NR2 peptide), 20-HETE, bilirubin, brain natriuretic peptide (BNP), glial fibrillary acidic protein (GFAP), D-dimer, C-reactive Protein (CRP), matrix metalloproteinase 9 (MMP9), interleukin 6 (IL-6), osteopontin (OPN), Troponin I, s100b, von Willebrand Factor (vWF), or P-selectin.

The biomarkers and concentration biomarkers may be as defined in the first aspect.

In some embodiments, at least three, at least four, at least five, at least six, at least seven, at least eight, at least nine, at least 10, at least eleven, or 12 or more biomarkers are used to identify stroke resulting from large vessel occlusion.

In some embodiments, the biomarkers are in a sample taken from an individual identified as or suspected of having or having had a stroke. The biomarkers may be detected using any method disclosed herein. In addition, the amount of biomarker may be determined using any method disclosed herein.

As described in the Examples and above, the inventors have identified biomarkers that can be used to diagnose stroke as a result of a LVO with a high degree of sensitivity and specificity.

Accordingly, in a fourth aspect of the invention there is provided D-dimer, OPN, OPG and/or GFAP, for use in diagnosing stroke as a result of a large vessel occlusion (LVO).

In one embodiment, there is provided D-dimer, for use in diagnosing stroke as a result of a large vessel occlusion (LVO). In one embodiment, there is provided OPN, for use in diagnosing stroke as a result of a large vessel occlusion (LVO). In one embodiment, there is provided OPN, for use in diagnosing stroke as a result of a large vessel occlusion (LVO). In one embodiment, there is provided GFAP, for use in diagnosing stroke as a result of a large vessel occlusion (LVO). In one embodiment, there is provided D-dimer and GFAP, for use in diagnosing stroke as a result of a large vessel occlusion (LVO).

In one embodiment, there is provided D-dimer, OPN and OPG, for use in diagnosing stroke as a result of a large vessel occlusion (LVO).

The biomarkers may be detected using any method disclosed herein. In addition, the amount of biomarkers may be determined using any method disclosed herein.

Preferably, the biomarkers, determining the amount, the concentration of biomarkers associated with stroke as a result of a LVO and the sample are as defined in the first aspect.

In a fifth aspect of the invention, there is provided GFAP, for use in diagnosing haemorrhagic stroke.

Preferably, GFAP, determining the amount, the concentration of associated with stroke as a result of a LVO and the sample are as defined in the first aspect.

There is also provided, in a sixth aspect, a kit for carrying out a method according to the first, second and third aspects of the invention. The kit may comprise one or more of: a container for holding a sample from the individual identified or suspected as having or having had a stroke; a means for determining the amount of the target biomarker(s); and instructions, such as printed instructions on how to carry out the reaction between the sample and the means provided so as to determine the amount of the target biomarker(s).

In some embodiments, the means for determining the amount of the target biomarker(s) may comprise one or more agents as disclosed herein. The agent(s) may be antibodies. The agents may be immobilised on a substrate and/or may be labelled with at least one detectable label. In some embodiments each agent is labelled with a different detectable label.

The methods according to the invention enable patients suffering from stroke resulting from LVO to be quickly and easily identified and the appropriate treatment option selected.

Accordingly, in an seventh aspect there is provided a method of treating an individual suffering from stroke as a result of a large vessel occlusion (LVO), the method comprising:

a) determining the amount of at least one biomarker in a sample taken from each individual wherein the biomarkers are selected from: osteoprotegerin (OPG), glial fibrillary acidic protein (GFAP), D-dimer and osteopontin (OPN), wherein the amount of biomarker suggest that the individual is suffering from stroke as a result of a large vessel occlusion (LVO; and
b) administering, or having administered, to the individual, a therapeutic agent that treats stroke as a result of a large vessel occlusion (LVO).

The biomarkers may be detected using any method disclosed herein. In addition, the amount of biomarker may be determined using any method disclosed herein. Preferably, the biomarkers, determining the amount of biomarkers, concentrations of biomarkers associated with stroke as a result of a LVO and sample are as defined in the first aspect.

Preferably, the treatment comprises mechanical thrombectomy (MT) and/or intravenous or intraarterial thrombolytic treatment.

Without wishing to be bound by any theory, it is suggested that the accuracy of detection of stroke resulting from LVO in methods according to the invention arises as a result of the detection of certain amounts of specific biomarkers or a specific combination of biomarkers in a sample from an individual suspected of having or having had a stroke, levels of which are altered as a result of biological changes that occur as a result of LVO stroke. It is suggested that such markers are associated with brain ischemia and/or death of brain cells, both of which are increased in LVO in comparison to other types of stroke. Ischemia can result in damage to tissue and cells resulting in release and/or upregulation of biomarkers either from the damaged cells or tissues themselves, or from tissues or cells in communication with injured cells.

Accordingly, some embodiments of the invention provide methods, kits and uses for identifying or helping to identify those individuals presenting with stroke who are or have suffered a stroke resulting from LVO. Such embodiments offer the opportunity to allow determination of such individuals with improved accuracy and/or speed, thereby improving the treatment pathway for the individual.

It will be appreciated that the invention extends to any nucleic acid or peptide or variant, derivative or analogue thereof, which comprises substantially the amino acid or nucleic acid sequences of any of the sequences referred to herein, including variants or fragments thereof. The terms "substantially the amino acid/nucleotide/peptide sequence", "variant" and "fragment", can be a sequence that has at least 40% sequence identity with the amino acid/nucleotide/peptide sequences of any one of the sequences referred to herein, for example 40% identity with the sequence identified as SEQ ID Nos: 1 to 8 and so on.

Amino acid/polynucleotide/polypeptide sequences with a sequence identity which is greater than 65%, more preferably greater than 70%, even more preferably greater than 75%, and still more preferably greater than 80% sequence identity to any of the sequences referred to are also envisaged. Preferably, the amino acid/polynucleotide/polypeptide sequence has at least 85% identity with any of the sequences referred to, more preferably at least 90% identity, even more preferably at least 92% identity, even more preferably at least 95% identity, even more preferably at least 97% identity, even more preferably at least 98% identity and, most preferably at least 99% identity with any of the sequences referred to herein.

The skilled technician will appreciate how to calculate the percentage identity between two amino acid/polynucleotide/polypeptide sequences. In order to calculate the percentage identity between two amino acid/polynucleotide/polypeptide sequences, an alignment of the two sequences must first be prepared, followed by calculation of the sequence identity value. The percentage identity for two sequences may take different values depending on: —(i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (e.g. BLOSUM62, PAM250, Gonnet etc.), and gap-penalty, e.g. functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (v) the number of equivalenced positions excluding overhangs. Furthermore, it will be appreciated that percentage identity is also strongly length dependent. Therefore, the shorter a pair of sequences is, the higher the sequence identity one may expect to occur by chance.

Hence, it will be appreciated that the accurate alignment of protein or DNA sequences is a complex process. The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention.

Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: ENDGAP=−1, and GAPDIST=4. Those skilled in the art will be aware that it may be necessary to vary these and other parameters for optimal sequence alignment.

Preferably, calculation of percentage identities between two amino acid/polynucleotide/polypeptide sequences may then be calculated from such an alignment as (N/T)*100, where N is the number of positions at which the sequences share an identical residue, and T is the total number of positions compared including gaps and either including or excluding overhangs. Preferably, overhangs are included in the calculation. Hence, a most preferred method for calculating percentage identity between two sequences comprises (i) preparing a sequence alignment using the ClustalW program using a suitable set of parameters, for example, as set out above; and (ii) inserting the values of N and T into the following formula: —Sequence Identity=(N/T)*100.

Alternative methods for identifying similar sequences will be known to those skilled in the art. For example, a substantially similar nucleotide sequence will be encoded by a sequence which hybridizes to DNA sequences or their complements under stringent conditions. By stringent conditions, the inventors mean the nucleotide hybridises to filter-bound DNA or RNA in 3× sodium chloride/sodium citrate (SSC) at approximately 45° C. followed by at least one wash in 0.2×SSC/0.1% SDS at approximately 20-65° C.

Alternatively, a substantially similar polypeptide may differ by at least 1, but less than 5, 10, 20, 50 or 100 amino acids from the sequences shown in, for example, SEQ ID Nos: 1 to 8.

Due to the degeneracy of the genetic code, it is clear that any nucleic acid sequence described herein could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent (synonymous) change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example, small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will know the nucleotide sequences encoding these amino acids.

All of the features described herein (including any accompanying claims, abstract and drawings), and/or all of the steps of any method or process so disclosed, may be combined with any of the above aspects in any combination, except combinations where at least some of such features and/or steps are mutually exclusive.

The following examples are provided to illustrate the present invention and should not be construed as limiting thereof.

For a better understanding of the invention, and to show how embodiments of the same may be carried into effect, reference will now be made, by way of example, to the accompanying Figures, in which:

BRIEF DESCRIPTION OF THE DRAWINGS

FIG. 1 shows univariate analysis of 44 clinical variables in LVO and non-LVO stroke patients. Each variable was analysed based on distribution normality. For normally distributed variables, mean and standard deviation (SD) are reported. For not normally distributed variables, median and interquartile range (IQR) are reported. P-values were obtained from Student's t (normally distributed continuous variables) Wilcoxon/Mann-Whitney (not normally distributed continuous variables), or Chi-square test (categorical variables), and were adjusted for multiple comparisons with Benjamini-Hochberg's method. NIHSS: national institute of health stroke severity. SBP: systolic blood pressure. APTT: activated partial thromboplastin time. PT: prothrombin time. DBP: diastolic blood pressure. RBC: red blood cells. CRP: C-reactive protein. NLR: neutrophil-to-lymphocyte ratio. OBT: stroke onset to blood collection time. MCV: mean corpuscular volume. MCH: mean corpuscular haemoglobin. WBC: white blood cells. * and *** indicate p-values <0.05 and 0.001, respectively.

FIG. 4 shows the diagnostic performance of logistic models built on single biomarkers D-dimer, OPN and OPG. Concentration cut-off values estimated with ROC curve analysis are reported for each biomarker model. Values of diagnostic performance measures are shown, whit 95% confidence interval reported in brackets. P-values were calculated using Fisher's exact test on the contingency matrix of each model. LR+: positive likelihood ratio; LR−: negative likelihood ratio; OR: odds ratio.

FIG. 5 shows a comparison of a multivariable logistic model built on D-dimer, OPN, and OPG, and a multivariable logistic model built on GFAP, OPN, OPG, and D-dimer. The two models are compared with the Akaike Information Criteorion (AIC), model deviance, Area Under the receiving operating characteristic Curve (AUC), and likelihood ratio (LR) test. Df=degree of freedome of the LR test. P-value <0.05 is considered significant.

FIG. 8 shows univariate and multivariable regression models for LVO prediction for biomarkers D-dimer and GFAP, stroke scores and combinations of biomarkers with stroke scores. Multivariable analysis found that the optimal set of blood biomarkers for LVO prediction was D-dimer (OR 15.44, 95% CI 4.91 to 57.6; p-value<0.0011) and GFAP (OR 0.83, 95% CI 0.5 to 0.99; p-value=0.03).

FIG. 9 shows a summary of the logistic regression models of each scale alone, or with added biomarkers, which are compared for their accuracy in predicting LVO by estimating the area under the receiver operating characteristic curve (AUC), presented with 95% CIs. To assess the value added by including blood biomarkers with each stroke scale in predicting LVO, LR test was performed comparing the model with each stroke scale alone and the model with addition of biomarkers. The addition of D-dimer and GFAP resulted in improved goodness of fit (i.e. lower AIC), LVO prediction (i.e. higher AUC), and significant LR test for each stroke scale tested, compared to using the stroke scales alone. The combination of D-dimer and GFAP with FAST-ED or EMSA resulted in the highest LR+ for LVO prediction (22.6, 95% CI 8.58 to 59.51 and 17.22, 95% CI 7.22 to 41.04, respectively), with LR− of 0.09 (95% CI 0.02 to 0.34) or 0.14 (95% CI 0.05 to 0.39), sensitivity of 91% (95% CI 71 to 98) or 86 (95% CI 66 to 97), and specificity of 95% (95% CI 89 to 98) or 94% (95% CI 88 to 98), respectively. LR p-values refer to the comparison between the model with a stroke scale alone and the corresponding model with the addition of biomarkers.

FIG. 11 shows a summary of plasma concentrations of D-dimer, OPN, OPG, vWF, ADAMTS13, and GFAP in the plasma of LVO and non-LVO patients. The inventors found statistically significant differences for the following blood biomarkers: D-dimer (1.31±2.0 and 0.42±0.45 μg/mL respectively, p-value <0.001); OPN (1.71±1.05 and 1.16±1.09 ng/mL respectively, p-value <0.01); OPG (125.24±60.96 and 97.96±54.29 pg/mL respectively, p-value <0.01). Median values are reported (pg/mL), with IQR values shown in brackets. Wilcoxon-Mann Whitney p-values are shown.

FIG. 12 provides a summary of the evaluation of stroke severity scales in LVO and non-LVO patients. Median values of stroke severity scales obtained for all patients, LVO, and non-LVO patients. IQR values shown in brackets. Wilcoxon-Mann Whitney was used to calculate p-values.

FIG. 13 shows the equation coefficients associated to each biomarker and stroke severity score, when used in different combinations (i.e. model). While every model always has an "Intercept" coefficient, the coefficient of each biomarker will depend on weather that biomarker is included in the model. Preferably, the reported coefficients are to be used when calculating the LVO stroke score.

FIG. 14 summarises the measures of sensitivity, specificity, positive likelihood ratio (LR+), and negative likelihood ratio (LR−) for various combination of the biomarkers with stroke scores. For each model, the cut-off point was selected by maximising specificity for LVO prediction while maintaining a minimum specificity level of 90%, in line with power analysis. Correction for optimistic predictions was performed through bootstrapping with 2000 resamples and presented with CIs. The combination of D-dimer and GFAP with FAST-ED or EMSA resulted in the highest LR+ for LVO prediction (22.6, 95% CI 8.58 to 59.51 and 17.22, 95% CI 7.22 to 41.04, respectively), with LR− of 0.09 (95% CI 0.02 to 0.34) or 0.14 (95% CI 0.05 to 0.39), sensitivity of 91% (95% CI 71 to 98) or 86 (95% CI 66 to 97), and specificity of 95% (95% CI 89 to 98) or 94% (95% CI 88 to 98), respectively.

EXAMPLE 1

Example 1A: Sample Preparation

Figure 2A:
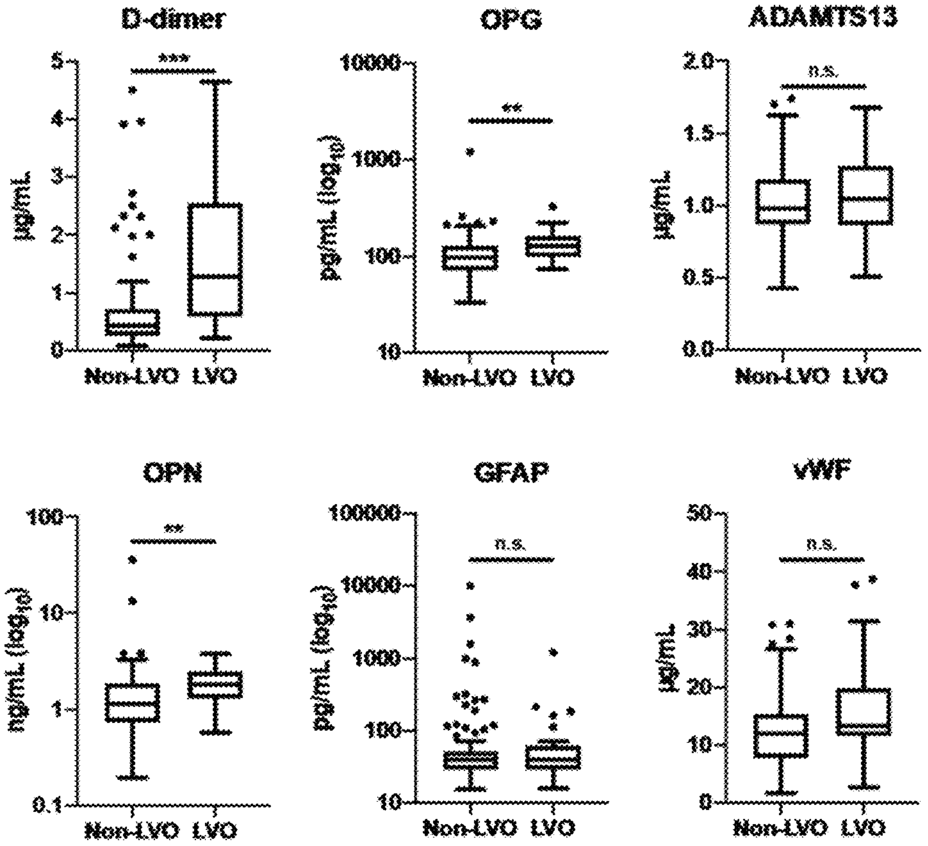
FIG. 2A shows plasma concentrations of blood biomarkers measured in LVO and non-LVO stroke patients.

A sample of blood may be withdrawn via venipuncture from a human subject and collected into tubes containing sodium EDTA and immediately placed on ice. Alternatively, a sample of CSF may be obtained by lumbar puncture.

The need for and type of processing of the sample prior to biomarker detection depends upon the biomarker to be detected and/or the assay to be used to detect the biomarker. Where whole blood is required for analysis, the sample can be used as obtained. Alternatively, the sample can be diluted with saline solution to obtain an appropriate concentration of biomarkers that are compatible with the required type of biomarker detection assay.

If blood plasma is required for analysis, the whole blood sample can be centrifuged to obtain the plasma, for example at 2000 g for 15 minutes at 4° C. The plasma can then be drawn off and used directly, or diluted with saline solution as required for the biomarker detection assay.

Example 1b: Optimisation of the Assay

Rabbit monoclonal antibodies are purchased from Abcam, Cambridge UK. A known concentration of isolated or recombinant antibody is applied in a preliminary assay to determine the specificity of antibodies to recognise and bind the target biomarker. To determine optimal concentration of the antibodies an indirect ELISA is performed wherein the isolated or recombinant biomarker protein is attached to an ELISA microtiter plate. Rabbit monoclonal anti-human biomarker antibody is coated to the microtiter plate to determine the concentration of antibody necessary to obtain a maximum signal, allowing determination of the lower limit of detection of indirect ELISA for each antibody. After incubation of a diluted sample with a rabbit monoclonal antihuman biomarker antibody for 2 hours, and appropriate wash is performed, a monoclonal anti-human biomarker antibody labelled with biotin is then added and incubated with captured biomarker. Multiple steps of washing are then performed, after which horseradish peroxidase conjugated with streptavidin is added. Incubation of the reagents for one hour is then followed by other washing steps, after which the generated conjugate is contacted with hydrogen peroxide tetramethyl benzadine, producing a yellow product. The reaction is stopped by adding acidic solution and reaction signal mis-measured by absorbance at 450 nanometers, with the absorbance being proportional to the concentration of the biomarker. By plotting absorbance values as a function of measured biomarker quantities in samples at known biomarker concentrations a standard curve is obtained. The standard curve is then used to determine the quantity of target biomarker in unknown samples.

Example 1C: Materials for Biomarker Analyses

Illustrative reagents used in performing the subject invention include Sodium bicarbonate (Sigma Cat #: C-3041), blocking buffer (Startingblock T20-TBS) (Pierce Cat #: 37543), Tris buffered saline with Tween 20 (TBST; Sigma Cat #: T-9039). Phosphate buffered saline (PBS; Sigma Cat #: P-3813); Tween 20 (Sigma Cat #: P5927); Ultra TMB ELISA (Pierce Cat #: 34028); and Nunc maxisorp ELISA plates (Fisher). Monoclonal and polyclonal antibodies against heart fatty acid binding protein (H-FABP), brain fatty acid binding protein (B-FABP), Abeta 1-40, OPG, soluble tumor necrosis factor-like weak inducer of apoptosis (sTWEAK), pro-vWF, retinol binding protein 4 (RBP4), ADAMTS13, NMDA receptor 2 peptide (NR2 peptide), 20-HETE, brain natriuretic peptide (BNP), glial fibrillary acidic protein (GFAP), D-dimer, C-reactive Protein (CRP), matrix metallo-proteinase 9 (MMP9), interleukin 6 (IL-6), osteopontin (OPN), Troponin I, s100b, von Willebrand Factor (vWF), P-selectin are purchased from Abcam, Cambridge, UK. Labels for antibodies of numerous subtypes are available from Expedeon Ltd, Cambridge, UK. Protein concentrations in samples are determined using bicinchoninic acid microprotein assays (Pierce Inc., Rockford, Ill., USA) with albumin standards. All other necessary reagents and materials will be known to those of skill in the art and are readily ascertainable. Colorimetric assay kits for bilirubin, succinate, N-acetylaspartate, Propionyl-L-carnitine, glutamate are available from Abcam, Cambridge, UK and Biovision Inc, Milpitas, Calif.

Example 2

Methods

Patient Recruitment and Sample Processing

Suspected stroke patients within 18 hours "since last known well" were recruited retrospectively after their arrival to the emergency department (ED) of the Freeman hospital and of the Royal Victoria Infirmary hospital at Newcastle upon-Tyne (UK).

One 4 mL sample of venous blood was withdrawn within 30 minutes from arrival, and immediately stored at +4° C. in the dark until processing. Blood plasma was obtained by centrifugation of whole blood at 2000×g for 15 minutes at +4° C. After processing, plasma samples were immediately frozen at −80° C. until biomarker measurement.

Adjudication of Diagnosis 170 patients with suspected stroke were identified by ambulance paramedics and ED clinicians. Adjudication of stroke subtype, stroke mimic, or TIA diagnosis was based on brain imaging results and neurologist report. Diagnosis of haemorrhagic stroke was based on results from computerised tomography (CT) brain scan, while adjudication of stroke mimic or transient ischaemic attack (TIA) was based on neurologist report. Ischaemic stroke patients were subdivided into 3 categories, based on neurologist report, CT angiography (CTA) imaging, and NIHSS score. Ischemic stroke patients labelled as "unknown" were excluded from subsequent analysis due to uncertainty of diagnosis. Exclusion of 23 "unknown" ischemic stroke and utilisation of 19 samples for immunoassay testing, led to a final patient cohort of 128 suspected stroke patients that were submitted to biomarker measurement and statistical analysis.

Derivation of Pre-Hospital Stroke Scales from NIHSS Score

FAST score was calculated by assigning 1 point for any presence of facial paresis (NIHSS item 4), 1 point for any arm weakness (NIHSS item 5a/b), and 1 point for any speech impairment (NIHSS item 9). FAST-ED was calculated as described by Lima et al[5], RACE score was calculated as described by Perez de la Ossa[7], CPSS was calculated as described by Katz et al[19], and EMSA was calculated as described by Gropen et al[10].

Measurement of Blood Biomarkers

Plasma biomarkers were measured with commercial enzyme-linked immunosorbent assays (ELISA) following manufacturer's instructions. ELISA kits or matched antibody pairs were purchased from Abcam (Cambridge, UK): D-dimer (product number: ab196269), OPN (product number: ab100618), OPG (product number: ab100617), GFAP (product number: ab222279), vWF (product number: ab223864), and ADAMTS13 (product number: ab234559). Plasma sample dilutions for detection of each biomarker were as follows: D-dimer (1:80), OPN (1:2), OPG (1:6), GFAP (1:2), vWF (1:4000), ADAMTS13 (1:800). Samples were diluted in dilution buffers as described by manufacturer's instructions. All samples were analysed in duplicate and the mean value was used for quantification. For all biomarkers, the average coefficient of variation was <10%. Biomarker quantification was performed by linear or second order polynomial interpolation against calibration curves obtained with known concentrations of each analyte. GraphPad Prism version 8.4.3 was used for biomarker quantification.

Statistical Analysis

For univariate analysis of individual blood biomarkers or clinical variables, normality of distributions was assessed by Shapiro-Wilk test. For continuous variables, those normally distributed (Shapiro-Wilk p-value >0.1) were analysed by Student's t-test and mean and standard deviation (SD) values are given, whereas for variables with non-normal distribution Wilcoxon-Mann-Whitney U test was used and median and interquartile range (IQR) are reported. Intergroup differences were assessed by Pearson's chi-square test for categorical variables. When >10 variables were tested at the same time, multiple hypothesis correction was performed with Benjamini-Hochberg method. Analysis of variance was used to assess the interaction between all blood biomarkers and subtypes of suspected stroke. If overall significance was confirmed, pairwise comparisons were performed with Tukey's test.

To identify the optimal panel of blood biomarkers for LVO prediction, we used a multivariate logistic regression with Diagnosis (LVO vs non-LVO) as outcome variable and plasma levels of D-dimer, GFAP, OPN, OPG, vWF, and ADAMTS13 as exploratory variables. Bidirectional stepwise elimination based on Akaike information criterion (AIC) levels was used for model selection. Linearity between predictors and outcome measure was assessed through logarithmic and quadratic transformation. Transformations were selected based on the AIC.

To investigate whether the addition of blood biomarkers improved the accuracy of stroke severity scales for LVO identification, we used a second multivariate logistic with Diagnosis as the outcome variable and the optimal panel and one of the stroke severity scales (FAST, FAST-ED, RACE, C-STAT, or EMSA) as exploratory variables. We used this approach because the scales were highly correlated, and, since a comparison of different severity scales was outside the scope of this work, this approach reduced the level of collinearity in the model.

To assess the goodness of fit of the blood biomarker panel and the stroke scales, the likelihood ratio test (LR) and AIC were used. The area under the receiver operating characteristic curve (AUC) with 95% CIs was used as a measure of discrimination. At selected cut-off points sensitivity, specificity, positive likelihood ratio (LR+), and negative likelihood ratio (LR−) were also evaluated. For each model, the cut-off point was selected by maximising specificity for LVO prediction while maintaining a minimum specificity level of 90%, in line with our power analysis. Correction for optimistic predictions was performed through bootstrapping with 2000 resamples, and presented with confidence intervals (CI).

All analyses were performed with R version 3.6.2 with the help of RStudio version 1.2.5033 by using the packages nnet, ROCR, caret, tidyverse, oddsratio, lmtest, and OptimalCutpoints.

Example 2A: Cohort Description and Clinical Variables Analysis

In this study, the inventors retrospectively recruited 170 patients with suspected stroke. After adjudication of diagnosis (Methods), the inventors obtained a final cohort of 128 suspected stroke patients that was composed of the following stroke subtypes: haemorrhagic stroke (n=16, 12.5%), LVO ischemic stroke (n=23, 18%), non-LVO ischemic strokes (n=42, 33%), stroke mimic (n=31, 24%), transient ischemic attack (n=16, 12.5%). The cohort's median stroke onset-to-blood collection time (OBT) was 158 minutes (IQR=161.5 minutes).

The inventors assessed the difference between LVO and non-LVO patients (including ischemic non-LVO, haemorrhagic, and non-stroke patients) of 42 clinical variables associated with each patient (FIG. 1). After adjustment for multiple hypothesis testing, the inventors found significant differences in NIHSS score (p-value=$7.04^{e-08}$; median LVO vs non-LVO: 18 vs 3; IQR LVO vs non-LVO: 8.5 vs 5), presence of atrial fibrillation (p-value=0.0002; absence/presence LVO vs non-LVO: 11/12 vs 94/11), and systolic blood pressure (p-value=0.033; mean LVO vs non-LVO: 140 vs 157; SD LVO vs non-LVO: 22 vs 29). In our cohort, age and gender were not significantly associated with LVO diagnosis. Of note, we found no differences in the time from stroke onset to blood withdrawal in LVO vs non-LVO patients.

Example 2B: Blood Biomarkers for LVO Identification

The inventors then set out to investigate the levels of a panel of blood proteins in the patient cohort. they measured the levels of D-dimer, osteopontin (OPN), osteoprotegerin (OPG), von-Willebrand factor (vWF), a disintegrin and a metalloproteinase with a thrombospondin type I motif, member 13 (ADAMTS13), and glial fibrillary acidic protein (GFAP) in the plasma of LVO and non-LVO patients (FIGS. 2A, 7 and 11). the inventors found statistically significant differences between LVO and non-LVO patients for the following blood biomarkers: D-dimer (p-value <0.001; mean LVO vs non-LVO: 1.31 vs 0.42 μg/mL; SD LVO vs non-LVO: 2.00 vs 0.45 μg/mL), OPN (p-value <0.01; mean LVO vs non-LVO: 1.71 vs 1.16 ng/mL; SD LVO vs non-LVO: 1.05 vs 1.09 ng/mL), and OPG (p-value <0.01; mean LVO vs non-LVO: 125.24 vs 97.96 pg/mL; SD LVO vs non-LVO: 60.96 vs 54.29 pg/mL). Without wishing to be bound to any specific theory, the inventors believe that this data suggests that, among the biomarkers tested in the panel, D-dimer, OPN, and OPG may help in the identification of LVO strokes.

Figure 2B:
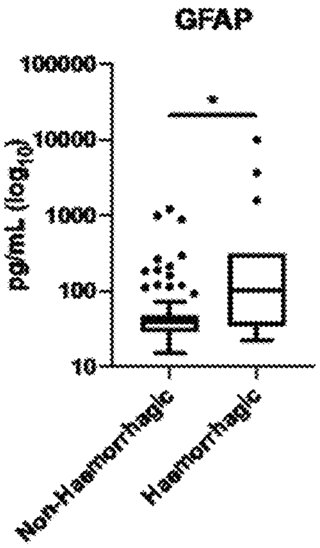
FIG. 2B shows plasma concentrations of GFAP measured in haemorrhagic and non-haemorrhagic stroke patients.  and * indicate Wilcoxon-Mann-Whitney p-value <0.01 and p-value <0.00, respectively; n.s. indicates p-value >0.05.
Figure 3:
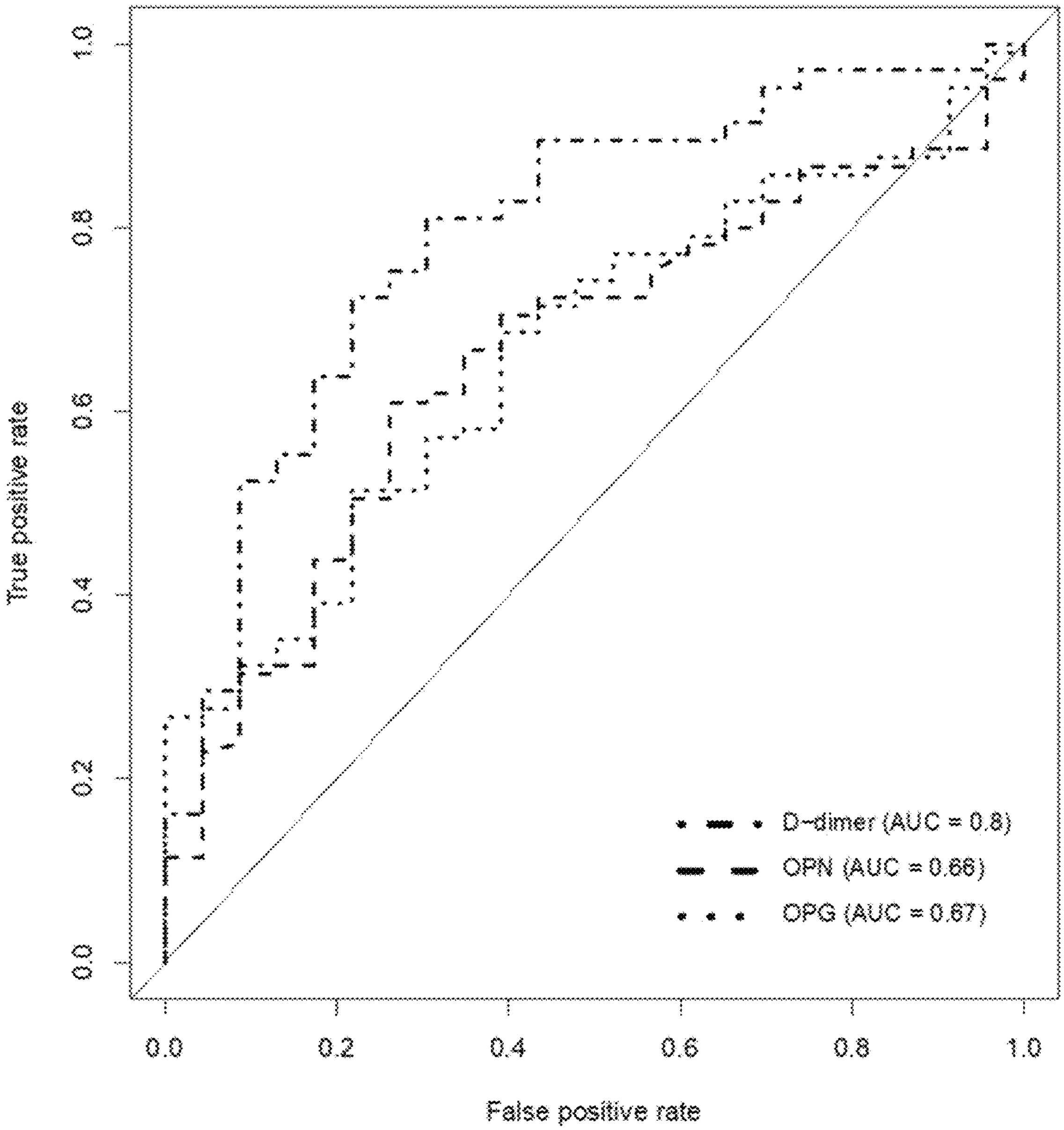
FIG. 3 shows receiver operating characteristic (ROC) curves obtained with individual biomarkers that were found significant in the univariate analysis, for the differentiation between LVO and non-LVO strokes. Area under the ROC curve (AUC) of each logistic model is indicated.

The inventors then built logistic regression models based on the levels of each significant biomarker. They estimated the area under the ROC curve of each model, and found that D-dimer resulted in an AUC of 0.80, while the AUCs associated with OPN and OPG were 0.66 and 0.67, respectively (FIG. 2). With ROC curve analysis we estimated cut-off levels for D-dimer, OPN, and OPG by maximising diagnostic specificity for LVO identification, whilst maintaining a minimum level of sensitivity of 50% (Table 2). All 3 biomarkers achieved >70% specificity for LVO identification, with D-dimer achieving almost 90% specificity (FIG. 4). Notably, D-dimer, OPN, and OPG were independent predictors of LVO status, with OR 10.34 (CI 95%: 4.65-20), 3.05 (CI 95%: 1.48-5.63), and 3.36 (CI 95%: 1.68-6.32), respectively.

GFAP was included in the inventor's panel due to its known association with haemorrhagic stroke[20-22]. In line with this hypothesis, GFAP levels were increased in haemorrhagic strokes, compared to non-haemorrhagic stroke and non-stroke patients (FIG. 1B; p-value=0.007; mean haemorrhagic vs non-haemorrhagic/non-stroke: 1043.46 vs 66.10 pg/mL; SD haemorrhagic vs non-haemorrhagic: 2581.28 vs 127.24 pg/mL). The inventors built a logistic regression model based on GFAP plasma levels, for the identification of haemorrhagic stroke in our cohort. Applying ROC curve analysis, they found that a cut-off value of 265 pg/mL on GFAP levels was able to identify haemorrhagic patients with an accuracy of 88%, a sensitivity of 30%, and a specificity of 96%. Notably, GFAP levels higher than 265 pg/mL were an independent predictor of haemorrhagic stroke in our cohort (OR: 12.27; CI 95%: 2.87-52.52; p-value=0.0015).

The inventor's findings suggest that a biomarker panel composed of OPN, OPG, and D-dimer (OOD) could help in the identification of LVO. The inventors built a logistic model based on the levels of OOD biomarkers and applied ROC curve analysis to estimate the logistic model threshold with highest accuracy for the identification of LVO (FIG. 5). They found that a model threshold of 0.69 was able to identify LVO patients with an accuracy of 83% (CI 95%: 79-88%), sensitivity of 57% (CI 95%: 42-71%), specificity of 90% (CI 95%: 86-93%), positive likelihood ratio of 5.7 (CI 95%: 3.47-9.39), and negative likelihood ratio of 0.48 (CI 95%: 0.32-0.64). Of note, patients scoring with a model value lower than 0.69 had >12 times higher probability to be suffering from LVO stroke, compared to patients with higher model values (OR 12.56; CI 95%: 5.48-27.71). This finding indicates that a biomarker panel composed of OPN, OPG, and D-dimer (OOD) could help in the identification of LVO strokes.

In addition, the inventor's findings suggest that inclusion of GFAP in the biomarker panel could help to rule out haemorrhagic stroke from the population of suspected stroke patients, potentially improving LVO identification. To test this hypothesis, they estimated the LVO diagnostic performance of a biomarker panel composed of GFAP, OPN, OPG, and D-dimer (GOOD), and compared its performance with the OOD model (FIG. 5). Maximisation of accuracy with ROC curve analysis, estimated a logistic model threshold of 0.59 which allowed to identify LVO patients with an accuracy of 86% (CI 95%: 82-90%), sensitivity of 52% (CI 95%: 38-67%), specificity of 94% (CI 95%: 91-97%), positive likelihood ratio of 10.14 (CI 95%: 5.09-21.67), and negative likelihood ratio of 0.51 (CI 95%: 0.35-0.66). Notably, inclusion of GFAP in the OOD panel almost doubled the probability for LVO patients to test positive (OR 21.06; CI 95%: 8.17-50). Application of the logistic model threshold with highest predicted accuracy (cut-off=0.59) identified patients with the following ranges of biomarker levels: GFAP: 17.43-184.27 pg/mL; OPN: 0.71-1.86 ng/mL; OPG: 73.34-205.47 pg/mL; D-dimer: 2.42-4.65 μg/mL.

Figures 6, 7:
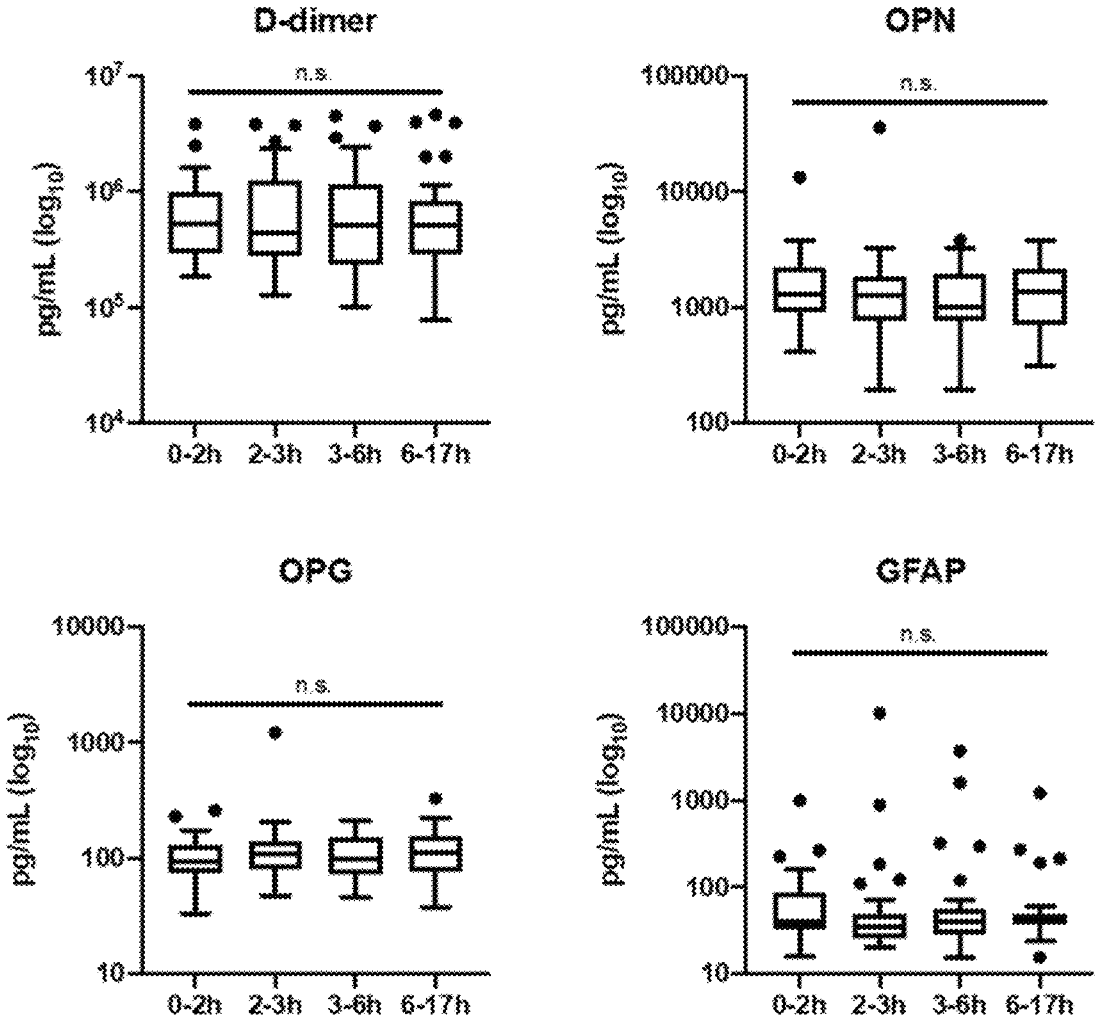
FIG. 6 shows that there was no change in the levels of blood biomarkers according to stroke Onset to Blood collection Time (OBT). The patient cohort was divided into OBT quartiles and differences were assessed with analysis of variance. N.s.=not significant.
FIG. 7 shows univariate regression for LVO prediction. The p-values indicate statistical significance of the covariate in the related model. Levels of D-dimer, OPN, OPG, and ADAMTS13 were log transformed, while levels of vWF underwent quadratic transformation; no transformation was applied to GFAP levels. D-dimer showed the most significant predictive value for LVO (OR 1.13, 95% CI 1.07 to 1.20; p-value<0.001).

The inventors estimated the different levels of diagnostic performance obtained by varying the logistic model threshold of the GOOD biomarker model (FIG. 6). They divided the model values distribution into deciles, and found that the first two deciles (logistic model values: 0.18-0.71) were the most significant for LVO identification. Indeed, the odds ratio of LVO patients to have a positive test are 16.67 (CI 95%: 5.44-51.4; p-value=0.00011) and 5.55 (CI 95%: 2.11-12.50; p-value=0.0129), when the logistic model threshold was set at the first and second decile, respectively (FIG. 6). These data indicate that a biomarker panel composed of GFAP, OPN, OPG, and D-dimer (GOOD) may provide a highly specific tool for the identification of LVO from the population of pre-hospital suspected stroke patients.

Figure 10:
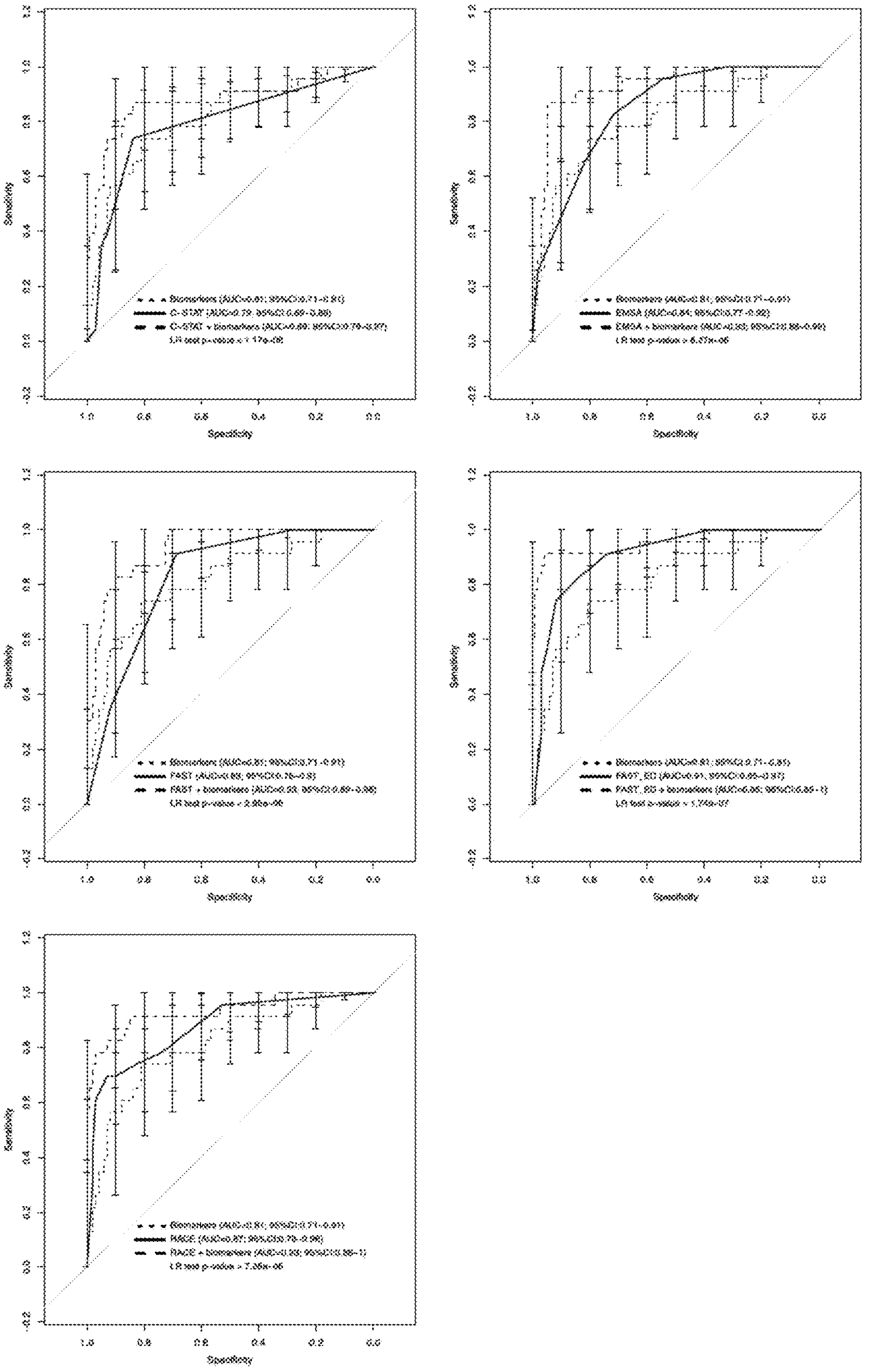
FIG. 10 shows ROC curves of stroke scales models with or without the addition of biomarkers. Addition of D-dimer and GFAP resulted in improved goodness of fit (i.e. lower AIC), LVO prediction (i.e. higher AUC), and significant LR test for each stroke scale tested, compared to using the stroke scales alone.

The inventors performed additional multivariable analysis and found, surprisingly, that the optimal set of blood biomarkers for LVO prediction was D-dimer (OR 15.44, 95% CI 4.91 to 57.6; p-value<0.0011) and GFAP (OR 0.83, 95% CI 0.5 to 0.99; p-value=0.03 FIG. 10). The AUC of the model with D-dimer and GFAP for LVO prediction was 81% (95% CI 74 to 88%; (FIG. 9) and the accuracy was 85% (95% CI 81 to 89%; Table 5). The inventors estimated a model threshold by maximising specificity and obtained sensitivity levels of 56% (95% CI 34 to 76%), specificity of 91% (95% CI 84 to 96%), LR+ of 6.99 (95% CI 3.29 to 14.88), and LR− of 0.47 (95% CI 0.3 to 0.76): (FIG. 14).

Example 2D—Integration of Biomarkers with Field Stroke Scales

Several pre-hospital scales based on patient symptoms have been developed for the identification of LVO stroke in the field and have shown high levels of diagnostic sensitivity for LVO, but lack diagnostic specificity[5,7,10,19,23]. The inventor's findings suggest that the GOOD biomarker panel could offer a highly specific tool for LVO identification. The inventors therefore hypothesised whether the inclusion of the blood biomarker panel could improve the diagnostic specificity of LVO prehospital stroke scales. They used the NIHSS score items to derive the stroke scales FAST, FAST-ED, RACE, CPSS, and EMSA, and estimated their diagnostic performance at established scale thresholds (FIG. 7). In the cohort, FAST-ED and RACE achieved highest diagnostic performance for LVO identification with accuracy of 84% (CI 95%: 80-89) and 86% (CI 95%: 82-91), and OR of 32.11 (12.86-81.4) and 24.54 (10.73-52.78), respectively.

The inventors then combined the blood biomarkers to pre-hospital stroke scales, and found that the GOOD panel improved diagnostic performance of all stroke scales tested (FIGS. 8 and 14). Highest diagnostic performance for LVO prediction was obtained with the combination of GOOD with FAST-ED, which achieved an accuracy of 96% (CI 95%: 94-98), sensitivity of 91% (CI 95%: 83-100), specificity of 97% (CI 95%: 95-99). According to this model, LVO patients were 39 (CI 95%: 18.2-96.09) times more likely to have a positive test, compared to non-LVO patients. Although the inventors found significant associations between our biomarkers and FAST-ED scale (GFAP: p-value=0.00139; OPN: p-value=0.01321; OPG: p-value=0.04144; D-dimer: p-value=0.00002), the logistic model built on the GOOD biomarkers was still highly significant, after adjustment for such associations (Fisher's exact p-value=$6.53^{e-12}$).

Further analysis by the inventors found that addition of D-dimer and GFAP resulted in improved goodness of fit (i.e. lower AIC), LVO prediction (i.e. higher AUC), and significant LR test for each stroke scale tested, compared to using the stroke scales alone (FIGS. 9, 10 and 14). The combination of D-dimer and GFAP with FAST-ED or EMSA resulted in the highest LR+ for LVO prediction (22.6, 95% CI 8.58 to 59.51 and 17.22, 95% CI 7.22 to 41.04, respectively), with LR− of 0.09 (95% CI 0.02 to 0.34) or 0.14 (95% CI 0.05 to 0.39), sensitivity of 91% (95% CI 71 to 98) or 86 (95% CI 66 to 97), and specificity of 95% (95% CI 89 to 98) or 94% (95% CI 88 to 98), respectively.

Without wishing to be bound to any particular theory, the inventor's findings indicate that the combination of D-dimer, OPN, OPG and GFAP, and particularly D-dimer and GFAP, with pre-hospital stroke scales can provide a highly accurate tool and could significantly enhance identification of LVO strokes.

Discussion

The inventors have for the first time identified OPN, OPG, and D-dimer as biomarkers for LVO stroke. They have also demonstrated that a biomarker panel composed of GFAP, OPN, OPG, and D-dimer (GOOD) can provide a valuable tool for the highly specific (94%) identification of stroke patients with a large vessel occlusion (LVO), from the population of suspected stroke patients. Moreover, the inventors have shown that combining the GOOD biomarker panel with pre-hospital stroke scales based on patient symptoms, can result in unprecedented diagnostic accuracy (>95%) for LVO identification.

The inventors analysed the plasma of 128 patients with suspected stroke. The observed proportion of LVO stroke, compared to all confirmed ischemic stroke, was 32%, which is line with previous reports[1]. In addition, the proportion of stroke mimics that we observed (29%), is comparable to other studies[67].

The inventors found that a cut-off value of 265 pg/mL on GFAP levels could identify haemorrhagic patients with a sensitivity of 30% and a specificity of 96%. To the inventor's knowledge, no studies have addressed directly the ability of GFAP measurements as a diagnostic tool to identify LVO patients. In addition, previous studies have not addressed the ability of plasma GFAP measurements to identify LVO patients.

The inventor's study demonstrates that, when measured with other blood biomarkers, GFAP can significantly improve LVO identification, by ruling out haemorrhagic patients from the population of suspected strokes. The inventors provide the first evidence that measurement of plasma GFAP could be used as a tool to diagnose and triage LVO patients.

The inventor's results also show not only that OPN and OPG are individually increased in LVO vs non-LVO patients, but also that both biomarkers significantly contribute to LVO identification either individually or when combined in the inventor's biomarker panel. While previously published studies focused on comparing D-dimer levels between subtypes of ischemic stroke or between ischemic stroke and control subjects, the inventor's study assessed D-dimer levels in LVO patients compared to a heterogeneous group of suspected stroke patients encompassing haemorrhagic stroke, non-LVO ischemic stroke, stroke mimics, and TIAs, thus simulating a realistic clinical scenario.

To the inventor's knowledge, this is the first evidence of increased D-dimer levels in LVO patients compared to a population of suspected stroke patients that closely resembles the one found in the pre-hospital setting.

The inventors have shown that the combination of multiple biomarkers into a panel allows to obtain higher diagnostic performance for LVO identification, compared with the use of individual biomarkers. In the inventor's study, the combination of GFAP, OPN, OPG, and D-dimer enabled to identify LVO stroke with 86% accuracy, which was higher compared to the highest scoring individual biomarker (i.e. D-dimer). Nevertheless, measurement of each biomarker alone still provides an accurate means of diagnosing LVO stroke. In particular, D-dimer alone resulted in a diagnostic accuracy of 83%, with clinically acceptable levels of specificity and sensitivity (89% and 52%, respectively), and the combination of D-dimer with GFAP results in even greater accuracy, with specificity and sensitivity of 91% and 56%, respectively.

These findings suggest that, although a more complex biomarker panel would allow more accurate identification of LVO strokes, the measurement of the biomarkers alone, and in particular D-dimer, may be chosen in particular clinical scenarios; for example, scenarios where blood sampling techniques do not allow collection of large blood volumes (e.g. field finger-prick sampling), or when test simplicity and rapidity are the priority (e.g. ambulance).

Several stroke scales based on patient symptoms have been developed to identify LVO stroke patients in the pre-hospital setting. In this study, the inventor's derived the LVO pre-hospital stroke scales FAST-ED, RACE, CPSS, and EMSA. In addition, they derived the FAST score, as this is currently the most widely applied pre-hospital scale. The inventors estimated diagnostic measures of these scales for LVO identification, and observed that their prediction performance was higher, compared to previous studies[5-10]. This could be due to the fact that they derived these stroke scales from the NIHSS score of each patient, which was taken by expert neurologists, instead of by trained paramedics.

The overall aim of identifying LVO patients in the field is to guide the decision of the ambulance staff towards transportation of suspected stroke patients to stroke centres with specialised capabilities. Since LVO stroke patients require treatment with endovascular thrombectomy (EVT), identification of these patients in the field could direct transportation to EVT-capable centres, even if these are not the nearest stroke centre. Direct transportation of LVO patients to EVT-capable centres has been shown to reduce time to treatment and patients outcome, compared to inter-hospital transfer[24]. Despite this, the use of pre-hospital stroke scales in the field is scattered across countries and their clinical value remains to be validated and confirmed. This could be due, as it has been previously suggested[25], to the limited diagnostic specificity for LVO thus far demonstrated. Indeed, high levels of specificity (or positive predictive value) would be required to modify the ambulance journey from transportation to the nearest stroke centre, towards the nearest EVT-capable centre[26].

In this study the inventors propose the combination of blood biomarkers with pre-hospital stroke scales for the identification of LVO. The inventors have identified novel biomarkers for LVO stroke and have demonstrated that a model built on the GOOD biomarker panel in conjunction with pre-hospital stroke scales, can lead to an even higher predictive ability for LVO, compared to the use of blood biomarkers, or stroke scales, in isolation. The inventors observed that the combination of the GOOD biomarker panel with FAST-ED resulted in the highest diagnostic accuracy for LVO (96%), while the combination with RACE led to the highest sensitivity (81%). Of note, the highest diagnostic specificity (98%) was obtained when combining the GOOD panel with either FAST or EMSA. The inventors have also shown that these findings indicate that, combining the biomarker panel with pre-hospital stroke scales, could provide the much-needed diagnostic performance to triage LVO patients in the field with confidence.

In order to address various issues and advance the art, the entirety of this disclosure shows by way of illustration various embodiments in which the claimed invention(s) may be practiced and provide for a superior diagnostic test for stroke resulting from large vessel occlusion. The advantages and features of the disclosure are of a representative sample of embodiments only, and are not exhaustive and/or exclusive. They are presented only to assist in understanding and teach the claimed features. It is to be understood that advantages, embodiments, examples, functions, features, structures, and/or other aspects of the disclosure are not to be considered limitations on the disclosure as defined by the claims or limitations on equivalents to the claims, and that other embodiments may be utilised and modifications may be made without departing from the scope and/or spirit of the disclosure. Various embodiments may suitably comprise, consist of, or consist essentially of, various combinations of the disclosed elements, components, features, parts, steps, means, etc. In addition, the disclosure includes other inventions not presently claimed, but which may be claimed in future.

REFERENCES

1. Malhotra, K. Ischemic Strokes Due to Large-Vessel Occlusions Contribute Disproportionately to Stroke-Related Dependence and Death: A Review. 8, 1-5 (2017).
2. Albers, G. W. et al. Thrombectomy for stroke at 6 to 16 hours with selection by perfusion imaging. *N. Engl. J. Med.* 378, 708-718 (2018).
3. Nogueira, R. G. et al. Thrombectomy 6 to 24 hours after stroke with a mismatch between deficit and infarct. *N. Engl. J. Med.* 378, 11-21 (2018).
4. Goyal, M. et al. Endovascular thrombectomy after large-vessel ischaemic stroke: A meta-analysis of individual patient data from five randomised trials. *Lancet* 387, 1723-1731 (2016).
5. Lima, F. O. et al. Field Assessment Stroke Triage for Emergency Destination. *Stroke* 47, 1997-2002 (2016).
6. Taqi, M. A. et al. ARTICLE IN PRESS Design, Application and In field Validation of a Pre-Hospital Emergent Large Vessel Occlusion Screening Tool: Ventura Emergent Large Vessel Occlusion Score Shepherd, MD. *J. Stroke Cerebrovasc. Dis.* 1-7 (2018). doi:10.1016/j.jstrokecerebrovasdis.2018.11.014
7. Pérez de la Ossa, N. et al. Design and Validation of a Prehospital Stroke Scale to Predict Large Arterial Occlusion. 45, 87-91 (2014).
8. Teleb, M. S., Hage, A. Ver, Carter, J., Jayaraman, M. V & Mctaggart, R. A. Stroke vision, aphasia, neglect (VAN) assessment—a novel emergent large vessel occlusion screening tool: pilot study and comparison with current clinical severity indices. 122-126 (2017). doi:10.1136/neurintsurg-2015-012131
9. Gropen, T. I., Gazi, M., Minor, M., Fadairo, A. & Acker, J. Centrally Guided Identification of Patients With Large Vessel Occlusion: Lessons From Trauma Systems. *J. Stroke Cerebrovasc. Dis.* 1-10 (2019). doi:10.1016/j.jstrokecerebrovasdis.2019.06.042
10. Gropen, T. I. et al. Derivation and Validation of the Emergency Medical Stroke Assessment and Comparison of Large Vessel Occlusion Scales. *J. Stroke Cerebrovasc. Dis.* 27, 806-815 (2018).
11. Ermak, D. et al. Abstract 46: Six of One, Half a Dozen of the Other: Single-Center Retrospective Comparison of Prehospital Large Vessel Occlusion Tools. *Stroke* 49, (2018).

12. Heldner, M. R. et al. National institutes of health stroke scale score and vessel occlusion in 2152 patients with acute ischemic stroke. *Stroke* 44, 1153-1157 (2013).
13. Heldner, M. R. et al. Clinical prediction of large vessel occlusion in anterior circulation stroke: mission impossible? *J. Neurol.* 263, 1633-1640 (2016).
14. Sharma, R., Macy, S., Richardson, K., Lokhnygina, Y. & Laskowitz, D. T. A Blood-based Biomarker Panel to Detect Acute Stroke. *J. Stroke Cerebrovasc. Dis.* 23, 910-918 (2014).
15. Bustamante, A. et al. Blood Biomarkers for the Early Diagnosis of Stroke. 2419-2425 (2017). doi:10.1161/STROKEAHA.117.017076
16. Wang, K. et al. Association of plasma soluble CD40L and P-selectin with large-artery atherosclerosis stroke. *Int. J. Clin. Exp. Pathol.* 10, 4827-4832 (2017).
17. Arenillas, J. F. et al. C-reactive protein predicts further ischemic events in first-ever transient ischemic attack or stroke patients with intracranial large-artery occlusive disease. *Stroke* 34, 2463-2468 (2003).
18. Chang, A. et al. Cardiac Biomarkers Predict Large Vessel Occlusion in Patients with Ischemic Stroke. *J. Stroke Cerebrovasc. Dis.* 28, 1726-1731 (2019).
19. Katz, B. S., McMullan, J. T., Sucharew, H., Adeoye, O. & Broderick, J. P. Design and Validation of a Prehospital Scale to Predict Stroke Severity: Cincinnati Prehospital Stroke Severity Scale. *Stroke* 46, 1508-1512 (2015).
20. Llombart, V. et al. Plasmatic retinol-binding protein 4 and glial fibrillary acidic protein as biomarkers to differentiate ischemic stroke and intracerebral hemorrhage. *Int. Soc. Neurochem.* 416-424 (2016). doi:10.1111/jnc.13419
21. Misra, S. et al. Blood-based protein biomarkers for stroke differentiation: A systematic review. *PROTEOMICS—Clin. Appl.* 11, 1700007 (2017).
22. Foerch, C. et al. Serum glial fibrillary acidic protein as a biomarker for intracerebral haemorrhage in patients with acute stroke. *J. Neurol. Neurosurg. Psychiatry* 77, 181-184 (2006).
23. Singer, O. C. et al. A simple 3-item stroke scale: Comparison with the National Institutes of Health Stroke Scale and prediction of middle cerebral artery occlusion. *Stroke* 36, 773-776 (2005).
24. Froehler, M. T. et al. Interhospital Transfer Before Thrombectomy Is Associated With Delayed Treatment and Worse Outcome in the STRATIS Registry (Systematic Evaluation of Patients Treated With Neurothrombectomy Devices for Acute Ischemic Stroke). *Circulation* 136, 2311-2321 (2017).
25. English, S. W., Rabinstein, A. A., Mandrekar, J. & Klaas, J. P. Rethinking Prehospital Stroke Notification: Assessing Utility of Emergency Medical Services Impression and Cincinnati Prehospital Stroke Scale. *J. Stroke Cerebrovasc. Dis.* 27, 919-925 (2018).
26. Smith, E. E. et al. Accuracy of Prediction Instruments for Diagnosing Large Vessel Occlusion in Individuals With Suspected Stroke: A Systematic Review for the 2018 Guidelines for the Early Management of Patients With Acute Ischemic Stroke. *Stroke* 49, e111-e122 (2018).

The invention claimed is:

1. A method of treating large vessel occlusion (LVO) stroke comprising:

(i) identifying an individual presenting with stroke symptoms;

(ii) determining that the individual is experiencing LVO stroke comprising:

(a) within 24 hours of step (i), obtaining a blood sample from the individual;

(b) measuring the amount of D-dimer in the blood sample, or in plasma or serum derived therefrom; and (c) measuring the amount of glial fibrillary acidic protein (GFAP) in the blood sample, or in plasma or serum derived therefrom;

(iii) providing LVO therapy to the individual having elevated levels of D-dimer and decreased levels of GFAP compared to levels of D-dimer and GFAP in one or more controls, wherein the individual receiving LVO therapy has D-dimer levels of at least 0.5 μg/ml and GFAP levels of less than 265 pg/ml.

2. The method of claim 1, wherein the LVO therapy comprises administration of an antithrombotic agent and/or mechanical thrombectomy.

3. The method of claim 1, wherein determining that the individual is experiencing LVO stroke further comprises one or more of computerized tomography (CT), CT angiography (CTA), magnetic resonance angiography (MRA), MRI, diffusion weighted imaging, or cerebral angiography scan of the individual's head.

4. The method of claim 1, wherein the individual receiving LVO therapy has D-dimer levels of at least 1 μg/ml and GFAP levels of less than 200 pg/ml.

5. The method of claim 1, wherein the individual receiving LVO therapy has D-dimer levels of at least 1.5 μg/ml and GFAP levels of less than 100 pg/ml.

6. The method of claim 1, further comprising determining a stroke severity score from the individual, wherein the stroke severity score is selected from National Institutes of Health Stroke Scale (NIHSS), Field Assessment Stroke Triage (FAST), FAST for Emergency Destination (FAST-ED), Rapid Arterial Occlusion Evaluation (RACE), Cincinnati Stroke Triage Assessment Tool (C-STAT) and Emergency Medical Stroke Assessment (EMSA).

7. A method of treating large vessel occlusion (LVO) stroke comprising:

(i) identifying an individual presenting with stroke symptoms;

(ii) determining that the individual is experiencing LVO stroke comprising:

(a) within 24 hours of step (i), obtaining a blood sample from the individual;

(b) measuring the amount of D-dimer in the blood sample, or in plasma or serum derived therefrom;

(c) measuring the amount of glial fibrillary acidic protein (GFAP) in the blood sample, or in plasma or serum derived therefrom; and (d) measuring one or more of (1) the amount of osteopontin (OPN) in the sample and (2) the amount of osteoprotegerin (OPG) in the blood sample, or in plasma or serum derived therefrom; and (iii) providing LVO therapy to the individual having elevated levels of D-dimer, decreased levels of GFAP, and one or more of (1) elevated levels of OPN and (2) elevated levels of OPG, compared to levels of D-dimer, GFAP, and OPN and/or OPG in one or more controls.

8. The method of claim 7, wherein the LVO therapy comprises administration of an antithrombotic agent and/or mechanical thrombectomy.

9. The method of claim 7, wherein determining that the individual is experiencing LVO stroke further comprises one or more of computerized tomography (CT), CT angiography (CTA), magnetic resonance angiography (MRA), MRI, diffusion weighted imaging, or cerebral angiography scan of the individual's head.

10. The method of claim 7, wherein the individual receiving LVO therapy has D-dimer levels of at least 0.5 μg/ml and GFAP levels of less than 265 pg/ml; and one or more of (1) OPN levels of at least 1 ng/ml and (2) OPG levels of at least 100 pg/ml.

11. The method of claim 7, wherein the individual receiving LVO therapy has D-dimer levels of at least 1 μg/ml and GFAP levels of less than 200 pg/ml; and one or more of (1) OPN levels of at least 1.6 ng/ml and (2) OPG levels of at least 125 pg/ml, or (3) OPN levels of at least 1.6 ng/ml and OPG levels of at least 120 pg/ml.

12. The method of claim 7, wherein the individual receiving LVO therapy has D-dimer levels of at least 1.5 μg/ml and GFAP levels of less than 100 pg/ml; and one or more of (1) OPN levels of at least 2.5 ng/ml and (2) OPG levels of at least 200 pg/ml.

13. The method of claim 7, further comprising determining a stroke severity score from the individual, wherein the stroke severity score is selected from NIHSS, FAST, FAST-ED, RACE, C-STAT and EMSA.

* * * * *

UNITED STATES PATENT AND TRADEMARK OFFICE

CERTIFICATE OF CORRECTION

PATENT NO. : 11,726,100 B2
APPLICATION NO. : 17/934454
DATED : August 15, 2023
INVENTOR(S) : Edoardo Gaude et al.

It is certified that error appears in the above-identified patent and that said Letters Patent is hereby corrected as shown below:

On the Title Page

Under item (56), OTHER PUBLICATIONS

Line 13, delete “Fibrllary” and insert -- Fibrillary --.

Line 15, delete “Ischemica” and insert -- Ischemia --.

In the Specification

Column 4, Lines 8-9, delete “from the or” and insert -- from the --.

Column 4, Line 21, delete “from an or” and insert -- from an --.

Column 6, Line 26, delete “and or” and insert -- and/or --.

Column 7, Line 42 (Approx.), delete “DADQWEENGA” and insert -- DADQWEENCA --.

Column 18, Line 6, delete “EQQNAKLAAE” and insert -- EQQNKALAAE --.

Column 18, Line 16, delete “EMARHLQYEQ” and insert -- EMARHLQEYQ --.

Column 32, Line 36, delete “and or” and insert -- and/or --.

Column 38, Line 54, delete “Criteorion” and insert -- Criterion --.

Column 38, Line 56, delete “freedome” and insert -- freedom --.

Column 40, Line 32, delete “1b:” and insert -- 1B: --.

Signed and Sealed this
Twentieth Day of August, 2024

Katherine Kelly Vidal

Katherine Kelly Vidal
*Director of the United States Patent and Trademark Office*

Column 40, Line 54, delete “benzadine,” and insert -- benzidine, --.

Column 43, Line 9, delete “nnet,” and insert -- net, --.

Column 43, Line 9, delete “oddsratio,” and insert -- odds ratio, --.

Column 43, Line 44, delete “they” and insert -- They --.

Column 43, Line 50, delete “the” and insert -- The --.

SEQUENCE LISTING

```
Sequence total quantity: 8
SEQ ID NO: 1            moltype = AA  length = 866
FEATURE                 Location/Qualifiers
source                  1..866
                        mol_type = protein
                        organism = Homo sapiens
SEQUENCE: 1
MFSMRIVCLV LSVVGTAWTA DSGEGDFLAE GGGVRGPRVV ERHQSACKDS DWPFCSDEDW  60
NYKCPSGCRM KGLIDEVNQD FTNRINKLKN SLFEYQKNNK DSHSLTTNIM EILRGDFSSA  120
NNRDNTYNRV SEDLRSRIEV LKRKVIEKVQ HIQLLQKNVR AQLVDMKRLE VDIDIKIRSC  180
RGSCSRALAR EVDLKDYEDQ QKQLEQVIAK DLLPSRDRQH LPLIKMKPVP DLVPGNFKSQ  240
LQKVPPEWKA LTDMPQMRME LERPGGNEIT RGGSTSYGTG SETESPRNPS SAGSWNSGSS  300
GPGSTGNRNP GSSGTGGTAT WKPGSSGPGS TGSWNSGSSG TGSTGNQNPG SPRPGSTGTW  360
NPGSSERGSA GHWTSESSVS GSTGQWHSES GSFRPDSPGS GNARPNNPDW GTFEEVSGNV  420
SPGTRREYHT EKLVTSKGDK ELRTGKEKVT SGSTTTTRRS CSKTVTKTVI GPDGHKEVTK  480
EVVTSEDGSD CPEAMDLGTL SGIGTLDGFR HRHPDEAAFF DTASTGKTFP GFFSPMLGEF  540
VSETESRGSE SGIFTNTKES SSHHPGIAEF PSRGKSSSYS KQFTSSTSYN RGDSTFESKS  600
YKMADEAGSE ADHEGTHSTK RGHAKSRPVR DCDDVLQTHP SGTQSGIFNI KLPGSSKIFS  660
VYCDQETSLG GWLLIQQRMD GSLNFNRTWQ DYKRGFGSLN DEGEGEFWLG NDYLHLLTQR  720
GSVLRVELED WAGNEAYAEY HFRVGSEAEG YALQVSSYEG TAGDALIEGS VEEGAEYTSH  780
NNMQFSTFDR DADQWEENCA EVYGGGWWYN NCQAANLNGI YYPGGSYDPR NNSPYEIENG  840
VVWVSFRGAD YSLRAVRMKI RPLVTQ                                        866

SEQ ID NO: 2            moltype = DNA  length = 3654
FEATURE                 Location/Qualifiers
source                  1..3654
                        mol_type = genomic DNA
                        organism = Homo sapiens
SEQUENCE: 2
aatcctttct ttcagctgga gtgctcctca ggagccagcc ccacccttag aaaagatgtt  60
ttccatgagg atcgtctgcc tggtcctaag tgtggtgggc acagcatgga ctgcagatag  120
tggtgaaggt gactttctag ctgaaggagg aggcgtgcgt ggcccaaggg ttgtggaaag  180
acatcaatct gcctgcaaag attcagactg gcccttctgc tctgatgaag actggaacta  240
caaatgccct tctggctgca ggatgaaagg gttgattgat gaagtcaatc aagattttac  300
aaacagaata aataagctca aaaattcact atttgaatat cagaagaaca ataaggattc  360
tcattcgttg accactaata taatggaaat tttgagaggc gatttttcct cagccaataa  420
ccgtgataat acctacaacc gagtgtcaga ggatctgaga agcagaattg aagtcctgaa  480
gcgcaaagtc atagaaaaag tacagcatat ccagcttctg cagaaaaatg ttagagctca  540
gttggttgat atgaaacgac tggaggtgga cattgatatt aagatccgat cttgtcgagg  600
gtcatgcagt agggctttag ctcgtgaagt agatctgaag gactatgaag atcagcagaa  660
gcaacttgaa caggtcattg ccaaagactt acttccctct agagataggc aacacttacc  720
```

-continued

```
actgataaaa atgaaaccag ttccagactt ggttcccgga aattttaaga gccagcttca  780
gaaggtaccc ccagagtgga aggcattaac agacatgccg cagatgagaa tggagttaga  840
gagacctggt ggaaatgaga ttactcgagg aggctccacc tcttatggaa ccggatcaga  900
gacggaaagc cccaggaacc ctagcagtgc tggaagctgg aactctggga gctctggacc  960
tggaagtact ggaaaccgaa accctgggag ctctgggact ggagggactg caacctggaa 1020
acctgggagc tctggacctg gaagtactgg aagctggaac tctgggagct ctggaactgg 1080
aagtactgga aaccaaaacc ctgggagccc tagacctggt agtaccggaa cctggaatcc 1140
tggcagctct gaacgcggaa gtgctgggca ctggacctct gagagctctg tatctggtag 1200
tactggacaa tggcactctg aatctggaag ttttaggcca gatagcccag gctctgggaa 1260
cgcgaggcct aacaacccag actggggcac atttgaagag gtgtcaggaa atgtaagtcc 1320
agggacaagg agagagtacc acacagaaaa actggtcact tctaaaggag ataaagagct 1380
caggactggt aaagagaagg tcacctctgg tagcacaacc accacgcgtc gttcatgctc 1440
taaaaccgtt actaagactg ttattggtcc tgatggtcac aaagaagtta ccaaagaagt 1500
ggtgacctcc gaagatggtt ctgactgtcc cgaggcaatg gatttaggca cattgtctgg 1560
cataggtact ctggatgggt tccgccatag gcaccctgat gaagctgcct tcttcgacac 1620
tgcctcaact ggaaaaacat tcccaggttt cttctcacct atgttaggag agtttgtcag 1680
tgagactgag tctaggggct cagaatctgg catcttcaca aatacaaagg aatccagttc 1740
tcatcaccct gggatagctg aattcccttc ccgtggtaaa tcttcaagtt acagcaaaca 1800
atttactagt agcacgagtt acaacagagg agactccaca tttgaaagca agagctataa 1860
aatggcagat gaggccggaa gtgaagccga tcatgaagga acacatagca ccaagagagg 1920
ccatgctaaa tctcgccctg tcagagactg tgatgatgtc ctccaaacac atccttcagg 1980
tacccaaagt ggcattttca atatcaagct accgggatcc agtaagattt tttctgttta 2040
ttgcgatcaa gagaccagtt tgggaggatg gcttttgatc cagcaaagaa tggatggatc 2100
actgaatttt aaccggacct ggcaagacta caagagaggt ttcggcagcc tgaatgacga 2160
gggggaagga gaattctggc taggcaatga ctacctccac ttactaaccc aaaggggctc 2220
tgttcttagg gttgaattag aggactgggc tgggaatgaa gcttatgcag aatatcactt 2280
ccgggtaggc tctgaggctg aaggctatgc cctccaagtc tcctcctatg aaggcactgc 2340
gggtgatgct ctgattgagg gttccgtaga ggaaggggca gagtacacct ctcacaacaa 2400
catgcagttc agcacctttg acagggatgc agaccagtgg gaagagaact gtgcagaagt 2460
ctatggggga ggctggtggt ataataactg ccaagcagcc aatctcaatg gaatctacta 2520
ccctgggggc tcctatgacc caaggaataa cagtccttat gagattgaga atggagtggt 2580
ctgggtttcc tttagagggg cagattattc cctcagggct gttcgcatga aaattaggcc 2640
ccttgtgacc caataggctg aagaagtggg aatgggagca ctctgtcttc tttgctagag 2700
aagtggagag aaaatacaaa aggtaaagca gttgagattc tctacaacct aaaaaaattcc 2760
taggtgctat ttcttatcc tttgtactgt agctaaatgt acctgagaca tattagtctt 2820
tgaaaaataa agttatgtaa ggtttttttt atctttaaat agctctgtgg gttttaacat 2880
ttttataaag atataccaag ggccattcag tacatcagga aagtggcaga cagaagcttc 2940
tctctgcaac cttgaagact attggtttga gaacttctct tcccatacca cccaaaatca 3000
taatgccatt ggaaagcaaa aagttgtttt atccatttga tttgaattgt tttaagccaa 3060
tattttaagg taaaactcac tgaatctaac catagctgac ctttgtagta gaatttacaa 3120
cttataatta caatgcacaa tttataatta caatatgtat ttatgtcttt tgctatggag 3180
caaatccagg aaggcaagag aaacattctt tcctaaatat aaatgaaaat ctatccttta 3240
aactcttcca ctagacgttg taatgcacac ttattttttt cccaaggagt aaccaatttc 3300
tttctaaaac acatttaaaa ttttaaaact atttatgaat attaaaaaaa gacataattc 3360
acacattaat aaacaatctc ccaagtattg atttaacttc atttttctaa taatcataaa 3420
ctatattctg tgacatgcta attattatta aatgtaagtc gttagttcga aagcctctca 3480
ctaagtatga tctatgctat attcaaaatt caacccattt actttggtca atatttgatc 3540
taagttgcat ctttaatcct ggtggtcttg ccttctgatt tttaatttgt atcctttttct 3600
attaagatat atttgtcatt ttctcttgaa tatgtattaa aatatcccaa gcaa       3654
```

```
SEQ ID NO: 3            moltype = AA  length = 314
FEATURE                 Location/Qualifiers
source                  1..314
                        mol_type = protein
                        organism = Homo sapiens
SEQUENCE: 3
MRIAVICFCL LGITCAIPVK QADSGSSEEK QLYNKYPDAV ATWLNPDPSQ KQNLLAPQNA  60
VSSEETNDFK QETLPSKSNE SHDHMDDMDD EDDDDHVDSQ DSIDSNDSDD VDDTDDSHQS 120
DESHHSDESD ELVTDFPTDL PATEVFTPVV PTVDTYDGRG DSVVYGLRSK SKKFRRPDIQ 180
YPDATDEDIT SHMESEELNG AYKAIPVAQD LNAPSDWDSR GKDSYETSQL DDQSAETHSH 240
KQSRLYKRKA NDESNEHSDV IDSQELSKVS REFHSHEFHS HEDMLVVDPK SKEEDKHLKF 300
RISHELDSAS SEVN                                                  314
```

```
SEQ ID NO: 4            moltype = DNA  length = 7698
FEATURE                 Location/Qualifiers
source                  1..7698
                        mol_type = genomic DNA
                        organism = Homo sapiens
SEQUENCE: 4
agcagcagga ggaggcagag cacagcatcg tcgggaccag actcgtctca ggccagttgc  60
agccttctca gccaaacgcc gaccaaggta cagcttcagt ttgctactgg gttgtgcatt 120
cagctgaatt tcatggggaa gtccaaattc taaggaaaaa tatttttaat tgtaatgctg 180
ttaaacagac ttaaattttc tagccttttt aataagcaga ttagatacat tgcaggtctc 240
ctggaacaaa ggtgtctaga tattttgaat gccaatcaaa tttaaaactt aaaaatactt 300
ccactgggtc ctcaaaagaa cggaaaccac cgatgctaat cagaaaatag taaaattaaa 360
ttccccttttg gaataattat acctatataa ttttcagtgg gtgactgtgc aggaatttaa 420
aagaaaaggg atcttttatg ctaattaaac caattacaat gctatttttt aaatgatgta 480
tctcactttt aaggggaaga aaacccttc tgaatatgcc actgctaaat ttagctgtta 540
aaatattcac caagatacct gtatgacact gtgtaggctt attattacaa atagaaaagc 600
```

-continued

```
tgttggctat tttcaatgtt ttcctttgaa tttcaaattt ttagaacatc ttacttaaat  660
aacaaatttc agagatagtt tgatttcacc taagtagcac ctacttgata attaagctaa  720
aagtcacatt taaagtacat gttggaaaaa tggataaagc aaattttttt catttttttc  780
tgtgagtttt ttcttctcta aaaaatattc ccatactagc ttattaatat aattaagtta  840
ctgttgatct gtttgtaggt ttagagagct agatatataa ggtagtaatg gtataatttc  900
tggaactcta aattttaaag ttgaataaat acagacttgc aaaatttccc tttcccttgc  960
ctaatagtga aagatggata ataggtggca atataaatat taacttgaaa gactataata  1020
ctaaaaagaa aaggcatctc taagaagtag aaaagattct atagaaaata tattttattt  1080
gtgatcattt tgtaatgtgg tagtataaaa aggtatcact gttgtaacct atgaagatgt  1140
cagctattcc ttatgaaata ttttgcagga aaactcacta ccatgagaat tgcagtgatt  1200
tgcttttgcc tcctaggcat cacctgtgcc ataccagtga gtacagttgc atcttaaaga  1260
aaattcctga aaataactga attgtgtgct tccatgtgct aggaggacat tcttgtaatc  1320
tttcttcatc ttttctgttt ctaaggttaa acaggctgat tctggaagtt ctgaggaaaa  1380
gcaggtaagc atcttttatg tttttatata gttaaatcat ttactcaatt atggcgagag  1440
gtgcaagaaa cgtatttgct gcgatattac ttatcttctc agtcaaatcc attggtttac  1500
aagtattgat tgactgcctg ctatgaatct aggccagtac caagcacagt atagttttta  1560
ataaatataa gtttataaaa ccaacccaga tattttaaat ataataatat ctaggcatgt  1620
atgatgagtt atcgcatgta agataagtta tatgaagttg tgtgactttt tttccattag  1680
tccacatact gatctaaaag cagaaaattc cagcttttgc tttgtttagt ggattgctaa  1740
gtttaaaatt cacattggat attagtcaga actgtttgta tgaccataat attcacaata  1800
ttgtctgaga tattagctga gaagcccatt gtgaaaagaa agtctatgtg tgctgtttgt  1860
atctattgtg attgtcagct gatgttagat cacattttct aaccaaacat aagaccaacc  1920
aaactcttta ttataattat ttgaccagca ctaaagatgt acctacccct ccacaacaga  1980
tgaaactgtg ccagccaaac aacaaatggg cattgtcccc agaagcttgg acaaaaaggc  2040
acacagagtt caattccagt tgaacagaat aaaggccaaa atagagctgc cttggggggtc  2100
actgcaatta gactgcttaa tgaagacatt aaaagaagta ttctgtgttc gtttgtgtgt  2160
ggaggggtgt gtgtgtctgt ttttcaactg atttgaaaat acaggtgttg aatcctaata  2220
ataaaccaga aaaattaaca tctccagaga agatagaggt catactattt gaggcaagaa  2280
ttagcgtctt tttaataaac gaaaatatgg caaagatgca ttttagaagg cacgtggagc  2340
tataacaatt taagaaatac gtgaagagct caaggctcag ccttctagaa tcccagaaac  2400
ttaaagctag taaaaaattg gggaagtctc taaggatata tgcctgaaaa tacacactgg  2460
ttatctgtga gtgttaggat tactgggtgg tttttagtct attcattttg cttaccttta  2520
ttttcttcat attagttttt aaaaattata aatgtaactt atacatccat tctctctgag  2580
cctgtattac atgtgtcatg agaatagata gatagatatg aaaaagtgaa gagaaaaact  2640
ctgaactcat ctggtctcac tgtttttccg ccttcttttt tttttttttt tttttttttt  2700
gagacggagt ctcgctccgt cgcccaggct ggagtgcagt ggtgtgatct cggctcactg  2760
caagctccgc ctcccaggtt caccccattc tcctgagtag ctgggactac aggcgcccgc  2820
caccacgccc ggataatttt ttgtattttt agtagagacg gggtttcacc gtgttagcca  2880
ggatggtctc catctcctga cctcgtgatc caccctcctt ggcctcccaa agtgctggga  2940
ttacaggcgt gagccactgc gcccggctgt tttttcatct tcttaaagca aggaacccct  3000
tctttcagca aaacctttcg gagaagccca atactaagct cctctggtta gagccagcca  3060
tgagagaaac tccaagtact tctgactggt tctctctcta ctcatccacc ccttaggtgg  3120
ctgcagaagg aactctgtgc aacccccaga gttctcattc tcagtgacag ggaaatgtaa  3180
tgattggccc tggatgattc agcagatcag atgatactta ctcagagcaa tttccactcc  3240
tttgcagtag catattatca gtattttcca gataaataac ttggctaaag aaaaatccat  3300
ttcatttaca tctttggcac cttacagcaa tagaactttt gtgcaatgat tttaatatta  3360
tatttctaca ttggctgata agatacatat ggctattgag cactcaaaat gtgggctagt  3420
gcaactgagg aactgaattt ttatcttctt tttttttttt tttttttttg agatggagtc  3480
ttgctctgtc acccaggctg gagtgcagtg gcgcaatctt ggctcactgc aagctctgcc  3540
tcctgggttc acgccattct cttgcctcag cctccccagt agctgggggt acaggtgcct  3600
gccaccacgc ccggctattt tttttatttt ttattttttt tagtagaaac ggggtttcac  3660
tgtgttagcc aggatgttct cgatctcctg acctcgtgat ccgcctgcct cggcctccca  3720
aagtgctggg attacagggg tgagccaccg tgcctagcca tttcatttta attaacttaa  3780
atttaaatag ctccatgtgg ttagaggata ctgaattagc acagtcttag agagttcctt  3840
cttgttccat ggactggaca caatgaagat taacagtaat taaggtcact tctggtttag  3900
atgtgcttta tctgagagga aaattcagcc agcaaacata caaaaagaaa gcacagtgtg  3960
aagttcggtg ttaagagcta gtttgcctgc gtttgaaccc tgcctggctc tgccatttcc  4020
taccacttaa ctgcactgtg gctgagtttt ctgatctgta aggtgggaat aataatgata  4080
cctatctcat aggggaatga aaggatcaaa tgagttcata tttgtaaagc aatttgaaag  4140
agtgcctagc ccacagtaag tgctacataa gagtttgtta aatgaatctg caaaaaaaaa  4200
aaaattacaa aaaggtacct aagggtccgg gtgactatat gcttccatca agactagtga  4260
agaatggttg ttttttccat tcatccctac atttcttttt ttaataatga taaacatgca  4320
actttttttgt agctttacaa caaataccca gatgctgtgg ccacatggct aaaccctgac  4380
ccatctcaga agcagaatct cctagcccca caggtatttt taaacttctc ataattaaac  4440
tacagtgatg aaagatagcc acactcaggc catttgggct gctcagatga atcctgcctg  4500
cctgctggca aacatgtgct taggacattg actgatctgc catgttggct tctctctgtg  4560
ttaagccatc cacagatgag gctgaaaaat aaaaactgct ttggattaaa aaggttaact  4620
tttgaataaa aaagctaggc atgtgtgatg cgcactaaca cgtgccattc cttcttcaga  4680
atgctgtgtc ctctgaagaa accaatgact ttaaacaaga ggtaagttct cattttcaat  4740
cagaggccca tcatgccttg aagagatgaa agaaggcatt gcctggattc tcttctgatg  4800
aaatttcatt agcaagtttt ccagctaatt ggcagtctaa aacttgctca taaataaaac  4860
atgtatttac taaatatcag aaatactagg tttcctcgga taagtttagc attacagaag  4920
atgtttatta atgcctgtta tttgaaacat taatctgctt gcaatttatt taaggtattt  4980
tgtagatatc taatatctaa taagcatcta attaatgcat atcaaagcta agattttgcc  5040
tttaggaaag ttttctttcc taataaaata gtttatttga caactattct ttttattagg  5100
atcattcata tatttgctaa gcaaagagta aatttatttt ccttaagatt caatttgaat  5160
atactaagaa tattaaagca agttagataa attacccaat atatttgtca atttgaaatt  5220
tgatagacat tagttgttta attcaatggg cagttttgag ctgcagttta tacacacatg  5280
cataacagag tcacctttca attatccatg ttaataggaa agtggttata gattttagta  5340
```

-continued

```
cacacattaa aatatggata ctcttctctt ttgataaatc tcatttcaaa taaaaaaacc  5400
agtctcataa ttatgtatct gtatctatta catcattgaa tttagtaaat aatgtttaat  5460
atgtataagg aaaaacaatg ttattgacat gaagattata ctcacatatt tggcttgaaa  5520
atatctataa aaataatttc tgttgcaaag taagaaatgt tcttcagaat gttattaatc  5580
cctgtgttaa aagagaaatt ggaagatgct cactttagct cctaaaagcc atggtatgta  5640
ctgtgaatgc aaagattctg aaactaaata aaaagaaaga tagtaaaaga ctaatgtgct  5700
ataaaggcta agggaaaata aaaacccata tattaatttt cccggccatc ttaattttca  5760
gacccttcca agtaagtcca acgaaagcca tgaccacatg gatgatatgg atgatgaaga  5820
tgatgatgac catgtggaca gccaggactc cattgactcg aacgactctg atgatgtaga  5880
tgacactgat gattctcacc agtctgatga gtctcaccat tctgatgaat ctgatgaact  5940
ggtcactgat tttcccacgg acctgccagc aaccgaagtt ttcactccag ttgtccccac  6000
agtagacaca tatgatggcc gaggtgatag tgtggtttat ggactgaggt caaaatctaa  6060
gaagtttcgc agacctgaca tccaggtaaa tcctttaaca gacacacctg atggttctga  6120
ctagcgctca agtctaggaa accacagttt gcatattcat tcattcattc atccattcat  6180
tcatccattc agcaagaatt cattcatatt ctactttatg accattgaat acaaatcttt  6240
ttctgcttgg cggtttttgt aagtctacat aatttctctc tagatttgat tctcaaacac  6300
aattctactt tttgaaatcc tggatcactt attttcagat taaaataaat ggaaaacacc  6360
aattatttaa aaaaaataat ggtcatgttt tgaagttaaa tacctaagag gaattgtagt  6420
tgcaaattac actgaatcct tagtcacaga atctggattt gacatagcct tgccgtttac  6480
tattctcttt actttttaac taacaattca cttcctcttt atgtaggttt caatataatg  6540
aaacctacct cataggtttc attacatatg taagtgatgt agttattaaa ctaaatgaga  6600
tgacatatgt gaaaggcctt ggtaaagtac tatacaaagt aacatgctag tattatttca  6660
gccagattta gacaattttt agtataagat gacctaaaag ctagagagtg gaaaaggatt  6720
accatattcc catccctagc cgttcatata attattcttc atttgtgccg tgattcagta  6780
ccctgatgct acagacgagg acatcacctc acacatggaa agcgaggagt tgaatggtgc  6840
atacaaggcc atccccgttg cccaggacct gaacgcgcct tctgattggg acagccgtgg  6900
gaaggacagt tatgaaacga gtcagctgga tgaccagagt gctgaaaccc acagccacaa  6960
gcagtccaga ttatataagc ggaaagccaa tgatgagagc aatgagcatt ccgatgtgat  7020
tgatagtcag gaactttcca aagtcagccg tgaattccac agccatgaat ttcacagcca  7080
tgaagatatg ctggttgtag accccaaaag taaggaagaa gataaacacc tgaaatttcg  7140
tatttctcat gaattagata gtgcatcttc tgaggtcaat taaaaggaga aaaaatacaa  7200
tttctcactt tgcatttagt caaaagaaaa aatgctttat agcaaaatga aagagaacat  7260
gaaatgcttc tttctcagtt tattggttga atgtgtatct atttgagtct ggaaataact  7320
aatgtgtttg ataattagtt tagtttgtgg cttcatggaa actccctgta aactaaaagc  7380
ttcagggtta tgtctatgtt cattctatag aagaaatgca aactatcact gtattttaat  7440
atttgttatt ctctcatgaa tagaaattta tgtagaagca aacaaaatac ttttacccac  7500
ttaaaaagag aatataacat tttatgtcac tataatcttt tgtttttttaa gttagtgtat  7560
attttgttgt gattatcttt ttgtggtgtg aataaatctt ttatcttgaa tgtaataaga  7620
atttggtggt gtcaattgct tatttgtttt cccacggttg tccagcaatt aataaaacat  7680
aacctttttt actgccta                                                7698

SEQ ID NO: 5            moltype = AA  length = 401
FEATURE                 Location/Qualifiers
source                  1..401
                        mol_type = protein
                        organism = Homo sapiens
SEQUENCE: 5
MNNLLCCALV FLDISIKWTT QETFPPKYLH YDEETSHQLL CDKCPPGTYL KQHCTAKWKT  60
VCAPCPDHYY TDSWHTSDEC LYCSPVCKEL QYVKQECNRT HNRVCECKEG RYLEIEFCLK  120
HRSCPPGFGV VQAGTPERNT VCKRCPDGFF SNETSSKAPC RKHTNCSVFG LLLTQKGNAT  180
HDNICSGNSE STQKCGIDVT LCEEAFFRFA VPTKFTPNWL SVLVDNLPGT KVNAESVERI  240
KRQHSSQEQT FQLLKLWKHQ NKDQDIVKKI IQDIDLCENS VQRHIGHANL TFEQLRSLME  300
SLPGKKVGAE DIEKTIKACK PSDQILKLLS LWRIKNGDQD TLKGLMHALK HSKTYHFPKT  360
VTQSLKKTIR FLHSFTMYKL YQKLFLEMIG NQVQSVKISC L                       401

SEQ ID NO: 6            moltype = DNA  length = 2087
FEATURE                 Location/Qualifiers
source                  1..2087
                        mol_type = genomic DNA
                        organism = Homo sapiens
SEQUENCE: 6
ggagacgcac cggagcgctc gcccagccgc cgcctccaag cccctgaggt ttccggggac  60
cacaatgaac aacttgctgt gctgcgcgct cgtgtttctg gacatctcca ttaagtggac  120
cacccaggaa acgtttcctc caaagtacct tcattatgac gaagaaacct ctcatcagct  180
gttgtgtgac aaatgtcctc ctggtaccta cctaaaacaa cactgtacag caaagtggaa  240
gaccgtgtgc gccccttgcc ctgaccacta ctacacagac agctggcaca ccagtgacga  300
gtgtctatac tgcagccccg tgtgcaagga gctgcagtac gtcaagcagg agtgcaatcg  360
cacccacaac cgcgtgtgcg aatgcaagga agggcgctac cttgagatag agttctgctt  420
gaaacatagg agctgccctc ctggatttgg agtggtgcaa gctggaaccc cagagcgaaa  480
tacagtttgc aaaagatgtc cagatgggtt cttctcaaat gagacgtcat ctaaagcacc  540
ctgtagaaaa cacacaaatt gcagtgtctt tggtctcctg ctaactcaga aaggaaatgc  600
aacacacgac aacatatgtt ccggaaacag tgaatcaact caaaaatgtg gaatagatgt  660
taccctgtgt gaggaggcat tcttcaggtt tgctgttcct acaaagttta cgcctaactg  720
gcttagtgtc ttggtagaca atttgcctgg caccaaagta aacgcagaga gtgtagagag  780
gataaaacgg caacacagct cacaagaaca gactttccag ctgctgaagt tatggaaaca  840
tcaaaacaaa gaccaagata tagtcaagaa gatcatccaa gatattgacc tctgtgaaaa  900
cagcgtgcag cggcacattg gacatgctaa cctcaccttc gagcagcttc gtagcttgat  960
ggaaagctta ccgggaaaga aagtgggagc agaagacatt gaaaaaacaa taaaggcatg  1020
caaacccagt gaccagatcc tgaagctgct cagtttgtgg cgaataaaaa atggcgacca  1080
```

-continued agacaccttg aagggcctaa tgcacgcact aaagcactca aagacgtacc actttcccaa 1140
aactgtcact cagagtctaa agaagaccat caggttcctt cacagcttca caatgtacaa 1200
attgtatcag aagttatttt tagaaatgat aggtaaccag gtccaatcag taaaaataag 1260
ctgcttataa ctggaaatgg ccattgagct gtttcctcac aattggcgag atcccatgga 1320
tgagtaaact gtttctcagg cacttgaggc tttcagtgat atctttctca ttaccagtga 1380
ctaattttgc cacagggtac taaaagaaac tatgatgtgg agaaaggact aacatctcct 1440
ccaataaacc ccaaatggtt aatccaactg tcagatctgg atcgttatct actgactata 1500
ttttccctta ttactgcttg cagtaattca actggaaatt aaaaaaaaaa aactagactc 1560
cattgtgcct tactaaatat gggaatgtct aacttaaata gctttgagat ttcagctatg 1620
ctagaggctt ttattagaaa gccatatttt tttctgtaaa agttactaat atatctgtaa 1680
cactattaca gtattgctat ttatattcat tcagatataa gatttgtaca tattatcatc 1740
ctataaagaa acggtatgac ttaattttag aaagaaaatt atattctgtt tattatgaca 1800
aatgaaagag aaaatatata tttttaatgg aaagtttgta gcatttttct aataggtact 1860
gccatatttt tctgtgtgga gtatttttat aattttatct gtataagctg taatatcatt 1920
ttatagaaaa tgcattattt agtcaattgt ttaatgttgg aaaacatatg aaatataaat 1980
tatctgaata ttagatgctc tgagaaattg aatgtacctt atttaaaaga ttttatggtt 2040
ttataactat ataaatgaca ttattaaagt tttcaaatta tttttta 2087

SEQ ID NO: 7 moltype = AA length = 432
FEATURE Location/Qualifiers
source 1..432
mol_type = protein
organism = Homo sapiens
SEQUENCE: 7
MERRRITSAA RRSYVSSGEM MVGGLAPGRR LGPGTRLSLA RMPPPLPTRV DFSLAGALNA 60
GFKETRASER AEMMELNDRF ASYIEKVRFL EQQNKALAAE LNQLRAKEPT KLADVYQAEL 120
RELRLRLDQL TANSARLEVE RDNLAQDLAT VRQKLQDETN LRLEAENNLA AYRQEADEAT 180
LARLDLERKI ESLEEEIRFL RKIHEEEVRE LQEQLARQQV HVELDVAKPD LTAALKEIRT 240
QYEAMASSNM HEAEEWYRSK FADLTDAAAR NAELLRQAKH EANDYRRQLQ SLTCDLESLR 300
GTNESLERQM REQEERHVRE AASYQEALAR LEEEGQSLKD EMARHLQEYQ DLLNVKLALD 360
IEIATYRKLL EGEENRITIP VQTFSNLQIR ETSLDTKSVS EGHLKRNIVV KTVEMRDGEV 420
IKESKQEHKD VM 432

SEQ ID NO: 8 moltype = DNA length = 5501
FEATURE Location/Qualifiers
source 1..5501
mol_type = genomic DNA
organism = Homo sapiens
SEQUENCE: 8
agagccagag caggatggag aggagacgca tcacctccgc tgctcgccgc tcctacgtct 60
cctcagggga gatgatggtg gggggcctgg ctcctggccg ccgtctgggt cctggcaccc 120
gcctctccct ggctcgaatg ccccctccac tcccgacccg ggtggatttc tccctggctg 180
gggcactcaa tgctggcttc aaggagaccc gggccagtga gcgggcagag atgatggagc 240
tcaatgaccg ctttgccagc tacatcgaga aggttcgctt cctggaacag caaaacaagg 300
cgctggctgc tgagctgaac cagctgcggg ccaaggagcc caccaagctg gcagacgtct 360
accaggctga gctgcgagag ctgcggctgc ggctcgatca actcaccgcc aacagcgccc 420
ggctggaggt tgagagggac aatctggcac aggacctggc cactgtgagg cagaagctcc 480
aggatgaaac caacctgagg ctggaagccg agaacaacct ggctgcctat agacaggaag 540
cagatgaagc caccctggcc cgtctggatc tggagaggaa gattgagtcg ctggaggagg 600
agatccggtt cttgaggaag atccacgagg aggaggttcg ggaactccag gagcagctgg 660
cccgacagca ggtccatgtg gagcttgacg tggccaagcc agacctcacc gcagccctga 720
aagagatccg cacgcagtat gaggcaatgg cgtccagcaa catgcatgaa gccgaagagt 780
ggtaccgctc caagtttgca gacctgacag acgctgctgc ccgcaacgcg gagctgctcc 840
gccaggccaa gcacgaagcc aacgactacc ggcgccagtt gcagtccttg acctgcgacc 900
tggagtctct gcgcggcacg aacgagtccc tggagaggca gatgcgcgag caggaggagc 960
ggcacgtgcg ggaggcggcc agttatcagg aggcgctggc gcggctggag gaagaggggc 1020
agagcctcaa ggacgagatg gcccgccact tgcaggagta ccaggacctg ctcaatgtca 1080
agctggccct ggacatcgag atcgccacct acaggaagct gctagagggc gaggagaacc 1140
ggatcaccat tcccgtgcag accttctcca acctgcagat tcgagaaacc agcctggaca 1200
ccaagtctgt gtcagaaggc cacctcaaga ggaacatcgt ggtgaagacc gtggagatgc 1260
gggatggaga ggtcattaag gagtccaagc aggagcacaa ggatgtgatg tgaggcagga 1320
cccacctggt ggcctctgcc ccgtctcatg aggggcccga gcagaagcag gatagttgct 1380
ccgcctctgc tggcacattt ccccagacct gagctcccca ccaccccagc tgctcccctc 1440
cctcctctgt ccctaggtca gcttgctgcc ctaggctccg tcagtatcag gcctgccaga 1500
cggcacccac ccagcaccca gcaactccaa ctaacaagaa actcaccccc aaggggcagt 1560
ctggaggggc atggccagca gcttgcgtta gaatgaggag gaaggagaga aggggaggag 1620
ggcgggggc acctactaca tcgccctcca catccctgat tcctgttgtt atggaaactg 1680
ttgccagaga tggaggttct ctcggagtat ctgggaactg tgcctttgag tttcctcagg 1740
ctgctggagg aaaactgaga ctcagacagg aaagggaagg ccccacagac aaggtagccc 1800
tggccagagg cttgttttgt cttttggttt ttatgaggtg ggatatccct atgctgccta 1860
ggctgacctt gaactcctgg gctcaagcag tctacccacc tcagcctcct gtgtagctgg 1920
gattatagat tggagccacc atgcccagct cagagggttg ttctcctaga ctgaccctga 1980
tcagtctaag atgggtgggg acgtcctgcc acctggggca gtcacctgcc cagatcccag 2040
aaggacctcc tgagcgatga ctcaagtgtc tcagtccacc tgagctgcca tccagggatg 2100
ccatctgtgg gcacgctgtg ggcaggtggg agcttgattc tcagcacttg ggggatctgt 2160
tgtgtacgtg gagagggatg aggtgctggg agggatagag gggggctgcc tggcccccag 2220
ctgtgggtac agagaggtca agcccaggag gactgccccg tgcagactgg aggggacgct 2280
ggtagagatg gaggaggagg caattgggat ggcgctaggc atacaagtag ggttgtgggg 2340
tgaccagttg cacttggcct ctggattgtg ggaattaagg aagtgactca tcctcttgaa 2400

-continued

```
gatgctgaaa caggagagaa aggggatgta tccatggggg cagggcatga ctttgtccca  2460
tttctaaagg cctcttcctt gctgtgtcat accaggccgc cccagcctct gagcccctgg  2520
gactgctgct tcttaacccc agtaagccac tgccacacgt ctgaccctct ccaccccata  2580
gtgaccggct gcttttccct aagccaaggg cctcttgcgg tcccttctta ctcacacaca  2640
aaatgtaccc agtattctag gtagtgccct attttacaat tgtaaaactg aggcacgagc  2700
aaagtgaaga cactggctca tattcctgca gcctggaggc cgggtgctca gggctgacac  2760
gtccacccca gtgcacccac tctgctttga ctgagcagac tggtgagcag actggtggga  2820
tctgtgccca gagatgggac tgggagggcc cacttcaggg ttctcctctc ccctctaagg  2880
ccgaagaagg gtccttccct ctccccaaga cttggtgtcc tttccctcca ctccttcctg  2940
ccacctgctg ctgctgctgc tgctaatctt cagggcactg ctgctgcctt tagtcgctga  3000
ggaaaaataa agacaaatgc tgcgcccttc cccagagtgg actctgatct gttcatgaga  3060
gggcgggact ggggccaaga tgtagccttt gacaagacca actcatttct tattactgat  3120
catctctggg gcccatgccc tcaccaaatt ccacccgcag ccaaagagga catacaccag  3180
ctccctccac tcttttcttc cttcctctcc ctgctacctg caactcaacc agcacaatct  3240
tcataggcaa gaaagcaaag cagctcaaac atgattcaac actgatcagt gtttaccact  3300
ggataaatct gagttcacac tttccttctc tgacctaaat gtgaagtcag gaaacacatg  3360
tgccctactt ccatcctgag ctcagtcccc aatctcccac cagcctcagg cccctccact  3420
tctcagatca ggtcccagac ctgcccatga aaatggggag caggctgtaa cagatttgtc  3480
cacatgttcc taccacctgt cccaacccag ggtacccacc cagagacatc tggtatcatt  3540
taacaaacac attgaaggac aactggtctt cagagctgaa gagagctcct agggggagaa  3600
gctgggacaa cagtgaaata agtagcagca gcaacgacag aagtgaatgg tgacaaagac  3660
tgctgtgatg agcaggtagc ctatcagggt gagctccaca gccgagcgag tctcaggatc  3720
tgagaacgag gctgggtagt gcccatgaga tgtcacaccc agccggaagc cagcaactag  3780
cacaccctgc ctccagcaat agtagatgcc ccggtcatcc agctgggtga agcggatgtg  3840
gagctggttg ccgtggtcaa tgaacaccct catggacctg ttgacaccct tcaggtactg  3900
tgtgcggtag aggtgctggc ggtctttgtc ccaggccact gcatgctctg gccgggcccc  3960
aggacaggag atgatgagtc catggcccag tctctgctgg tggaactgaa tgggcacctg  4020
gggcacccag ggccggctgc ccactttgga cacatagtta atgatggcca gcacgccctc  4080
ccggatggtc tttgtcttct cacagggtac taagcagctc cgaaccagca cctcaggcgt  4140
gtggtccctg gccttggtcc gcagcttcct tggcacagcc cttgagccac aagacaccac  4200
atcgggcacg gccttgaggt agcgtgggga gaggtctggg ctctgcaggt agcagaggcc  4260
gatgcgccac tgctccccac gcactccgca gcggtcacag gggtccatt cccagaaggt  4320
ggtgaagaca tggaggtgcc catagtattc atctgcaaag ggctcctggc ccttgtcctg  4380
gaaagtggcc accattccct cactgttctg gatgtccaca tcgtaggcgt aaaagtagtc  4440
cccttgcgg gtgccgcaga agtacaggcc tgagtcctca gactgagccc tgaaaaccaa  4500
caagctgaac atgcggatgc tgaagcgggt cagcatgtcg ctgcccacac gtacctgggc  4560
tgcctccgtc agcacccgcc catcaaagtc cgtcagcact ttggtgtggc tgctacctag  4620
gtgcttttgg tagaaccaga ctacagctgg cacctcttcg ggtttgcagt gacagggaag  4680
ctcaaagctc atgtcggcca ggtaggctgc attttcaaac atcaggaaag cagggcaggg  4740
ggtcctctga aaaatgtttt ccttctccac aatttcaaag gcctggagcc cccatgccca  4800
caggagcaca gtggtgaggg ccaggtgcat acctgaagga ggcaggggtc agaggggcag  4860
ggcaaaacca gggcattaaa ggctcatagg gctcctagaa agctctgcta agcggaagcc  4920
tctagatgag gaaaggatta tgcagccagg aaaagcagca acaatctgca gaggaagccg  4980
ccaagtgcaa ggcaatttat tcccagtgga tgtacaagat gcccttctaa cattccagac  5040
ctgatctcag ggtggggggg gaaagccatt ctagaacctg gcctttactc ccctttctag  5100
aacactggcg ctcacccaag aatgggtcaa aggaaaccgg aatgagaagg gcgggccgag  5160
gtgctcgggc agggagatct ctgcctcagt gctccaggcc ctgccctgcc agcctggtgg  5220
aaaagtcttt catcaacctg ggggatgaag gaaacccacc ctcctgcata tctggccatc  5280
cgggaggctg gctggacctg agctgatggc ttgggacttt cccaggccca acctgcacaa  5340
gaactgagtc tctaggggaa aattcaacac ctcaaatgat gtagtatttg atcatttgtt  5400
gattacatgt ccattcattg gtttggggct ataaacattc ttgttaagag ctgtggagat  5460
cagtgtttgt ttaccataaa gattttgctt tttccctttt a                      5501
```